United States Patent [19]

Maki et al.

[11] Patent Number: 5,759,802

[45] Date of Patent: Jun. 2, 1998

[54] PRODUCTION OF HUMAN SERUM ALUBUMIN A

[75] Inventors: Noboru Maki; Shintaro Yagi; Kazuya Watanabe; Masanori Suzuki, all of Iruma-gun, Japan

[73] Assignee: Tonen Corporation, Tokyo, Japan

[21] Appl. No.: 417,429

[22] Filed: Oct. 5, 1989

[30] Foreign Application Priority Data

| Oct. 26, 1988 | [JP] | Japan | 63-268302 |
| Jun. 19, 1989 | [JP] | Japan | 1-154755 |
| Jun. 19, 1989 | [JP] | Japan | 1-154756 |
| Jun. 19, 1989 | [JP] | Japan | 1-154758 |
| Jun. 21, 1989 | [JP] | Japan | 1-156688 |

[51] Int. Cl.$^6$ ............... C12D 21/06; C12D 21/04; C12N 15/00; C12N 1/14
[52] U.S. Cl. ............. 435/69.1; 435/69.8; 435/71.1; 435/255.2; 435/320.1; 935/11; 935/60
[58] Field of Search ............... 435/172.3, 256, 435/69.6, 71.1, 69.1, 69.8, 255.2, 320.1; 536/27, 23.1

[56] References Cited

U.S. PATENT DOCUMENTS 4,937,193 6/1990 Hirchcliffe et al. .

FOREIGN PATENT DOCUMENTS

| 0073646A | 3/1983 | European Pat. Off. . |
| 0079739A | 5/1983 | European Pat. Off. . |
| 0206733A | 12/1986 | European Pat. Off. . |
| 0308381A | 3/1989 | European Pat. Off. . |
| 0319641A | 6/1989 | European Pat. Off. . |
| 0329127A | 8/1989 | European Pat. Off. . |
| 8902463 | 3/1989 | WIPO . |
| 9001063 | 2/1990 | WIPO . |

OTHER PUBLICATIONS

Lawn et al. (1981) "The sequence of human serum albumin cDNA . . ." Nucl. Acid. Res. 9, 6103–6114.

Briggs et al (1986) "Conformation of Signal Peptides . . ." Science 233, 206–208.

Taussiq et al. (1983) "Nucleotide sequence of the yeast SUC2 gene" Nucl. Acid. Res. 11, 1943–1954.

Kurjan et al. (1982) "Structure of a Yeast Pheromone Gene (MF2)..." Cell 30, 933–943.

Brake et. al. (1984) "α–Factor directed synthesis" Proced. Natl. Acad. Sci 81, 4642.

Hagenauer —Tsapis (1984) "A Deletion . . . Yeast Acid Phosphatase" 4, 2668–2675.

T. Etcheverry et al. Bio/Technology vol. 4, 1986, 726–730.

M. Monod et al. Chemical Abstracts vol. 109, No. 23, p. 265, 206830y, Dec. 5, 1988.

S.M. Kingsman et al., Biotechnology and Genetic Engineering Reviews, vol. 3, pp. 377–416, Sep. 1985.

K. Yoshimura et al., Biochemical and Biophysical Reseach Communications, vol. 145, No. 2, pp. 712–718, Jun. 15, 1989.

Y. Yamamot et al., Biochemical and Biophysical Research Communications, vol. 149, No. 2, pp. 431–436, Dec. 16, 1989.

W. Garten et al., Chemical Abstracts vol. 96, Pat 7, P460, 50432V, Feb. 15, 1982.

*Primary Examiner*—Deborah Crouch
*Attorney, Agent, or Firm*—Foley & Lardner

[57] ABSTRACT

A process for the production of human serum albumin A (HSA) characterized by culturing host cells transformed with the plasmids containing a leader DNA sequence and a cDNA coding for mature HSA to produce and secrete mature HSA, and recovering the mature HSA. As the leader HSA sequence, a cDNA coding for the prepro sequence of HSA, a synthetic DNA coding for the prepro sequence of HSA, by the codons frequently used in a selected host, a DNA coding for a chimeric leader peptide, a DNA coding for MFα1 prepro sequence, or a DNA coding for PH05 signal peptide, is used.

7 Claims, 41 Drawing Sheets

TERMINATOR CASSETTE VECTOR

Fig. 9

HSA-1 5'- AAGGGAAATAAAGGTTACCACCACTTCATTGTGCCAAAGGC -3'

REGION CORRESPONDING TO 5'-NON-CODING REGION~Met1~Leu9
(12 NUCLEOTIDES)

HSA-2 5'- AAGGTCCGCCCCTGTCATCAGCACATTCAAGCAGATCTCC -3'

REGION CORRESPONDING TO Gly248~Leu260

HSA-3 5'- TAGATGTTATAAGCCTAAGGCAGCTTGACTTGCAGCAAC -3'

REGION CORRESPONDING TO Val576~Leu585~3'-NON-CODING REGION
(6 NUCLEOTIDES)

Fig. 11A

```
Asp Ala His Lys Ser Glu Val Ala His Arg Phe Lys Asp Leu Gly Glu Asn Phe Lys Ala Leu Val
GAT GCA CAC AAG AGT GAG GTT GCT CAT CGG TTT AAA GAT TTG GGA GAA AAT TTC AAA GCC TTG GTG

Leu Ile Ala Phe Ala Gln Tyr Leu Gln Gln Cys Pro Phe Glu Asp His Val Lys Leu Val Asn Glu Val
TTG ATT GCC TTT GCT CAG TAT CTT CAG CAG TGT CCA TTT GAA GAT CAT GTA AAA TTA GTG AAT GAA GTA
                50

Thr Glu Phe Ala Lys Thr Cys Val Ala Asp Glu Ser Ala Glu Asn Cys Asp Lys Ser Leu His Thr Leu
ACT GAA TTT GCA AAA ACA TGT GTT GCT GAT GAG TCA GCT GAG AAT TGT GAC AAA TCA CTT CAT ACC CTT

Phe Gly Asp Lys Leu Cys Thr Val Ala Thr Leu Arg Glu Thr Tyr Gly Glu Met Ala Asp Cys Cys Ala
TTT GGA GAC AAA TTA TGC ACA GTT GCA ACT CTT CGT GAA ACC TAT GGT GAA ATG GCT GAC TGC TGT GCA

Lys Gln Glu Pro Glu Arg Asn Glu Cys Phe Leu Gln His Lys Asp Asp Asn Pro Asn Leu Pro Arg Leu
AAA CAA GAA CCT GAG AGA AAT GAA TGC TTC TTG CAA CAC AAA GAT GAC AAC CCA AAC CTC CCC CGA TTG

Val Arg Pro Glu Val Asp Val Met Cys Thr Ala Phe His Asp Asn Glu Glu Thr Phe Leu Lys Lys Tyr
GTG AGA CCA GAG GTT GAT GTG ATG TGC ACT GCT TTT CAT GAC AAT GAA GAG ACA TTT TTG AAA AAA TAC
```

Fig. 11B

```
                                                              150
Leu Tyr Glu Ile Ala Arg Arg His Pro Tyr Ala Pro Glu Leu Leu Phe Phe Ala Lys Arg Tyr
TTA TAT GAA ATT GCC AGA AGA CAT CCT TAC GCC CCG GAA CTC CTT TTC TTT GCT AAA AGG TAT

Lys Ala Ala Phe Thr Glu Cys Cys Gln Ala Ala Asp Lys Ala Ala Cys Leu Leu Pro Lys Leu Asp Glu
AAA GCT GCT TTC ACA GAA TGT TGC CAA GCT GCT GAT AAA GCT GCC TGC CTG TTG CCA AAG CTC GAT GAA

200
Leu Arg Asp Glu Gly Lys Ala Ser Ser Ala Lys Gln Arg Leu Lys Cys Ala Ser Leu Gln Lys Phe Gly
CTT CGG GAT GAA GGG AAG GCT TCG TCT GCC AAA CAG AGA CTC AAG TGT GCC AGT CTC CAA AAA TTT GGA

Glu Arg Ala Phe Lys Ala Trp Ala Val Ala Arg Leu Ser Gln Arg Phe Pro Lys Ala Glu Phe Ala Glu
GAA AGA GCT TTC AAA GCA TGG GCA GTA GCT CGC CTG AGC CAG AGA TTT CCC AAA GCT GAG TTT GCA GAA

250
Val Ser Lys Leu Val Thr Asp Leu Thr Lys Val His Thr Glu Cys Cys His Gly Asp Leu Leu Glu Cys
GTT TCC AAG TTA GTG ACA GAT CTT ACC AAA GTC CAC ACG GAA TGC TGC CAT GGA GAT CTG CTT GAA TGT

Ala Asp Asp Arg Ala Asp Leu Ala Lys Tyr Ile Cys Glu Asn Gln Asp Ser Ile Ser Ser Lys Leu Lys
GCT GAT GAC AGG GCG GAC CTT GCC AAG TAT ATC TGT GAA AAT CAA GAT TCG ATC TCC AGT AAA CTG AAG
```

Fig. 11C

```
Glu Cys Cys Glu Lys Pro Leu Leu Glu Lys Ser His Cys Ile Ala Glu Val Glu Asn Asp Glu Met Pro
GAA TGT TGT GAA AAA CCT CTG TTG GAA AAA TCC CAC TGC ATT GCC GAA GTG GAA AAT GAT GAG ATG CCT
300
Ala Asp Leu Pro Ser Leu Ala Ala Asp Phe Val Glu Ser Lys Asp Val Cys Lys Asn Tyr Ala Glu Ala
GCT GAC TTG CCT TCA TTA GCT GCT GAT TTT GTT GAA AGT AAG GAT GTT TGC AAA AAC TAT GCT GAG GCA

Lys Asp Val Phe Leu Gly Met Phe Leu Tyr Glu Tyr Ala Arg Arg His Pro Asp Tyr Ser Val Val Leu
AAG GAT GTC TTC CTG GGC ATG TTT TTG TAT GAA TAT GCA AGA AGG CAT CCT GAT TAC TCT GTC GTG CTG
        350
Leu Leu Arg Leu Ala Lys Thr Tyr Glu Thr Thr Leu Glu Lys Cys Cys Ala Ala Ala Asp Pro His Glu
CTG AGA CTT GCC AAG ACA TAT GAA ACC ACT CTA GAG AAG TGC TGT GCC GCT GCA GAT CCT CAT GAA

Cys Tyr Ala Lys Val Phe Asp Glu Phe Lys Pro Leu Val Glu Glu Pro Gln Asn Leu Ile Lys Gln Asn
TGC TAT GCC AAA GTG TTC GAT GAA TTT AAA CCT CTT GTG GAA GAG CCT CAG AAT TTA ATC AAA CAA AAT
                              400
Cys Glu Leu Phe Glu Gln Leu Gly Glu Tyr Lys Phe Gln Asn Ala Leu Leu Val Arg Tyr Thr Lys Lys
TGT GAG CTT TTT GAG CAG CTT GGA GAG TAC AAA TTC CAG AAT GCG CTA TTA GTT CGT TAC ACC AAG AAA
```

Fig. 11D

```
Val Pro Gln Val Ser Thr Pro Thr Leu Val Glu Val Ser Arg Asn Leu Gly Lys Val Gly Ser Lys Cys
GTA CCC CAA GTG TCA ACT CCA ACT CTT GTA GAG GTC TCA AGA AAC CTA GGA AAA GTG GGC AGC AAA TGT

450
Cys Lys His Pro Glu Ala Lys Arg Met Pro Cys Ala Glu Asp Tyr Leu Ser Val Val Leu Asn Gln Leu
TGT AAA CAT CCT GAA GCA AAA AGA ATG CCC TGT GCA GAA GAC TAT CTA TCC GTC CTG AAC CAG TTA

Cys Val Leu His Glu Lys Thr Pro Val Ser Asp Arg Val Thr Lys Cys Cys Thr Glu Ser Leu Val Asn
TGT GTG TTG CAT GAG AAA ACG CCA GTA AGT GAC AGA GTC ACA AAA TGC TGC ACA GAG TCC TTG GTG AAC
                                                                500
Arg Arg Pro Cys Phe Ser Ala Leu Glu Val Asp Glu Thr Tyr Val Pro Lys Glu Phe Asn Ala Glu Thr
AGG CGA CCA TGC TTT TCA GCT CTG GAA GTC GAT GAA ACA TAC GTT CCC AAA GAG TTT AAT GCT GAA ACA

Phe Thr Phe His Ala Asp Ile Cys Thr Leu Ser Glu Lys Glu Arg Gln Ile Lys Lys Gln Thr Ala Leu
TTC ACC TTC CAT GCA GAT ATA TGC ACA CTT TCT GAG AAG GAG AGA CAA ATC AAG AAA CAA ACT GCA CTT

550
Val Glu Leu Val Lys His Lys Pro Lys Ala Thr Lys Glu Gln Leu Lys Ala Val Met Asp Asp Phe Ala
GTT GAG CTT GTG AAA CAC AAG CCC AAG GCA ACA AAA GAG CAA CTG AAA GCT GTT ATG GAT GAT TTC GCA
```

Fig. 11E

Ala Phe Val Glu Lys Cys Cys Lys Ala Asp Asp Lys Glu Thr Cys Phe Ala Glu Glu Gly Lys Lys Leu
GCT TTT GTA GAG AAG TGC TGC AAG GCT GAC GAT AAG GAG ACC TGC TTT GCC GAG GAG GGT AAA AAA CTT

Val Ala Ala Ser Gln Ala Ala Leu Gly Leu End
GTT GCT GCA AGT CAA GCT GCC TTA GGC TTA TAA

M.W. (Kd)
67
43
30
20
4.4

(1) (2) (3) (4)

(1) YEAST HSA
(2) YEAST HSA + HUMAN SERUM HSA
(3) HUMAN SERUM HSA (1) (2)

DIMER
MONOMER (1) YEAST HSA
(2) HUMAN SERUM HSA

1. M.W. MARKER
2. YEAST HSA
3. HUMAN SERUM HSA

1. YEAST HSA
2. HUMAN SERUM HSA 1, 4. pI STANDARDS
2. HUMAN SERUM HSA
3. YEAST HSA 1 2 3

1. CELL EXTRACT
2. CULTURE SUPERNATANT
3. HUMAN SERUM HSA

1. M.W. MARKER
2. YEAST HSA
3. HUMAN SERUM HSA

1. YEAST HSA
2. HUMAN SERUM HSA 1, 4. pI STANDARD

2. HUMAN SERUM HSA

3. YEAST HSA

1. CELL EXTRACT
2. CULTURE SUPERNATANT
3. HUMAN SERUM HSA

PRODUCTION OF HUMAN SERUM ALUBUMIN A

BACKGROUND OF THE INVENTION

1. Field of the Invention

The present invention relates to the production of human serum albumin A (HSA) in eukaryatic cells such as yeast cells and gene components used thereof. According to the present invention, mature human serum albumin A is extracellularly secreted, and therefore can be easily recovered and purified, thus providing industrial advantages.

2. Description of the Related Art

As known processes for the production of human serum albumin by genetic engineering, there are processes using *Escherichia coli* (Lawn et al., Nucleic Acids Res. 9, 6103–6114, 1981; Latta et al., Biotechnology 5, 1309–1314, 1987; Japanese Unexamined Patent Publication, KOKAI 58-150517), a process using *Bacillus subtilis* (Saunders et al., J. Bacteriol., 169, 2917–2925, 1987), and a process using Yeast [Etcheverry et al., Biotechnology, 4, 726–730, 1986]. These processes, however, are inadvantageous in that they provide serum albumins having an aminoacid sequence differing to some extent from that of natural human serum albumin A; the produced serum albumin is precipitated in an insoluble form; the processing efficiency of the signal peptide is low; and, the extracellular secretion is difficult.

Generally, as an efficient method for secreting a desired protein by a genetic engineering procedure, a method is known wherein a fused protein comprising the desired protein and a prepropeptide (signal peptide+propeptide) is expressed in a host cell and then intracellularly cleaved (processed) by enzymes of the host, and then, extracellularly secreted. According to this process, however, the fused protein must be cleaved twice by enzymes of the host to be a mature protein, resulting in lower yield of the mature protein and contamination of the mature protein with residual fused protein. To overcome these difficulties, a method wherein a fused protein comprises a desired protein and a signal peptide alone (excluding propeptide) has been considered. According to this method, although a desired mature protein is formed by a single cleavage, problems remain of a low processing efficiency and a low extracellular secretion efficiency.

According to the generally accepted loop model, it is believed that a secretory protein interacts, via the basic amino acid thereof positioned near the N-terminal of a signal peptide, with the inside of a cell membrane thereof, and then interacts, via a stretch of hydrophobic amino acid residues of the signal peptide, with a lipid bilayer of the cell membrane, resulting in an insertion of the protein to the cell membrane (Inouye, S., Wang, S., Seligawa, J., Halegova, S. and Inouye, M., Proc. Natl. Acad. Sci. U.S.A., 74, 1004–1008, 1977). The common structural properties of signal peptide are as follows: 1) there are basic amino acids near the amino terminus; 2) there is a cluster comprising hydrophobic amino acid residues; and 3) a carboxy terminus of a signal peptide which is cleaved by signal peptidase is an amino acid having a small side chain. As a result of an experiment carried out to determine whether leader sequences prepared by introduction of in vitro mutagenesis actually function in an in vivo or in vitro translation/translocation system, it was reported that conformation of the cluster of the hydrophobic amino acid residues is important if the signal peptide is to exhibit its function. More specifically, the importance of an α-helix structure formed in a hydrophobic amino acid cluster has been shown by the following experiment.

An interaction between a signal peptide of *E. coli* Lam B protein and a lipid monolayer was tested, and secondary structures of a signal peptide which can penetrate the membrane and a signal peptide which cannot penetrate the membrane, depending on different pressures, were analyzed using circular dichroism and Fourie transform infrared spectrometry. As a result, it was found that the signal peptide which can penetrate the membrane has a tendency to form the α-helix structure, and the signal peptide which cannot penetrate the membrane is most likely to form the β-turn structure (Briggs, M. S., Cornell, D. G., Dluhy, R. R. and Gierash, L. M., Science 233, 203–208, 1986). From these results, a model was proposed wherein a signal peptide first forms the β-turn structure by an interaction with the membrane, and this structure is transformed to the α-helix structure as the signal peptide is inserted to the membrane.

SUMMARY OF THE INVENTION

Accordingly, the present invention provides processes for the production of human serum albumin, which processes can provide a large amount of secreted mature human serum albumin A in a soluble form and in the same steric structure as that of natural human serum albumin, thereby enabling an easy recovery and purification of the human serum albumin by an industrial process.

According to an another aspect of the present invention, there are provided a novel leader sequence which provide a conversion of a precursor fused protein to a mature protein by a single cleavage (processing), and an effective extracellular secretion of the mature protein.

More specifically, the present invention provides a DNA comprising a leader DNA coding for prepropeptide of human serum albumin A (HSA) and cDNA coding for, mature HSA present downstream of the leader DNA; a recombinant DNA comprising a DNA coding for prepropeptide of HSA, cDNA coding for mature HSA, a poly A addition signal and poly (A) sequence in this order; a plasmid comprising a promoter and terminator functional in yeast cells wherein the recombinant DNA has been inserted between the promoter and terminator in an orientation which allows expression of the cDNA; yeast cells transformed with the plasmid; and a process for the production of mature HSA comprising culturing the transformed yeast cells to produce and secrete the mature HSA, and recovering the secreted HSA.

The preset invention also provides a DNA comprising a leader DNA coding for a chimeric leader peptide and a cDNA coding for mature HSA present downstream of the leader DNA wherein the chimeric leader peptide comprises at the N-terminal side thereof an amino acid sequence readily forming an α-helix and at the C-terminal side thereof an amino acid sequence corresponding to a C-terminal of a leader sequence of a protein which is efficiently processed in a selected host; a recombinant DNA comprising a DNA coding for chimeric leader peptide, a CDNA coding for mature HSA, a poly A addition signal and a poly A sequence in this order, wherein the chimeric leader peptide comprises at the N-terminal side thereof an amino acid sequence readily forming an α-helix and at the C-terminal side thereof an amino acid sequence corresponding to a C-terminal of a leader sequence of a protein which is efficiently processed in a selected host; a plasmid comprising a promoter and terminator functional a in host cells wherein the recombinant DNA has been inserted between the promoter and terminator in an orientation which allows expression of the cDNA; a host transformed with the plasmid; a process for the production of mature HSA comprising culturing the transformed host to produce and secrete mature HSA, and recovering the mature HSA.

The present invention moreover provides a DNA comprising a leader DNA coding for prepro sequence of MFα1 and a cDNA coding for mature HSA present downstream of the leader DNA; a recombinant DNA comprising a leader DNA coding for a prepro sequence of MFα1, a cDNA coding for mature HSA, a poly A additional signal, and a poly A sequence, in this order; a plasmid comprising a promoter and terminator functional in yeast cells wherein the recombinant DNA has been inserted between the promoter and terminator in an orientation which allows the expression of the cDNA; yeast cells transformed with the plasmid; and a process for the production of mature HSA in comprising culturing the transformed yeast cells to produce and secrete mature HSA, and recover the mature HSA.

The present invention still further provides a DNA comprising a leader DNA coding for a yeast acid phosphatase (PH05) signal sequence and a cDNA coding for mature HSA present downstream of the leader DNA; a recombinant DNA comprising a leader DNA coding for a PH05 signal sequence, a cDNA coding for mature HSA, a poly (A) additioanl signal, and poly (A) sequence in this order; a plasmid comprising a promoter and terminator functional in yeast cells wherein the recombinant DNA has been inserted between the promoter and terminator in an orientation which allows the expression of the cDNA; yeast cells transformed with the plasmid; a process for the production of mature HSA comprising culturing the transformed yeast cells to produce and secrete mature HSA, and recovering the mature HSA; and a process for the production of mature HSA comprising culturing the transformed yeast cells to produce a precursor HSA having a signal peptide, recovering the precursor HSA, and processing the precursor HSA in vitro to form mature HSA.

Moreover, the present invention provides a chimeric leader peptide comprising at the N-terminal side thereof an amino acid sequence readily forming an α-helix, and at the C-terminal side thereof, an amino acid sequence corresponding to the C-terminal of a leader sequence of a protein efficiently processed in vivo, and a DNA coding for the above-mentioned chimeric leader peptide.

BRIEF EXPLANATION OF THE DRAWINGS

FIGS. 3-1 to 3-2 show a process for the construction of ADHI promoter cassette vector pDE6-10(Xho);

FIGS. 4-1 to 4-2 show a process for the construction of ADHI terminator cassette vector pUC-ATE;

FIG. 9 shows nucleotide sequences of three probes used for screening HSA cDNA clones;

FIGS. 11-1 to 11-5 show a nucleotide sequence of a cDNA coding for the entire HSA;

DESCRIPTION OF THE PREFERRED EMBODIMENT

1. Gene System

A. Host

Figure 1:
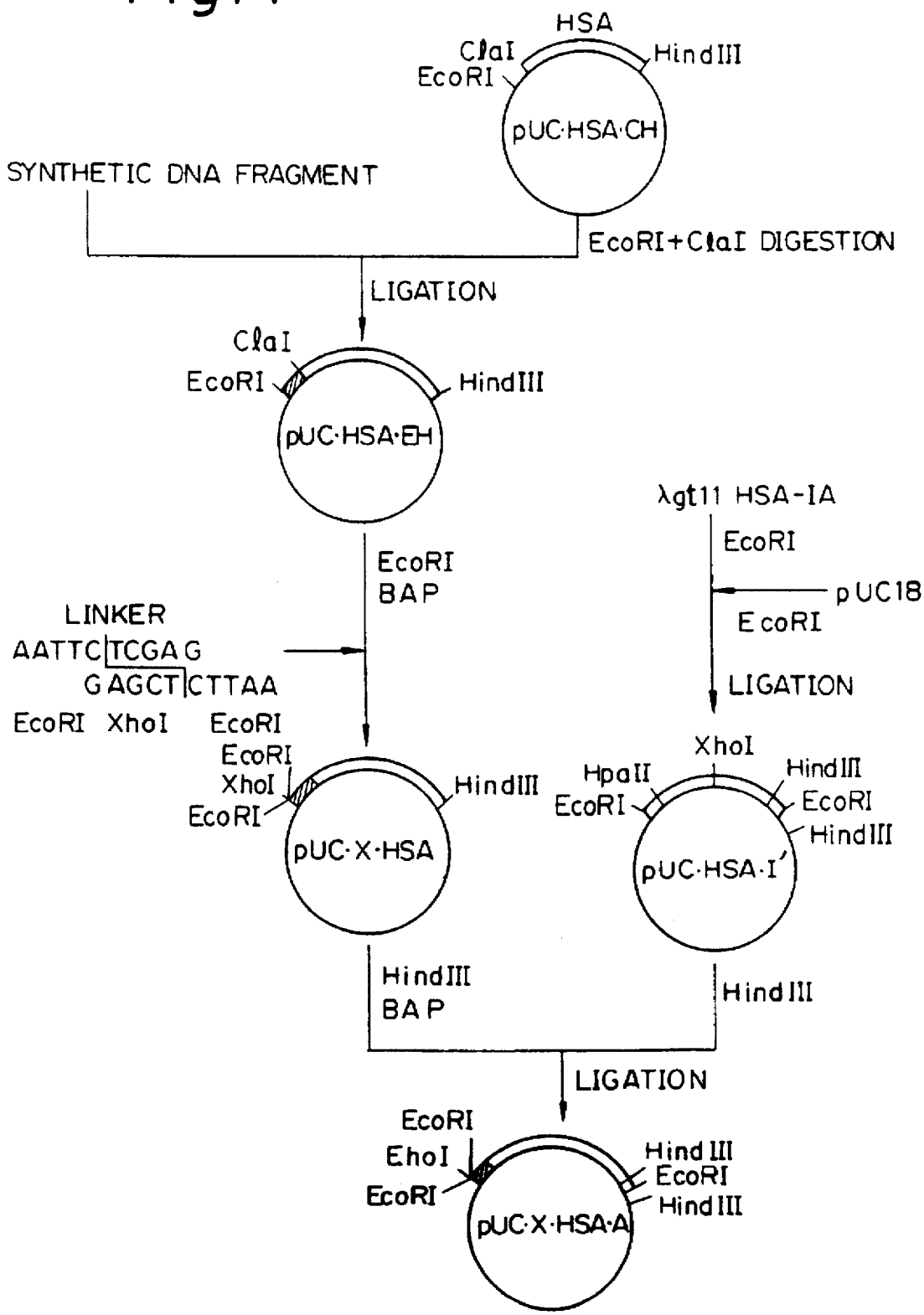
FIG. 1 shows a process for the construction of plasmid pUC-X-HSA-A.

Since normal HSA molecule contains many disulfide linkages, to obtain normal HSA having the same secondary structure as that of natural HSA by a recombinant DNA technique, the disulfide linkages must be correctly formed in a producer host cell employed. Recently it has been suggested that enzymes such as protein disulfideisomerase, peptidylprolyl cis-trans isomerase, and the like are involved in the formation of a normal secondary and tertiary structure. It is expected that the action of such folding enzymes is not present, or is present at a very low level, in prokaryotic cells such as E. coli or Bacillus subtilis, because these prokaryotic cells have very few proteins which contain many disulfide linkages and do not form a complicated secondary and/or tertiary structure. Nevertheless, it is known that, although higher eukaryatic cells including human cells secrete various kinds of proteins including glycoproteins and other modified proteins having a highly complicated secondary and/or tertiary structure, yeast and lower eukaryates also secrete protein via a route similar to that of higher eukaryates (Huffaker, T. C. and Robbins, P. W., J. Biol. Chem., 257, 3203–3210, 1982; Snider, M. D. in Ginsburg, V. and Robbins, P. W. (eds) Biology of Carbohydrates, Vol. 2, Wiley, New York, 1984, pp. 163–198). Accordingly, many attempts have been made to express heterogeneous (especially mammalian) gene in yeast cells resulting in extracellular secretion of the expression products.

Generally it is considered that the use of yeast cells as a host is advantageous in that:

1. Fermentation in a large amount of culture with a high cell density is easy and economical. Moreover, culturing of yeast cells does not require a precisely controlled apparatus necessary in the case of an animal or plant cell culture;

2. Much experience has been accumulated in yeast fermentation;

3. Knowledge of molecular genetics on yeast is rapidly increasing;

4. Introduction into a cell and integration into a genome of a foreign genetic material is easy;

5. Genetic and physiological understanding of the intracellular transport of proteins and extracellular secretion thereof is rapidly increasing;

6. A foreign genetic material can be present in a yeast cell in four different states by a selection of an appropriate plasmid vector, i.e., it is maintained as an episome by using YEp-type plasmid; it is integrated into a genome by using YIp plasmid; it can replicate simultaneously with cell division by using YCp plasmid containing centromere; and it can be autonomously replicated by using YRp plasmid containing an autonomous replication sequence (ARS);

7. A yeast cell has a mechanism for intracellular processing of a signal peptide and prosequence;

8. Although obigosaccharides found in glycoprotein synthesized by a yeast cell contain relatively large amounts of mannose and is different from oligosacchaindes in the glycoprotein of higher animals, a process of the addition of a core oligosacchanide chain occurring in a yeast endoplasmic reticulum is same as the corresponding process in a higher animal, and therefore, the only difference lies in the addition of an outer oligosacchanide chain;

9. A yeast transformant can grow in a synthetic medium supplemented with vitamins and trace elements; and, 10. A yeast transformant can be cultured in a medium containing crude sugar instead of pure glucose.

Because of the above-mentioned advantages, a yeast host is preferably used according to the present invention.

B. Sequence for promoting secretion of desired protein

According to the present invention, to promote the secretion of a desired protein, a sequence for promoting the secretion is used.

The sequences used in the present invention for this purpose are as follows:

(1) Prepro sequence naturally linked to HSA;

(2) Chimeric leader sequence (3) MFal leader sequence; and (4) Signal peptide of yeast acid phosphatase.

Prepro sequence naturally linked to HSA

In mammalian hepatocyte, HSA is synthesized as a precursor protein having at the N-terminal side thereof a prepro sequence. This prepro sequence is necessary for an efficient secretion of mature HSA. Cutting off the prepro sequence during the secretion is essential for providing mature HSA. Since yeast is a eukaryote, it is expected that the same phenomenon as found in the hepatocyte will occur in the yeast cell. Accordingly, the present invention employs a prepro sequence naturally linked to HSA.

In one embodiment, as a DNA coding for the prepro sequence, cDNA naturally linked with a CDNA coding for HSA is used. This cDNA has the following sequence:

| Met | Lys | Trp | Val | Thr | Phe | Ile | Ser | Leu | Leu |
|-----|-----|-----|-----|-----|-----|-----|-----|-----|-----|
| ATG | AAG | TGG | GTA | ACC | TTT | ATT | TCC | CTT | CTT |
| Phe | Leu | Phe | Ser | Ser | Ala | Tyr | Ser | Arg | Gly |
| TTT | CTC | TTT | AGC | TCG | GCT | TAT | TCC | AGG | GGT |
| Val | Phe | Arg | Arg |
| GTG | TTT | CGT | CGA. |

In another embodiment, as a DNA coding for the prepro sequence, a synthetic oligonucleotide comprising codons which are frequently used in yeast and coding for an amino acid sequence of the natural prepro sequence of HSA, is used. The following codons, for example, are frequently used in yeast:

Lys=AAG Trp=TGG Val=GTT Thr=ACT Phe=TTC Ile=ATC Ser= TCT Leu=TTG Ala=GCT Tyr=TAC Arg=AGA Gly=GGT

An embodiment of a synthetic oligonucleotide coding for the natural prepro sequence of HSA is represented by the following sequence:

```
AA  TTC ATG AAG TGG    GTT ACT    TTC ATC    TCT TTG
    G   TAG TTC ACC    CAA TGA    AAG TAG    AGA AAC
            Met Lys Trp Val Thr    Phe Ile    Ser Leu
EcoR I>

TTG TTC TTG TTC    TCT TCT    GCT TAC    TCT AGA
AAC AAG AAC AAG    AGA AGA    CGA ATG    AGA TCT
Leu Phe Leu Phe    Ser Ser    Ala Tyr    Ser Arg
GGT GTT TTC AGA    CG
CCA CAA AAG TCT    GCG C
Gly Val Phe Arg    Arg
```

The above-sequence has an EcoR I cohesive end upstream of the Met codon ATG, and this cohesive end is used to insert the sequence into a vector. The above sequence has a codon CGC coding for the C-terminal Arg, which provides a Cla I end used to insert the fragment into a vector.

Chimeric leader sequence

In one embodiment of the present invention, to promote the secretion of a desired mature protein, an artificial chimeric leader sequence is used. The chimeric leader sequence has at the N-terminal side thereof an amino acid sequence which readily forms an α-helix, and at the C-terminal side thereof, an amino acid sequence which is readily processed in the used host. The sequence which readily forms the α-helix is, for example, an amino acid sequence containing a high ratio of leucine, for example, an amino acid sequence containing more than one continuous leucine residue. Moreover, other neutral amino acids such as alanine, methionine, phenylalanine, tyrosine, and the like have a tendency to form an α-helix.

The C-terminal portion of the present chimeric leader sequence, which provides a processing site, is, for example, a corresponding site of a leader sequence of a protein which is efficiently processed in a selected host. For example, when yeast is used as a host, a C-terminal portion of signal peptide of secretion-type invertase SUC2, a signal peptide of acid phosphatase PHO5, an MFα1 signal peptide, and a signal peptide of killer toxin, and the like may be mimicked. The amino acid sequences of these signal peptides are as follows:

|  | processing site ⟶ |
|---|---|
| SUC 2 | MLLQAFLFLLAGFAAKISA ↓ |
| PHO 5 | MFKSVVYSILAASLANA ↓ |
| MFα1 | MRFPSIFTAVLFAASSALA |
| Killer toxin | MTKPTQVLVRSVSILFFITLLHLVVA |

In the present chimeric leader sequence, the N-terminal portion responsible for the formation of the α-helix and the C-terminal portion responsible for processing are linked directly or via a linker. The linker consists of one or more than one amino acid. The present chimeric leader sequence can be formed by any combination of the N-terminal portion, the C-terminal portion, and the optional linker. An embodiment of the chimeric leader sequence formed by a combination of an N-terminal portion containing some continuous leucine residue and an C-terminal portion corresponding to a signal peptide of a secretion-type invertase SUC2 is represented as follows:

| Met | Lys | Leu | Leu | Leu | Leu | Leu | Leu | Leu | Leu |
|-----|-----|-----|-----|-----|-----|-----|-----|-----|-----|
| ATG | AAG | TTG | TTG | CTC | CTC | CTT | CTT | TTG | CTC |
| TAC | TTC | AAC | AAC | GAG | GAG | GAA | GAA | AAC | GAG |
| Phe | Leu | Phe | Ser | Ala | Lys | Ile | Ser | Ala | |
| TTC | TTG | TTC | TGT | GCT | AAG | ATT | TCT | GCC | |
| AAG | AAC | AGA | AGA | CGA | TTC | TAA | AGA | CGG | |

In the above-described sequences, the first line represents an amino acid sequence, and the second and third lines represent an embodiment of a nucleotide sequence coding for the amino acid sequence.

Although a nucleotide sequence coding for the present chimeric leader sequence may comprise any codons which can be used in a used host, preferably nucleotide sequence comprises codons which are frequently used in a used host. For example, when yeast is used as a host, a nucleotide sequence coding for the present leader sequence is preferably designed, using well known codons frequently used in yeast.

MFα1 leader sequence

For an efficient expression and secretion of HSA in mammalian hepatocyte, a prepro sequence linked to the N-terminal of mature HSA is essential. Since it is known that yeast and lower eukaryotes secrete protein by a process similar to that of mammals, it is expected that, where a desired foreign protein is expressed in a yeast cell and secreted therefrom in the form of a mature protein, a prepro sequence linked to the mature protein must be cut off during the secretion. Accordingly, in an embodiment of the present invention, a yeast MFα1 leader sequence is used as a prepro sequence satisfying the above-mentioned requirements.

The MFα1 gene encodes a polypeptide consisting of 165 amino acid residues, which the polypeptide comprises a leader sequence consisting of 89 amino acid and 4 copies of a pheromone α-factor each separated by a short spacer peptide. The leader sequence consists of a hydrophobic signal peptide (prepeptide) consisting of 22 amino acid and a hydrophilic propeptide consisting of 67 amino acid. The α-prepropeptide synthesized in the yeast cell is cleaved by a signal peptidase on the endoplasmic reticulum to release the signal peptide, cleaved by a membrane-associated serine protease KEX2 which cleaves at the carboxy terminal site of a pair of two basic amino acids including arginine (-Lys-Arg-, or -Arg-Arg), and further cleaved by carboxypeptidase B(KEX1) and dipeptidyl amino peptidase (STE13) to provide the α-factor which is extracellularly secreted.

For the secretion of a foreign protein expressed in yeast host, an MFα1 leader-coding sequence is directly linked to a gene such as a cDNA coding for a desired mature foreign protein, and the resulting chimeric DNA is put under the control of a promoter which functions in the used yeast host. In an embodiment of the present invention for the secretion of HSA, a 3'-terminal portion of a natural MFα1 leader-coding sequence was modified, as described in Example 19, to promote the construction of recombinant DNA. In this embodiment, the Xho I cohesive end is provided upstream of the N-terminal Met codon, and the MFα1 leader is inserted to a vector via that cohesive end. Moreover, a C-terminal Arg is encoded by a codon CGC, which provides a Cla I site at a 3'-terminus of the MFα1 leader. This Cla I site is used to link the MFα1 leader to a 5'-terminus of the HSA gene.

Signal peptide of yeast acid phosphatase

Where HSA is expressed as a precursor protein comprising a prepro sequence and mature HSA, which precursor protein is cleaved by a yeast cell processing system to form a mature protein, two correct processing steps are necessary. Since the above-mentioned processing is carried out by a yeast processing system, it is assumed that a leader sequence of a yeast protein, such as an invertase, acid phosphatase or MFα1 protein is more preferable than a leader sequence of HSA, for an efficient and correct processing. Moreover, if HSA is expressed in a form of a preprotein consisting of a signal sequence and mature HSA, instead of a preproprotein consisting of a prepro sequence and mature HSA, only one processing step is necessary to provide a mature HSA, resulting in correct and efficient processing.

Accordingly, any signal sequence of any protein secreted by yeast can be used. According to the present invention, a signal peptide of acid phosphatase, which is well known as a periplasmic protein is used. The acid phosphatase is synthesized in the form of preprotein in a yeast cell, cleaved by a signal peptidase at the endoplasmic reticulum, and transferred to the periplasmic space by passing through the plasma membrane. A DNA coding for the signal peptide of acid phosphatase can be chemically synthesized, and the synthesized DNA linked to a cDNA coding for HSA. An embodiment of the signal peptide is described in Example 29.

C. Gene for desired protein

A gene (cDNA) coding for HSA was cloned, and its nucleotide sequence as well as an amino acid sequence assumed from the nucleotide sequence has been disclosed in Japanese Patent Application No. 63-037453. Accordingly, in the present invention, plasmid PUC.HSA.CH and the like containing a gene for HSA can be used as a gene source of the HSA gene. Note, a process for the construction of the plasmid PUC.HSA.CH is described in Reference Examples 1 and 2.

The above-mentioned chimeric leader sequence comprising an N-terminal portion which readily forms an α-helix and a C-terminal portion which provides a processing site, is novel, and the present invention includes any expression system which comprises the chimeric leader sequence. Structural genes which can be linked with the chimeric leader sequence include those coding for interferons, interleukins, granulocyte macrophage colony stimulating factor, prochymosin, endoglucanase I, α-amylase, epidermal growth factor, β-endorphin, calcitonin, somatomedin C, insulin, thrombin inhibitors, hirudins, and the like.

Structural genes coding for these proteins are available as cDNA, synthetic polynucleotide or genomic DNAs, according to conventional procedures.

D. Poly A sequence and AATAAA signal

It has been reported that a poly A sequence and an AATAAA signal present downstream of a 3'-terminus of a coding sequence function to stabilize the mRNA of a eukaryote (Bergmann and Brawerman, Biochemistry, 16, 259–264, 1977; Huez et al., Proc. Natl. Acad. Sci. U.S.A., 78, 908–911, 981). Accordingly, in a preferred embodiment of the present invention, a poly A sequence and AATAAA signal are provided downstream of the HSA cDNA. As the poly A sequence and AATAAA signal, those naturally linked to the HSA structural gene can be used. The HSA gene containing these sequences has been cloned, and is disclosed in Japanese Patent Application No. 63-037453. As a source of these sequences, for example, λgt11 (HSA-IA) can be used, the construction process of which is described in Reference Example 1.

E. Promoter

In the present invention, any promoter which can function in a yeast cell can be used, but a constitutive promoter rather than an inducible promoter is preferably used. Where an inducible promoter is used, in some cases, HSA is rapidly accumulated in the yeast cell by the induction, resulting in the formation of intermolecular disulfide bonds providing HSA molecules having secondary structures different from that of natural HSA.

Constitutive or weakly inducible yeast promoters which exhibit a strong promoter activity include alcohol dehydrogenase (ADH I) promoter, glycelaldehyde-3-phosphatate dehydrogenase (GAP) promoter, and phosphoglycerate kinase (PGK) promoter. Among these, the ADH I promoter is preferably used.

A nucleotide sequence of about 2,100 bp including a yeast ADH I gene (ADC 1) has been determined and comprises, in addition to an about 1,100 nucleotide sequence coding for ADH I, a 5'-non-coding sequence of about 750 bp and a 3'-non-coding sequence of about 320 bp (Bennetzen, J. and Hall, B., J. Biol. Chem. 257, 3018–3025, 1982). The Goldberg-Hogness box (TATA box), which is believed to be a sequence recognized by RNA polymerase, is positioned 128 bp upstream from translation start codon ATG, and the ADH I promoter function is not lost by a deletion of a region upstream of the Sph I site present at −410 (Beier and Young, Nature 300, 724–728, 1982). The transcript from the ADH I promoter usually comprises at least 1% of the total poly (A) RNA in yeast (Ammerer, G., Methods Enzymol. 101, 192–201, 1983).

F. Terminator

It has been reported that "Read-through" during the transcription reduces the amount of gene product (Zaret, K. S. and Sherman, F., Cell, 28, 563–573, 1982). To prevent this, a terminator is preferably provided downstream of a structural gene to be expressed. For example, a PGK promoter/terminator sandwich vector is used for the expression of calf chymosin and provides an expression in an amount of up to ten times higher than that when a terminator was not used (Mellor et al., Gene, 24, 1–14, 1983). A terminator derived from any gene can be used for this purpose. For example, a terminator of a TRP5 (tryptophan synthesizing enzyme) gene or of a CYC 1 (iso-1-cytochrome C) gene can be used. Where a strong promoter is used, a strong terminator is preferably used to effectively prevent the "read-through".

Accordingly, in the present invention, a strong terminator such as ADH I terminator, GAP terminator or the like is preferably used.

G. Vector element

In addition to the above-mentioned components of a vector which directly participates in the expression, the present expression plasmid must contain a replication origin and a marker gene for a yeast host. A yeast replication origin is, for example, a replication origin of 2 μm plasmid DNA. As marker genes, conventional marker genes such as genes which confer a drug resistance on the host, genes which complement the auxotrophy of a host, and the like, may be used. Moreover, since the intermediary plasmids have to be amplified in the course of construction of a finally desired recombinant plasmid in *E. coli* host, those plasmids are preferably shuttle plasmids which additionally contain a replication origin and a selective marker gene. As a shuttle vector satisfying the above-mentioned requirement, plasmid pJDB207 or the like is commercially available. The plasmid pJDB207 contains, as a yeast marker gene, a LEU2 gene coding for β-isopropylmalate dehydrogenase.

H. Expression plasmid

Accordingly, in a preferable embodiment of the present plasmid, a promoter, leader sequence, HSA structural gene, poly A sequence, and a terminator are inserted, in this order, to a shuttle vector comprising a replication origin and a selective marker gene for a yeast host, as well as a replication origin and a selective marker gene for an *E. coli* host.

2. Transformation

The transformation of the yeast host with the present plasmids is carried out by a conventional procedure. Details of this procedure are given in the Examples.

3. Recovery of desired protein

The yeast host transformed with the present plasmid is cultured by a conventional procedure used for the culturing of yeast. For example, a complete medium such as YPD, and an incomplete synthetic medium such as an SD medium supplemented with 1% yeast extract.

According to the present invention, in many cases HSA produced in yeast cells is extracellularly secreted. The HSA secreted in a culture broth can be recovered and purified, by various conventional processes. For example, differential precipitation using ethanol, acetone, ammonium sulfate or the like, concentration and partial purification by isoelectric-focusing, ultrafiltration or the like, and final purification using various chromatographies alone or in combination.

4. Advantages of the invention

Where a prepro sequence is naturally linked to HSA, the HSA is extracellularly secreted in a form of a mature HSA. Moreover, a cassette comprising a DNA sequence encoding the prepro sequence and HSA cDNA can be inserted to an appropriate expression vector, which may be then transferred into an appropriate host other than yeast, for example mammalian cells, to produce mature HSA. By using a prepro peptide-encoding DNA sequence comprising codons frequently used by yeast, an efficient expression is most likely to be obtained.

Where a chimeric leader sequence comprising an N-terminal portion which readily forms an α-helix and an C-terminal portion which corresponds to a processing portion of a leader sequence of a protein naturally produced by a host is used, the leader sequence easily penetrates into the membrane, resulting in an efficient transport of a desired protein, and the precursor protein can be correctly cleaved by a one step process to provide a correct mature protein.

Where an MFα1 leader sequence is used, an efficient cutting of the prepro peptide is ensured because the MFα1 leader peptide is that of a protein naturally produced in a yeast cell. Moreover, since mature HSA is preferentially secreted, leaving prepro HSA in the yeast cell, the mature HSA can be easily recovered and purified from a culture supernatant without contamination of the prepro HSA.

Where a signal peptide of an acid phosphatase is used, a correctly processed mature HSA is efficiently secreted. This mature HSA can be easily recovered and purified without contamination of the pre HSA. On the other hand, a large amount of insoluble protein which is reactive with an anti-HSA antibody can be obtained. This insoluble protein is considered to be a precursor protein comprising a PHO5 signal peptide and HSA, and this precursor protein can be recovered from yeast cells, and processed in vitro by a signal peptidase derived from yeast, *E. coli*, or mammalian cells.

EXAMPLES

The present invention will now be further illustrated by, but is by no means limited to, the following examples.

In the Examples, enzyme reactions were carried out under the following conditions:

Digestion of DNA For digention with EcoR I (Nippon Gene; 12 units/μl), Cla I (New England Biolabs; 5 units/μl), Hind III (Nippon Gene; 12 units/μl), Xho I (Takara Shuzo; 12 units/μl), or BamH I (Nippon Gene; 35 units/μl), DNA 1 μg, enzyme 1 μl and 10×EcoR I buffer (1M Tris-HCl, pH 7.5, 100 mM $MgCl_2$, 500 mM NaCl) 3 μl was mixed and sterile distilled water was added to make up to 30 μl, and a reaction was carried out at 37° C. for one hour. For Sal I (Nippon Gene; 15 units/μl), Pst I (Nippon Gene; 20 units/μl), Xba I (Nippon Gene; 15 units/μl) and BstE II (Nippon Gene), a buffer containing 100 mM Tris-HCl (pH 7.5), 70 mM $MgCl_2$, 1.75M NaCl, 70 mM 2-mercaptoethanol, 2 mM EDTA and 0.1% calf selum albumin was used. For Sal I, Pst I and Xba I, a reaction was carried out at 37° C. for one hour. For BstE II, a reaction was carried out at 60° C. for one hour. For Msp I (Hpa II) (Nippon Gene; 12 units/μl), a buffer containing 100 mM Tris-HCl (pH 7.5), 100 mM $MgCl_2$ and 60 mM NaCl was used, and for Sma I (Nippon Gene; 15 units/μl), a buffer containing 200 mM KCl, 60 mM Tris-HCl (pH 7.9) and 60 mM $MgCl_2$ was used.

Bacterial alkaline phosphatase treatment

To DNA 1 μg, EcoR I 1 μg, Hind III 1 μg, and 10×EcoR I buffer 2 μl, was added sterile distilled water to make up to 20 μl, and after incubation at 37° C. for one hour, the mixture was heated at 90° C. for 5 minutes to inactivate the enzymes. Next, sterile distilled water 38 μl and bacterial alkaline phosphatase 2 μl (0.5 unit/μl; Takara Shuzo) were added, and after incubation at 37° C. for one hour, phenol extraction and ethanol precipitation were carried out.

T4 DNA ligase treatment

For example, sterile distilled water 30 μl was added to vector DNA 1 μg, DNA fragment in an amount equivalent to the vector DNA, 10×ligase buffer (660 mM Tris-HCl, [pH 7.5], 66 mM $MgCl_2$, 100 mM dithiothreitol and 1 mM ATP) 3 μl and T4 DNA ligase (about 400 units/μl; Takara Shuzo) 1 μl, and the mixture was incubated overnight at 16° C.

5'-phosphorylation of synthetic fragment using T4 polynucleotide kinase

About 30 pmoles of DNA fragment were treated with 6 units of T4 polynucleotide kinase in a buffer containing 50 mM Tris-HCl (pH 7.0), 10 mM MgCl$_2$, 5 mM dithiothreitol, and 0.2 mM ATP, and 37° C. for 60 minutes. The solutions containing a phosphorylated fragment were mixed (total volume, 100 μl), and the mixture was allowed to stand in a water bath of 100° C. for 5 minutes. The reaction mixture was then allowed to cool to room temperature to anneal the fragments. Then 2 μl of T4 DNA ligase was added to the mixture and incubation was carried out overnight at 16° C. to ligate the fragment and form a double-stranded fragment.

*E. coli* DNA polymerase I reaction

To DNA 1 μg, DNA polymerase I (Klenow fragment, Takara Shuzo, 3.5 units/μl) 1 μl, 1 mM dXTP (dATP, dGTP, dCTP, TTP) 1 μl, and 10× buffer (70 mM Tris-HCl, pH 7.5, 1 mM EDTA, 200 mM NaCl and 70 mM MgCl$_2$) 3 μl was added sterile distilled water to make up to 30 μl, and the mixture was incubated at 37° C. for 30 minutes.

Labeling of probe

Ten micro liters of a buffer containing synthetic DNA 1 μg, γr-$^{32}$P-ATP aqueous solution (3000 Ci/mmol) 50 μCi, 50 mM Tris-HCl (pH 7.5), 10 mM MgCl$_2$, 5 mM DTT and 10 units of T4 polynucleotide kinase (Takara Shuzo) was incubated for one hour at 37° C., and unreacted nucleotides were removed using a Nick-column (Pharmacia), according to the protocol supplied by the maker, to obtain $^{32}$P-labeled DNA (1×10$^8$ cpm/1 μg DNA/400 μl).

Hybridization

A membrane on which DNA had been fixed was incubated in 10 ml of a hybridization solution (6×SSC (1×SSC= 0.15M NaCl, 0.015M sodium citrate, pH 7.0), 5×Denhardt's solution (0.1% calf serum albumin, 0.1% Ficoll, 0.1% polyvinyl pyrrolidone), 0.5% SDS, denatured salmon sperm DNA 100 μg] at 42° C. for 3 hours. After the solution was discarded, 10 ml of a hybridization solution containing 1×10$^6$ cpm/ml was added to the membrane, and incubation was carried out for 3 minutes at 80° C., followed by incubation overnight at 42° C. After the solution was discarded, the membrane was washed with 2×SSC at room temperature for 5 minutes and then with 2×SSC at 60° C. for 30 minutes.

Note, where a plasmid was enzymatically constructed the reaction mixture was used to transform *E. coli* HB101 by a conventional procedure, transformants were selected by an appropriate method depending on the *E. coli* marker gene used, and desired plasmids were extracted from the transformants by, for example, a minipreparation method, and analyzed by restriction cleavage followed by electrophoretic analysis (see, Maniatis, T. Fritsch, E. F. and Sambrook, J., Molecular cloning A Laboratory Manual Cold Spring Harbor Laboratory, 1982). Next, the selected clone was cultured and plasmid DNA was extracted from the cultured cells, and if necessary, the plasmid was amplified and recovered. This general process was done, if necessary, during the construction.

Example 1

Synthesis of DNA codinq for prepro sequence of HSA

The following four nucleotides:

1. AATTCATGAAGTGGGT-TACTTTCATCTCTTTGTTGTT
2. AGAACAAGAACAACAAAGAGATGAAAG-TAACCCACTTCATG
3. CTTGTTCTCTTCTGCTTACTCTAGAGGT-GTTTTCAGACG
4. CGCGTCTGAAAACACCTCTAGAGTAAG-CAGAAG were synthesized by the phosphoamidite method described by Matteucci, M. D. and Caruthers, M. H., Tetrahedron Letters, 21, 719 (1980), using an automatic DNA synthesizer (Applied Bio-systems Model 380D). The oligonucleotides were phosphorylated at their 5'-termini using T4 polynucleotide kinase, annealed, and ligated using T4 DNA ligase to form a double-stranded DNA coding for a prepro sequence of HSA. This double-stranded DNA had the structure as described above.

Example 2

Ligation of synthetic DNA coding for prepro sequence of HSA with cDNA coding for HSA
(FIG. 1)

Plasmid pUC-HSA-CH containing HSA cDNA (Reference Example 2) was double-digested with restriction enzymes EcoR I and Cla I to obtain a larger fragment, which was then ligated with the above-mentioned synthetic DNA using T4 DNA ligase to construct plasmid pUC-HSA-EH. The plasmid pUC-HSA-EH was cleaved by EcoR I, 5'-dephosphorylated by bacterial alkaline phosphatase, and re-circularized with an Xho I linker having the following sequence:

5'-AATTCTCGAG GAGCTCTTAA-5' containing an Xho I-recognition site, to form plasmid pUC-X-HSA.

Example 3

Insertion of poly A sequence and AATAAA signal
(FIG. 1)

Phage λgt 11 (HSA-1A) containing a 3'-terminal region of cDNA coding for HSA (Reference Example 1, FIG. 8) was digested with EcoR I to obtain a DNA fragment containing HSA cDNA, and this fragment was ligated with plasmid pUC 18, which had been cleaved with EcoR I, to obtain plasmid pUC-HSA-I'. The plasmid pUC-HSA-I' was cleaved with Hind III to obtain a smaller fragment containing an HSA poly A sequence and AATAAA signal, and this fragment was ligated with pUC-X-HSA which had been linearized by Hind III digestion and 5'-dephosphorylated by alkaline phosphatase to construct plasmid pUC-X-HSA-A.

Example 4

Figure 2:
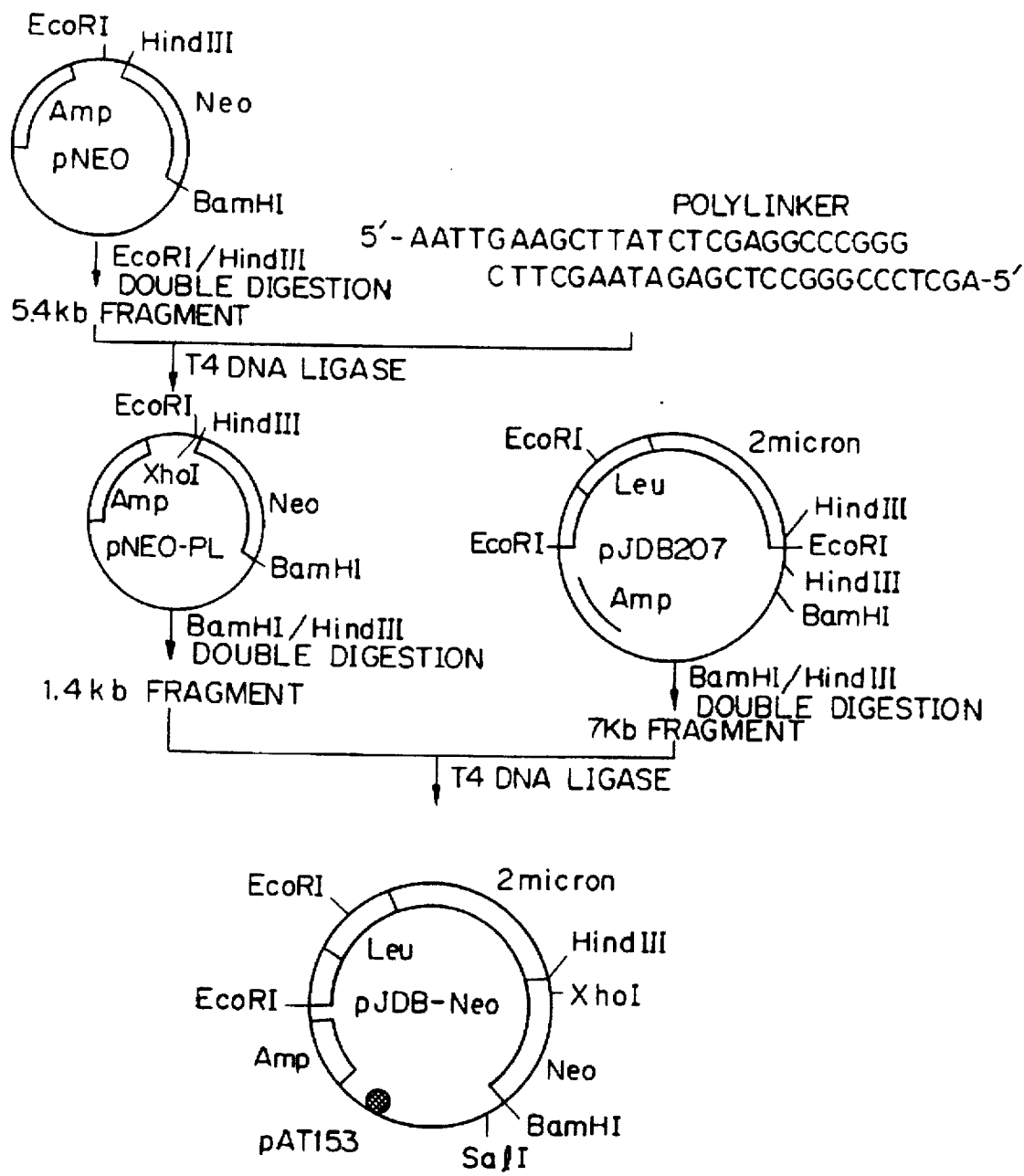
FIG. 2 shows a process for the construction of plasmid pJDB-NeO.

Construction of plasmid pJDB-NeO (FIG. 2)

As a basic *E. coli*/yeast shuttle vector, a commercially available plasmid pJDB207 (Amersham) was used. As a source of the Neo [aminoglucoside 3'-phosphotransferase (II)] gene, plasmid pNEO (Pharmacia) was used. The plasmid PNEO was double-digested with Hind III and EcoR I to obtain a larger fragment. Next, a double-stranded oligonucleotide having the following sequence:

```
  EcoR I                    Hind III
5'-AATTGAAGCTTATCTCGAGGCCCGGG
        CTTCGAATAGAGCTCCGGGCCCTCGA-5'
``` was ligated with the above-mentioned larger fragment from pNEO, using T4 DNA ligase, to obtain plasmid PNEO-PL. The above-mentioned double-stranded oligonucleotide had, in addition to an EcoR I cohesive end at the 5'-terminus and Hind III end at the 3'-terminus, internal Hind III, Xho I, and Sma I sites. Accordingly, the plasmid pNeO-PL had more than one restriction cleavage site upstream of the Neo gene. Next, the plasmid pNEO-PL was double-digested to obtain a 1.4 kb fragment. Plasmid pJDB207 was double-digested with Hind III and BamH I to obtain a vector fragment containing 2 µm replication origin and a marker gene LEU2, and then these fragments were ligated using T4 DNA ligase to obtain plasmid pJDB-Neo.

Example 5

Figure 3A:
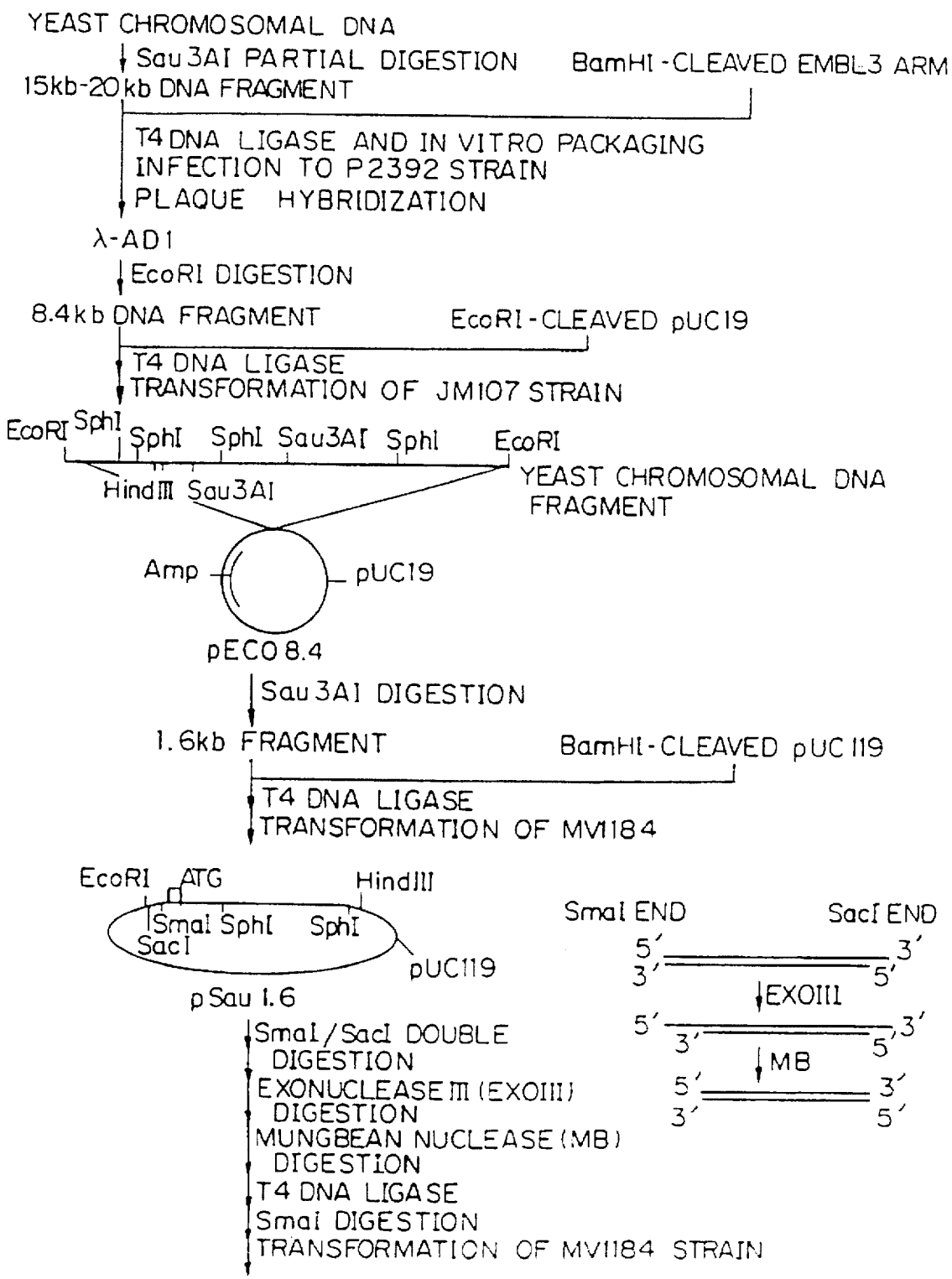
Figure 3B:
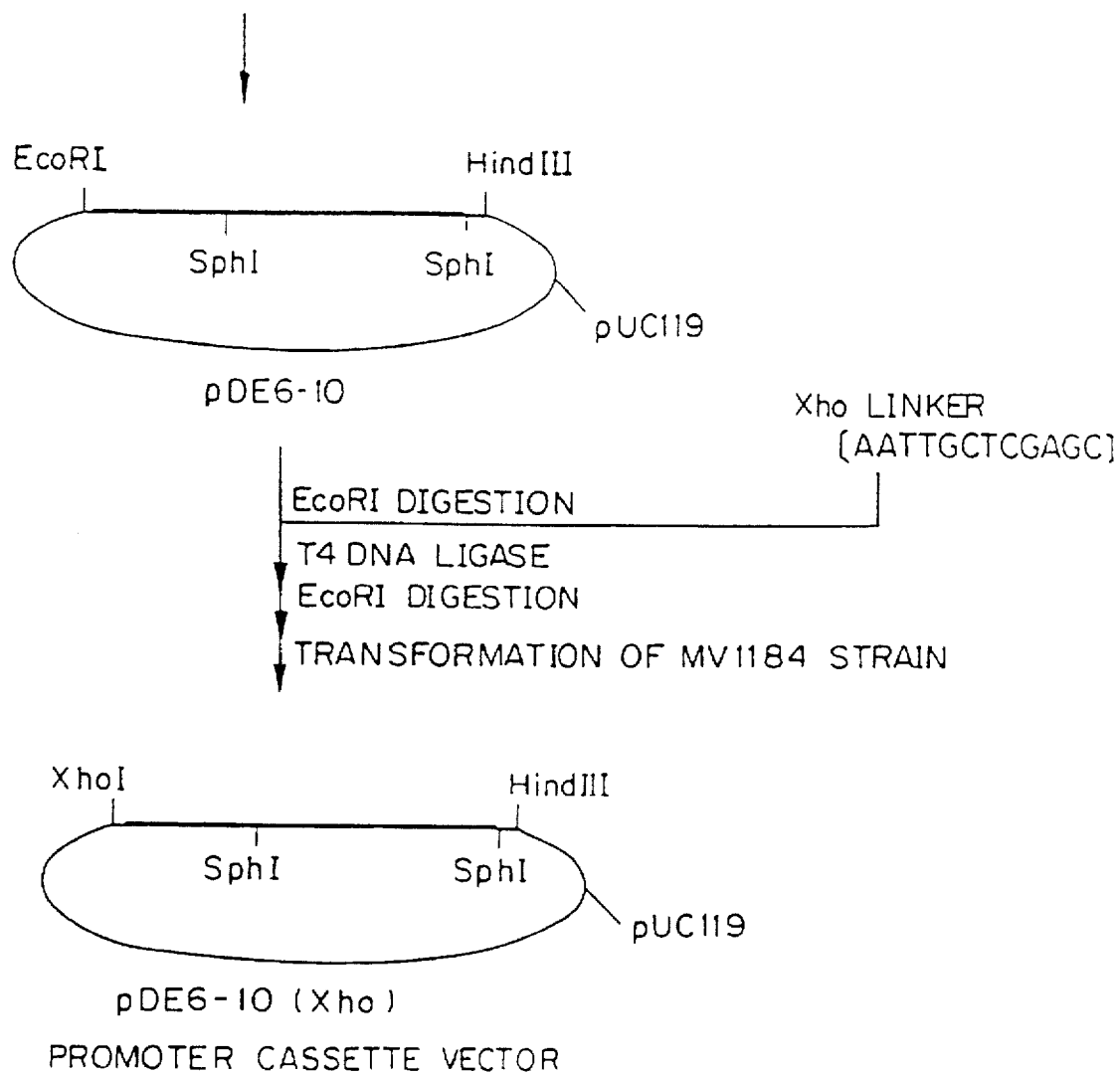

Cloning of yeast ADH I promoter sequence
(FIG. 3)

After, 100 µg of chromosomal DNA of *Saccharomyces serevisiae* AH22 was digested with one unit of Sau 3A I in 200 µl of 50 mM Tris-HCl (pH 7.5), 7 mM $MgCl_2$, 50 mM NaCl, at 37° C. for 15 minutes, 10 µl of 0.5M EDTA (pH 8.0) was added and incubation was carried out at 65° C. for 10 minutes to inactivate the enzyme. Then 5% sucrose-TE (TE=10 mM Tris-HCl, pH 7.5, 1 mM EDTA) and 20% sucrose-TE were used to prepare a density-gradient in a total volume of 12 ml. The above-mentioned reaction mixture was overlaid on this gradient, and the gradient was centrifuged in an SW41 rotor (Beckmann) at 22 Krpm and 16° C. for 15 hours. After the centrifugation, each fraction was subjected to electrophoresis to select a fraction containing 15 kb–20 kb fragments. To the fraction were added 50 µl of 3M sodium acetate (pH 5.2), and then 1 ml of ethanol, and the whole was thoroughly mixed and allowed to stand at –20° C. overnight to precipitate DNA. The precipitated DNA was recovered by centrifugation at 15 Krpm for 5 minutes at 4° C., the precipitate was washed with 70% ethanol and dried under a reduced pressure, so that 5 µg of DNA was obtained.

Then, 1 µg of the DNA thus prepared was mixed with 2 µg of EMBL3 arm (Stratagene) and 350 units of T4 DNA ligase (Takara Shuzo), and incubated overnight at 16° C. in 10 µl of a reaction mixture containing 50 mM Tris-HCl (pH 7.5), 10 mM $MgCl_2$, 10 mM DTT and 1 mM ATP. One minoliter of the reaction mixture was used to carry out in vitro packaging using GIGA-PACK Plus kit (Stratagene, #GP6-P). As a result, $3 \times 10^5$ phages which can infect to *E. coli* P2392 [hsdR 514 (rk⁻, mk⁺), supE44, supF58, lacY I, galK2, galT22, met B1, trpR55, (P2)] were obtained. The phages (1000 pfu) were added to 50 µl of *E. coli* P2392 cells, and after incubation at 37° C. for 20 minutes, the cell mixture in 2.5 ml of L-Top-Agarose [0.7% agarose in LB medium (1% tryptone, 0.5% yeast extract and 1% NaCl)] was spread on L-plate (LB medium +1.5% agar) having a diameter of 90 mm. Five plates were prepared and incubated overnight at 37° C. to allow the formation of plaques. The plates on which plaques were formed were stored at 4° C. for one hour.

A Hybond-N membrane (Amersham) was placed on the agarose layer, and allowed to stand at room temperature for two minutes. The membrane was peeled off from the agarose surface, and put on a 3 MM filter (Whatman) soaked with 0.5N NaOH-1M NaCl, so that a surface of the membrane contacted with the agarose surface was facing upward. After being allowed to stand for 5 minutes, the membrane was then transferred onto a 3 MM filter soaked with 0.5M Tris-HCl (pH 7.2)-1.5M NaCl, and allowed to stand for 5 minutes, and the membrane was washed with 2×SSC and air-dried. The dried membrane was enveloped with SARANWRAP™, and radiated with UV light to fix the DNA on the membrane. The membrane was hybridized with a synthetic probe ADH (5'-ATG TCT ATC CCA GAA ACT CAA AAA GGT GTT-3) corresponding to the nucleotide sequence of an ADCl gene coding for N-terminal 10 amino acids. The membrane was washed and enveloped with SARANWRAP™, and exposed to XAR-5 film (Kodack) using an intensifying screen at –70° C. for 5 hours.

After the development, each of the plaques exhibiting a hybridization signal was picked up with the tip of a Pasteur pipette and added to 50 µl of P2392 cells, the mixture was allowed to stand at 37° C. for 20 minutes, inoculated to 2 ml of LB medium-10 mM $MgSO_4$ and culturing was carried out for 6 hours at 37° C. with shaking. To the culture was added 100 µl of chloroform and the mixture was mixed with a vortex mixer to lyse cells. The lysate was centrifuged at 25,000 rpm for 6 minutes to obtain the supernatant. The supernatant contained some 10 phages. To 800 µl of the supernatant were added 100 µl of 5M NaCl and then 540 µl of isopropanol, and after thorough mixing, the mixture was allowed to stand at –20° C. for 20 minutes. The mixture was then centrifuged to obtain a precipitate, which was washed with 500 µl of 70% ethanol and dissolved in 200 µl of TE.

To the solution were added 1 µl of DN ase I (60 units/µl; Takara Shuzo) and 2 µl of 1M $MgCl_2$, and reaction was carried out at 37° C. for 30 minutes. To the mixture was added 100 µl of TE-saturated phenol, and the mixture was treated with a vortex mixer. The mixture was then centrifuged at 12 Krpm for 5 minutes to obtain an aqueous layer, which was once extracted with phenol/chloroform (1:1). To a resulting aqueous solution were added 20 µl of 3M sodium acetate (pH 5.2) and then 500 µl of ethanol, and the mixture was centrifuged to precipitate DNA. The precipitated DNA was washed with 70% ethanol, dried under a reduced pressure, and dissolved in 50 µl of TE. In this procedure 1 µg of phage DNA was obtained, and to 20 µl of the solution thus obtained were added 2.2 µl of 10×EcoR I buffer (0.5M NaCl, 0.5M tris-HCl, pH 7.5, 70 mM $MgCl_2$) and then 1 µl of EcoR I (5 units/µl; Nippon Gene) and 1 µl of 10 mg/ml RN ase A (Sigma), and incubated for one hour at 37° C. After the reaction, the reaction mixture was subjected to a 0.7% agarose gel electrophoresis, and DNA bands were blotted to a Hybond N membrane by a conventional procedure. The Hybond-N membrane on which DNA was bound was subjected to hybridization under the same condition as for the plaque hybridization described above. Among some of the clones thus obtained the probe was bound to an 8.4 kb EcoR I fragment of the clone λ-AD1. Then 20 µl of the remaining DNA solution was treated with EcoR I and DNA fragments were separated by 0.7% agarose gel electrophoresis, the band containing 8.4 kb EcoR I fragment was cut off, and DNA was separated and purified from the agarose band by a glass powder method (Gene Clean™, Bio-101).

The DNA eluted in 10 µl of TE was ligated with 30 ng of pUC19 in 30 µl of 50 mM Tris-HCl (pH 7.5), 10 mM $MgCl_2$, 10 mM DTT, 1 mM ATP, 350 units of T4 DNA ligase at 16° C. for 2 hours, and 5 µl of the reaction mixture was used to transform *E. coli* JM107. The transformed *E. coli* was plated on L-plate containing 50 μg/ml X-Gal, 5 mM IPTG and 50 μg/ml ampicillin (X-G plate) to form colonies. White clones were picked up and inoculated to 5 ml of LB medium containing 50 μg/ml ampicillin, and grown at 37° C. overnight. DNA was prepared by mini-preparation method, precipitated with ethanol, and dissolved in 50 μl of TE. DNA in 5 μl of TE thus prepared was cleaved with EcoR I (50 mM Tris-HCl, pH 7.5, 7 mM $MgCl_2$, 50 mM NaCl, 1 mg/ml RNase A, 5 units of EcoR I/15 μl), and the reaction mixture was subjected to a 0.7% agarose gel electrophoresis to confirm the insertion of the EcoR I fragment into pUC 19. DNA of the clone pEco 8.4 thus obtained was purified, and 0.5 μg of the DNA was completely digested with Sau 3AI (50 mM Tris-HCl, pH 7.5, 50 mM NaCl, 7 mM $MgCl_2$, 4 units Sau 3AI/15 μl, 37° C., 2 hours), and DNA fragments were separated by a 0.7% agarose gel electrophoresis. Then, 1.6 kb DNA fragment was recovered from the agarose gel into 10 μl of TE using Gene Clean™.

This DNA was ligated with pUC 119 which had been cleaved by BamH I, and 5 μl of the reaction mixture were used to transform *E. coli* MV 1184. The transformed *E. coli* cells were spread on an X-G plate to form colonies. DNAs from white colonies were prepared by mini-preparation method, and analyzed. Then, 5 μg of the DNA were cleaved with 5 units of EcoR I and 5 units of Hind III, or with 6 units of Sph I, and each reaction mixture was analyzed by gel electrophoresis. A clone giving a 1.6 kb DNA fragment in the former cleavage reaction and a 1.0 kb DNA fragment in the latter cleavage reaction were selected, and from the clone pSau 1.6 thus obtained, DNA was prepared and used in the following experiment.

First, 5 μg of the DNA was cleaved with Sma I and Sac I (10 mM Tris-HCl, pH 7.5, 20 mM KCl, 7 mM $MgCl_2$, 20 units of Sma I, 20 units of Sac I/50 μl, 37° C., 2 hours). The reaction mixture was extracted with phenol/chloroform, and DNA was recovered by ethanol precipitation. The DNA precipitate was dissolved in 50 μl of Exo III buffer (50 mM Tris-HCl, pH 8.0, 100 mM NaCl, 5 mM $MgCl_2$, 10 mM 2-mercaptoethanol). 50 μl each of MB buffer (40 mM sodium acetate, pH 4.5, 100 mM NaCl, 2 mM $ZnCl_2$, 10% glycerol) was put into tubes, which were then put on ice. To the above-prepared DNA solution 180 units of Exo III nuclease (Takara Shuzo) was added, and the mixture was incubated at 37° C. From the reaction mixture, 5 μl each of the samples were taken every 30 seconds and poured into the tube containing the MB buffer. After the sampling was finished, the tubes on ice were transferred to incubation at 65° C. for 5 minutes, and cooled to 37° C. To the reaction mixture was added 50 units of mung bean nuclease, and the whole was incubated at 37° C. for 30 minutes. The reaction mixture was extracted with TE-saturated phenol. DNA was recovered by ethanol precipitation and dissolved in 30 μl of TE. Then to 1 μl of the DNA solution were added 2 μl of 10× ligation buffer (500 mM Tris-HCl, pH 7.5, 100 mM $MgCl_2$, 100 mM DTT, 10 mM ATP), and then 16 μl of TE and 1 μl of T4 DNA ligase (350 units/μl), and the mixture was incubated overnight at 16° C. Next, the mixture was incubated at 70° C. for 10 minutes to inactivate ligase, 2 μl of 0.2M KCl and 1 μl of Sma I (10 units/μl) were added, and the whole was incubated at 37° C. for one hour and then at 70° C. for 5 minutes, and put on ice.

The reaction mixture was used to transform *E. coli* MV1184 cells, which were then cultured overnight at 37° C. to form colonies. DNAs were prepared from the colonies, and the clones having a deletion mutation were selected. Next, single-stranded phage DNAs of the clones having the deletion were prepared. The phage DNAs were sequenced using a 7-DEAZA-dideoxy sequencing kit (Takara Shuzo) according to a maker's manual, and the clone pDE 6-10 lacking a region from ATG to an upstream −10 bp position was selected. DNA of pDE 6-10 was prepared, and 1 μg of the DNA was completely digested and dissolved in 100 μl of TE. To 2 μl of this solution 100 ng of Xho linker (AATTGCTCGAGC) were added, and ligation was carried out in 10 μl of reaction mixture at 16° C. for 2 hours. The reaction mixture was incubated at 70° C. for 10 minutes to inactivate the enzyme, and after an addition of 1 μl of 0.5M NaCl and 5 units of EcoR I, incubated at 37° C. for 30 minutes and used to transform *E. coli* MV1184. DNAs were prepared from the resulting colonies, and a clone which was not cleaved with EcoR I but was cleaved with Xho I was selected. In this manner, a promoter cassette vector pDE6-10 (Xho) was obtained.

*Escherichia coli* MV1184/pDE6-10 (Xho) containing the above-mentioned vector pDE6-10 (Xho) was deposited with the Fermentation Research Institute, Agency of Industrial Science and Technology (FRI), 1-3, Higashi 1-chome, Tsukuba-shi, Ibaraki-ken, 305, Japan as FERM P-10311 on Sep. 30, 1988, and transferred to an international deposition under the Budapest Treaty as FERM BP-2589, on Sep. 8, 1989.

Example 6

Figure 4A:
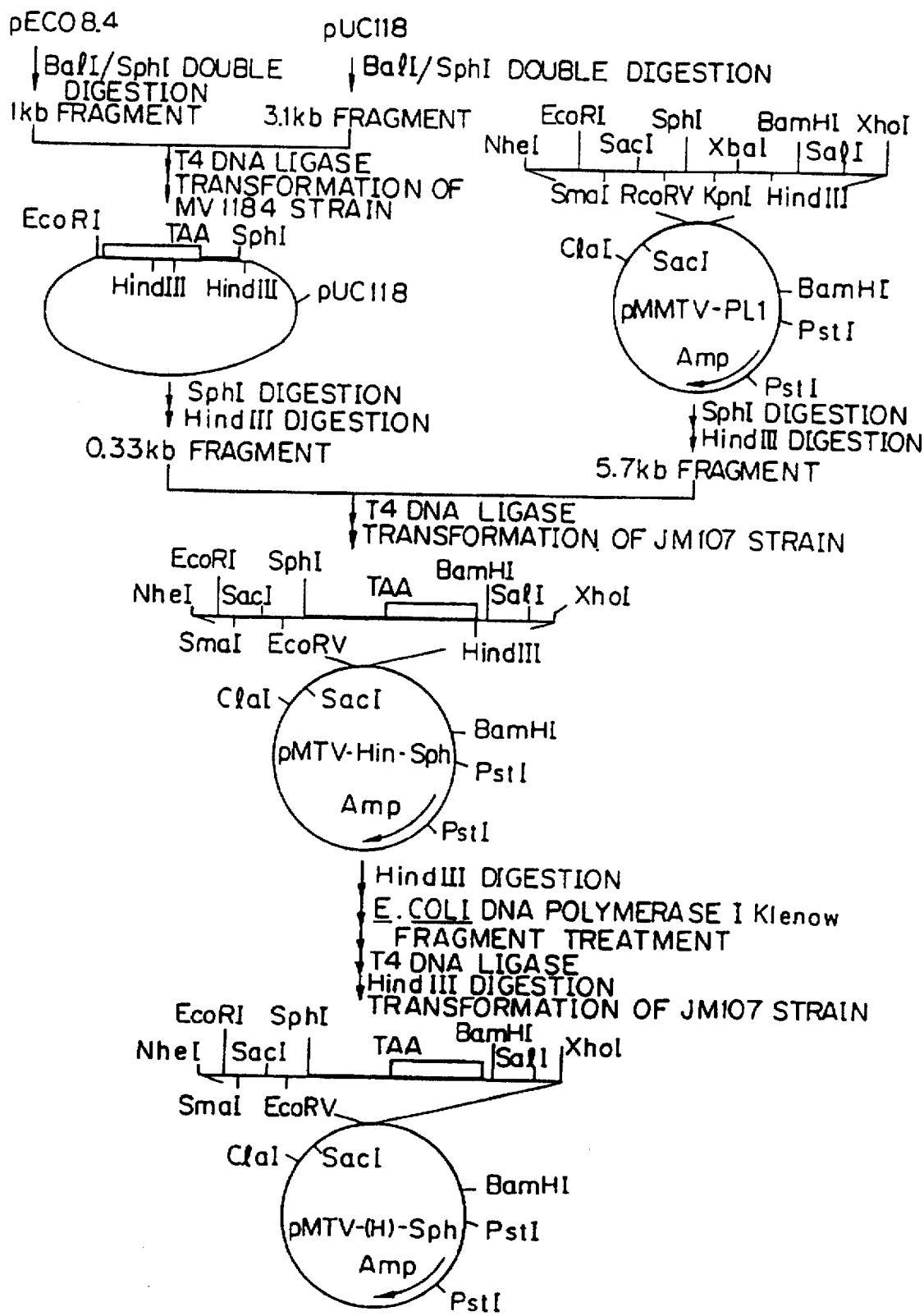
Figure 4B:
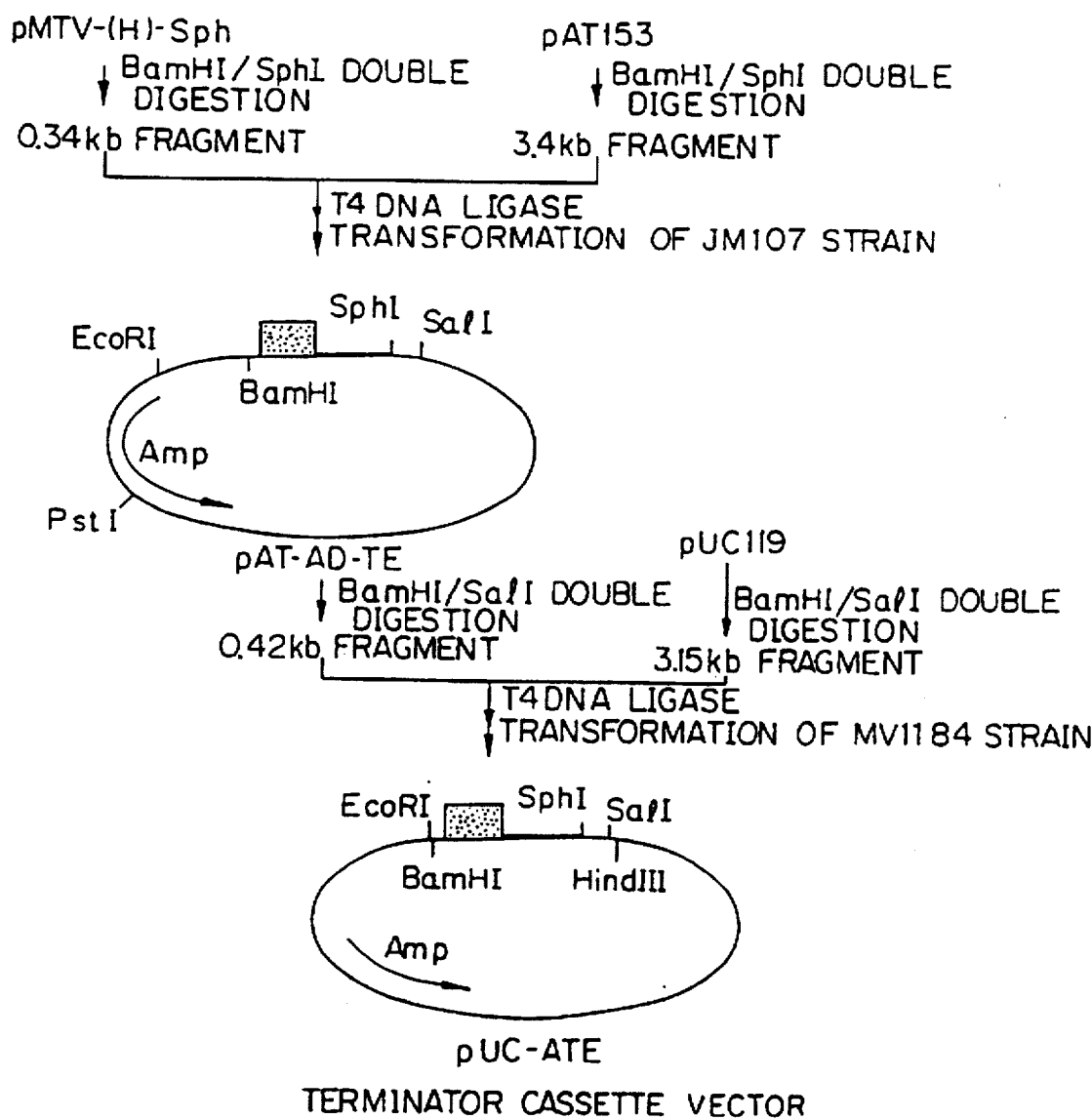

Cloning of yeast ADHI terminator sequence
(FIG. 4)

First, 1 μg of pECO 8.4 was cleaved with 4 units of Bal I in 20 μl of 10 mM tris-HCl (pH 7.5), 7 mM $MgCl_2$ at 37° C. for one hour. Next, to the reaction mixture were added 3 μl of 1M NaCl and 4 units of Sph I, and the mixture was incubated at 37° C. for one hour. The reaction mixture was subjected to a 0.7% agarose gel electrophoresis to separate a 1 kb DNA fragment, which was then extracted by Gene Clean™. The recovered DNA was ligated with pUC 18 which had been cleaved by Sph I and Sma I, and the reaction mixture was used to transform *E. coli* MV1184. DNAs were prepared from the transformants, and a clone containing the fragment was selected. From the clone, DNA was prepared, and 1 μg of the DNA was cleaved with 4 units of Sph I and 12 units of Hind III in 1×EcoR I buffer, and subjected to a 1.2% agarose gel electrophoresis to separate a 0.33 kb DNA fragment, which was then extracted by Gene Clean™. This DNA fragment was ligated in a total reaction volume of 20 μl with 50 ng of the 5.7 kb DNA fragment which had been obtained by double-digestion of plasmid pMMTV-PL1 with Hind III and Sph I.

The reaction mixture was used to transform *E. coli* JM107, which was then allowed to form colonies on an L-plate containing ampicillin (L-amp plate). DNAs were prepared from the colonies, and the inserted DNA was tested by restriction analysis to obtain a clone containing a desired DNA fragment. DNA was prepared from the clone, and 0.5 μg of the DNA was cleaved with Hind III. After incubation at 70° C. for 5 minutes, the reaction mixture was transferred onto ice, and after an addition of 2 units of DNA polymerase (Klenow fragment; Takara Shuzo), incubated at 37° C. for 30 minutes. After removing proteins by phenol/chloroform extraction, DNA was precipitated with ethanol, the DNA was dissolved in 10 μl of 1×ligation buffer, and after the addition of 350 units of T4 DNA ligase, the mixture was incubated overnight at 16° C. The reaction mixture was treated at 70° C. for 10 minutes to inactivate the ligase, and after the addition of 1.2 μl of 0.5M NaCl and 12 units of Hind III, incubated at 37° C. for 30 minutes. The reaction mixture was used to transform *E. coli* JM107. Some colonies formed on an L-amp plate were cultured in L-amp liquid medium (L-amp medium excluding agar), and from the resulting cells, DNAs were prepared and a clone containing plasmid DNA lacking a Hind III site was selected. DNA was prepared from the selected clone, and 0.5 µg of the DNA were cleaved with 4 units of BamH I and 12 units of Sph I in 10 mM Tris-HCl (pH 7.5), 150 mM NaCl and 7 mM MgCl$_2$. Then a 0.34 kb DNA fragment was separated by a 1.4% agarose gel electrophoresis, and recovered in 10 µl of TE by Gene Clean™. This DNA fragment was ligated with a 3.5 kb DNA fragment which has obtained by cleaving 30 ng of pAT153 with BamH I and Sph I.

The reaction mixture was used to transform *E. coli* JM107 to form colonies on an L-amp plate, and some colonies were cultured in L-amp liquid medium. DNAs were prepared from the cultured cells, and a clone giving a 0.42 kb DNA fragment by BamH I/Sal I double digestion was selected. Then 0.5 µg of the cloned DNA thus obtained was cleaved with BamH I and Sal I, and a 0.42 kb DNA fragment was separated by a 1.4% agarose gel electrophoresis and recovered in 5 µl of TE by Gene Clean™. This DNA fragment was ligated with 10 ng of pUC119 which had been cleaved with BamH I and Sal I, and the reaction mixture was used to transform *E. coli* MV1184, which was then plated on X-G plate to form colonies. DNAs were prepared from the resulting white colonies, and a clone which contained the DNA fragment was obtained. This terminator cassette vector was designated PUC-ATE.

*Escherichia coli* MV1184 (pUC-ATE) containing the vector PUC-ATE was deposited with the FRI as FERM P-10310 on Sep. 30, 1988, and transferred to an international deposition as FERM BP-2588, on Sep. 8, 1989.

Example 7

Figure 5:
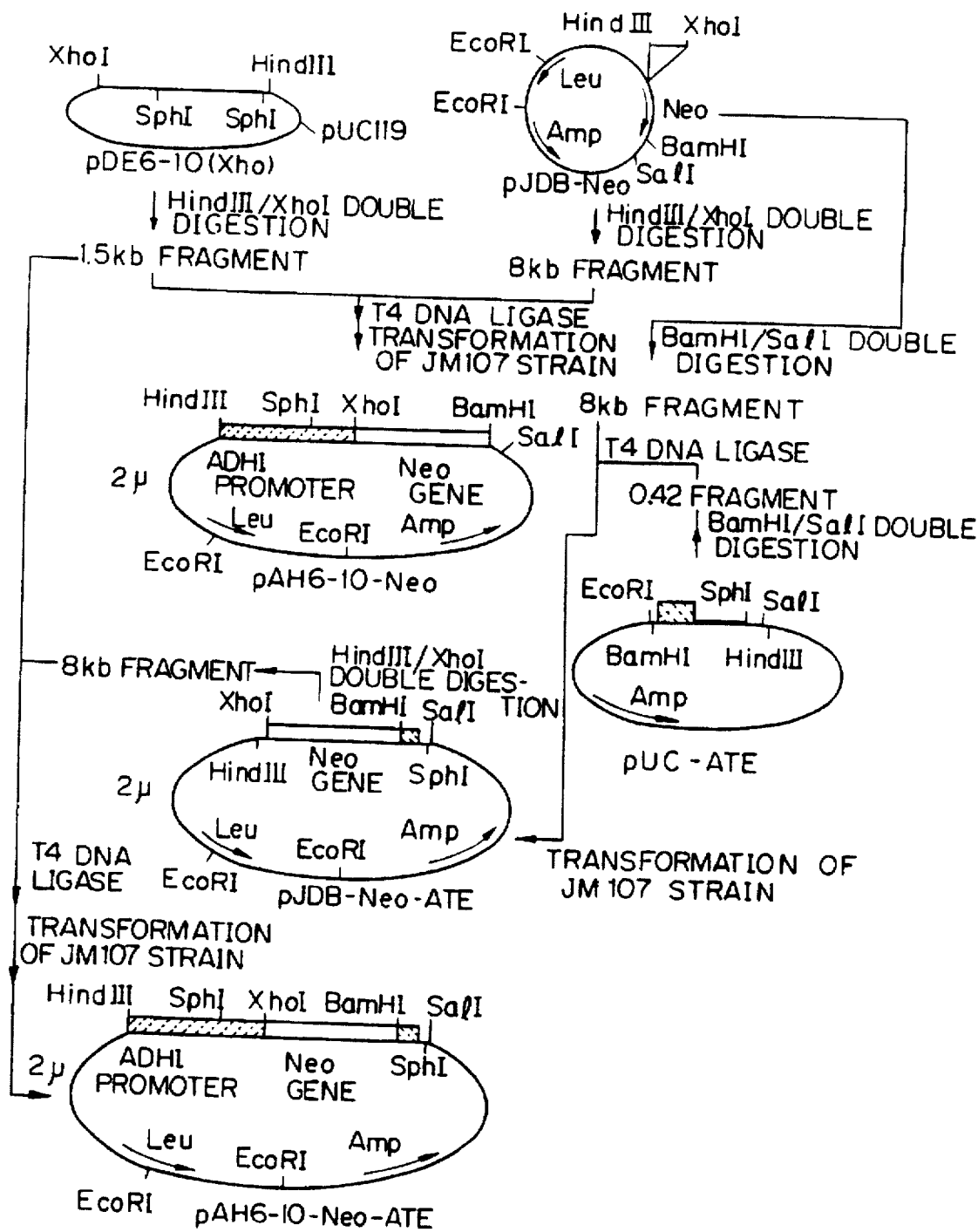
FIG. 5 represents a process for the construction of yeast expression vector (ADHI sandwich vector) pAH6-10-Neo-ATE.

Construction of yeast expression vector (sandwich vector) (FIG. 5)

The promoter cassette vector pDE6-10 (Xho) (0.5 µg) was cleaved with Hind III and Xho I, and a 1.6 kb DNA fragment was isolated by a 0.7% agarose gel electrophoresis. On the other hand, 0.5 µg of pJDB-Neo was cleaved with Hind III and Xho I, and an 8 kb DNA fragment was isolated. Both DNA fragments were ligated together and the ligation products were used to transform *E. coli* JM107, resulting in the formation of ampicillin resistant colonies. DNAs were obtained from the colonies, and a clone having a desired plasmid designated as pAH6-10-Neo was confirmed. Plasmid PJDB-Neo (0.5 µg) was cleaved with Bam HI and SalI to obtain a DNA fragment of about 8 kb in size. On the other hand, 1 µg of PUC-ATE was digested with BamHI and SalI to obtain a 0.42 kb fragment. Both the fragments were ligated and the ligation product was used to transform *E. coli* JM107. DNAs were prepared from ampicillin-resistant clones and analyzed to confirm that the clone contained a desired plasmid designated as PJDB-Neo-ATE. Then 0.5 µg of the plasmid pJDB-Neo-ATE was cleaved with Hind III and Xho I to obtain a DNA fragment of about 8 kb in size. On the other hand, from pDE-6-10 (Xho) a 1.6 kb Hind III-Xho I fragment was recovered. Both fragments were ligated, and the resulting plasmids were used to transform *E. coli* JM107. DNAs from ampicillin resistant colonies were tested to find a clone having a desired plasmid designated as pAH6-10-Neo-ATE.

*Escherichia coli* JM107/pAH6-10-Neo-ATE, containing the above-prepared vector, was deposited with the FRI as FERM P-10309 on Sep. 30, 1988, and transferred to an international deposition as FERM BP-2587 on Sep. 8, 1989.

Example 8

Figure 6:
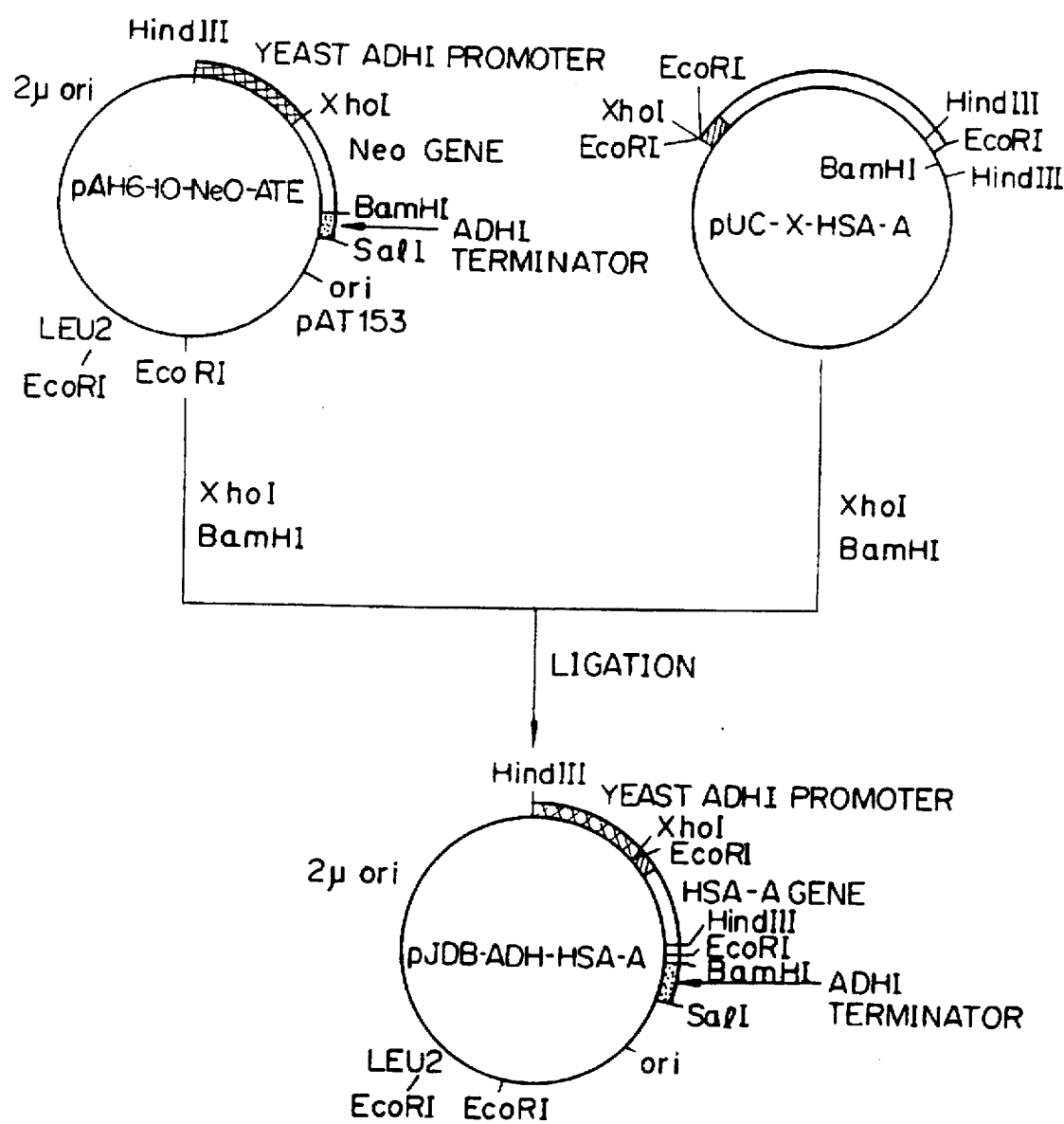
FIG. 6 shows a process for the construction of expression plasmid pJDB-ADH-HSA-A.

Construction of expression plasmid (FIG. 6)

The plasmid pAH6-10-Neo-ATE prepared as described above, which had an ADH promoter upstream of the Neo gene and an ADH terminator downstream of the Neo gene, was double-digested with Xho I and BamH I to obtain a vector fragment lacking the Neo gene. On the other hand, plasmid pUC-X-HSA-A containing HSA cDNA (Example 3) was double-digested with Xho I and BamH I to obtain a DNA fragment containing a cDNA coding for prepro HSA comprising an artificial leader sequence, and poly A sequence. These DNA fragments were ligated to construct an expression plasmid pJDB-ADH-HSA-A.

Example 9

Transformation of yeast host with expression plasmid

Transformation of yeast host cells with expression plasmids was carried out by a slight modification of the KUR method described by H. Hashimoto and H. Kimura (Hakko To Kogyo, 43, 630–637, 1985). First, 0.1 ml of an overnight preculture of *Saccharomyces cerevisiae* AH22 (MATa, leu 2-3, leu 2-112, his 4-519, Canl) in YPD medium [2% polypeptone (Difco), 1% yeast extract (Difco) and 2% glucose] was inoculated to 5 ml of YPD medium and cultured at 30° C. for about 4 hours with shaking until the turbidity at OD$_{600}$ reached 0.5. The culture was then centrifuged at 4° C. for 5 minutes at 2,000 rpm to collect cells, which were then resuspended in 5.0 ml of 1.0M LiSCN, and 1.5 ml of the suspension were centrifuged at 2,000 rpm for 5 minutes, or at 10,000 rpm for one minute. The cells thus obtained were resuspended in 10 µl of 2M LiSCN and 46 µl of 50% PEG 4000, and to this suspension were added 10 µl of DNA solution (containing 5 to 10 µg of DNA), and the mixture was incubated at 30° C. overnight. To the suspension was added 1 ml of sterile distilled water, and the whole was gently mixed by a vortex mixer. Next, the suspension was centrifuged at 2,000 rpm for 5 minutes, or at 10,000 rpm for one minute, and the collected cells were resuspended in 100 µl of sterile distilled water. The suspension was then spread on a selective a gar plate. [SD medium: 20 µg/ml adenine sulfate, 20 µg/ml arginine hydrochloride, 20 µg/ml methionine, 20 µg/ml histidine hydrochloride, 20 µg/ml tryptophan, 20 µg/ml uracil, 30 µg/ml isoleucine, 30 µg/ml lysine hydrochloride, 30 µg/ml tyrosine, 50 µg/ml phenylalanine, 150 µg/ml valine, 0.15% amino acid-free Yeast Nitrogen Base (Difco), 0.5% ammonium chloride, 2% dextrose and 1.5% agar). The resulting colonies (Leu$^+$) were suspended in 5 ml of SD medium, and cultured at 30° C. for 2 days. The culture was centrifuged at 2,000 rpm for 5 minutes at 4° C. to collect cells, which were then resuspended in 0.5 ml of 1M sorbitol. The suspension was centrifuged to collect cells, which were then re-suspended in 0.5 ml of 1M sorbitol, 0.1% 2-mercaptoethanol and 400 µg/ml Zymolyase-100T (Seikagaku Kogyo). The suspension was incubated at 30° C. for 30 minutes to form spheroplasts which were then centrifuged at 2,000 rpm for 5 minutes. The collected spheroplasts were resuspended in 100 µl of solution I (50 mM glucose, 10 mM Tris-HCl, pH 8.0), and after the addition of 200 µl of solution II (0.2N NaOH, 1% SDS), the suspension was thoroughly mixed and put on ice for 5 minutes. To the suspension were added 150 al of 5M potassium acetate, and the suspension was thoroughly mixed, and after putting on ice for 10 minutes, centrifuged at 15,000 rpm and 4° C. for 5 minutes to obtain a supernatant, which was then transferred to a fresh tube. An equal volume of phenol/chloroform (1:1) was added to the supernatant, and the whole was violently mixed and centrifuged at 12,000 rpm for 5 minutes to obtain an aqueous layer, which was then transferred to a fresh tube. To the aqueous layer were added 750 μl of ethanol, and the mixture was thoroughly mixed by a vortex mixer. The mixture was centrifuged at 15,000 rpm for 5 minutes to obtain a precipitate, to which 0.5 ml of 70% ethanol were added. This mixture was mixed by a vortex mixer, and centrifuged at 15,000 rpm for 5 minutes to obtain a precipitate. The DNA precipitate thus obtained was dried under a reduced pressure and dissolved in 30 μl of TE buffer. The DNA preparation obtained from the AH22 transformants containing plasmid pJDB-ADH-HSA-A was digested with various restriction enzymes such as Hind III, Xho I, EcoR I, BamH I and Sal I, alone or in combination, and the resulting fragments were analyzed by agarose gel electrophoresis and polyacrylamide gel electrophoresis to confirm the structure of the plasmid.

Example 10

Figure 7A:
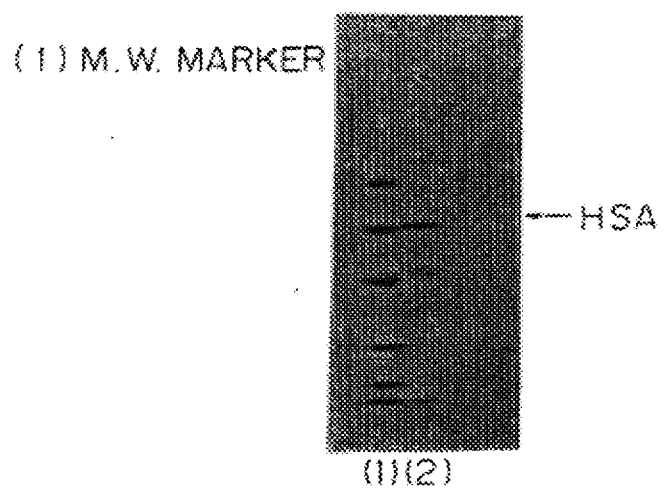
FIGS. 7A-B shows the results of electrophoresis wherein (A) represents mature HSA produced by culturing a transformant AH22 (pJDB-ADH-HSA-A) containing HSA cDNA, separated by an SDS-polyacrylamide gel electrophoresis and stained with Coomassie Brilliant Blue, and (B) represents a corresponding Western blot.
Figure 7B:
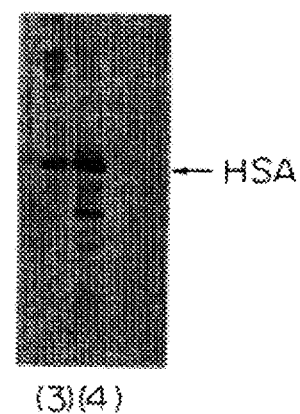

Production of HSA by transformants (FIG. 7)

A single colony formed on an SD (-Leu) plate was suspended in 5.0 ml of fresh SD (-Leu) liquid medium and cultured at 30° C. for 2 days with shaking until an $OD_{600}$ reached about 2.0, then 0.1 ml of the culture was added to 5.0 ml of YPD medium, and cultured at 30° C. for 24 hours until an $OD_{600}$ reached about 3.0. The culture was centrifuged at 5,000 rpm for 10 minutes at 4° C. to obtain a supernatant fraction. To the supernatant fraction was added an equal volume of 99% ethanol, and the whole was mixed and allowed to stand at 4° C. for 30 minutes. Next, the mixture was centrifuged at 12,000 rpm and 4° C. for 10 minutes to obtain a precipitate. The precipitate was dissolved in 100 μl of 1×loading buffer (5% 2-mercaptoethanol, 0.0025% bromophenol blue, 2% SDS, 0.025M Tris-HCl and 8% glycerol), and 10 μl of the solution was applied to an electrophoretic gel [SDS-polyacrylamide gel; 4 to 20% concentration gradient; 84 mm (width)×90 mm (height)×1.0 mm (thickness)]. Electrophoresis was carried out with an eletrophoresis buffer (0.025M Tris-HCl, pH 8.4, 0.192M glycine and 0.1% SDS) at a constant current of 60 mA for 60 minutes. As molecular weight (MW) markers, egg white lysozyme (MW 14,400), soybean trypsin inhibitor (MW 21,500), carbonic anhydrase (MW 31,000), ovalbumin (MW 45,000), bovine serum albumin (MW 66,200), and phosphorylase B (MW 92,500), all obtained from BIO-RAD, were used. After the electrophoresis, proteins in the gel were stained with Coomassie Brilliant Blue, or as described hereinafter, immunologically detected after Western blotting. After the electrophoresis, the separated proteins were transferred to a nitrocellulose filter (BIO-RAD) using a semi-dry blotter (Sartorius). Namely, the filter was soaked in methanol for one hour and then in 25 mM Tris-HCl (pH 10.4)/20% methanol, and attached to an electrophoretic gel. This was sandwiched with filter papers which had been soaked in the above-mentioned buffer, and 0.3M Tris-HCl (pH 10.0) containing 20% methanol and 25 mM Tris-HCl (pH 9.4)/40 mM 6-amino-n-capronic acid, and was applied to the blotter. After applying a constant voltage of 6 V for about 1.5 hours, the filter was washed by shaking it in a solution of 20 mM Tris-HCl (pH 7.5)/500 mM NaCl (TBS) containing 3% gelatin at 37° C. for one hour, and then in TBS/0.05% Tween-20 for 5 minutes. Next, the filter was shaken in 40 ml of a solution containing anti-human serum albumin rabbit antibody (Cappel) which had been diluted 2,000-fold with TBS containing 1% gelatin, at room temperature overnight. The filter was washed with TBS (pH 7.5) containing 0.05% Tween-20 (T-TBS) while shaking. This procedure was once repeated. The filter was then shaken in 40 ml of a solution containing secondary antibody (goat anti-rabbit IgG antibody labeled with horseradish peroxidase; BIO-RAD) which had been diluted 3,000-fold with TBS containing 1% gelatin, for one hour at room temperature. Next, the filter was washed twice with T-TBS for 5 minutes and once with TBS for 5 minutes as described above. The filter was soaked in a mixture of 10 ml methanol containing 30 mg of 4-chloronaphtol, 50 ml TBS and 30 μl of 30% hydrogen peroxide to detect a band corresponding to HSA, and the developing reaction was terminated by diluting with distilled water. The results are set forth in FIG. 7.
In this figure, (A) represents a result of SDS-polyacrylamide gel electrophoresis followed by Coomassie Brilliant Blue staining, wherein the left lane represents molecular weight markers and the right lane represents a result for a sample containing HSA produced and secreted by yeast transformants; and (B) represents a result of SDS-polyacylamide gel electrophoresis followed by Western blotting and binding with an anti-HSA antibody specifically to stain HSA and the fragments thereof, wherein the left lane represents a result for HSA purified from human serum and the right lane represents a result for HSA produced and secreted by yeast transformants.

Example 11

Figure 12:
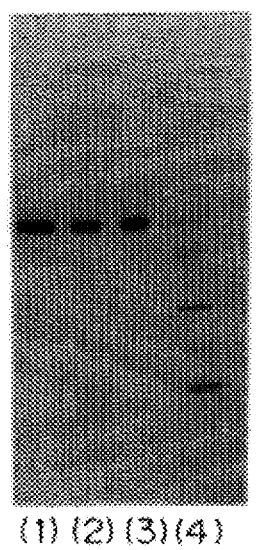
FIG. 12 shows a result of a comparison of molecular weights of HSA produced by yeast transformants and HSA prepared from human serum, obtained by an SDS-polyacrylamide gradient gel electrophoresis.

Biochemical homology between HSA produced by yeast transformants and HSA prepared from human serum (1) Molecular weight A sample of HSA isolated from a yeast culture was reduced with 2-mercaptoethanol, treated with SDS, and applied to a 12%–30% polyacrylamide gradient gel in SDS, and electrophoresis was carried out under the conditions described by Laemmli, U. K., Nature, 227, 680–685, 1970. As molecular weight markers, phosphorylase B (MW 94,000), bovine serum albumin (MW 67,000), ovalbumin (MW 45,000), carbonic anhydrase (MW 31,000), soybean trypsin inhibitor (MW 21,500), and lactoalbumin (MW 14,000) were used. Proteins were detected by Coomassie Brilliant Blue staining. Simultaneously, as a control, commercially available HSA purified from human serum was run, and the mobility of both HSAs were compared. As a result, HSA produced by yeast transformants and HSA derived from human serum exhibited the same mobility, and their molecular weight was 67,000, as shown in FIG. 12.

(2) Electrophoretic properties Native gel electrophoresis

Figure 13:
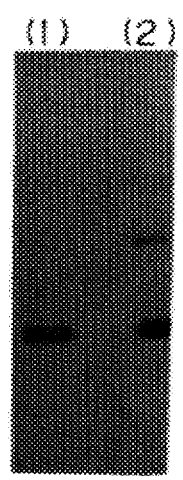
FIG. 13 shows a result of a comparison of HSA produced by yeast transformants and HSA prepared from human serum, obtained by a native polyacrylamide gradient gel electrophoresis.

A sample of HSA isolated from yeast culture was applied to a 12%–30% polyacrylamide gradient gel free from SDS, and electrophoresis was carried out under the conditions as described above but excluding SDS. Protein bands were detected by Coomassie Brilliant Blue staining. Simultaneously, as a control, a commercially available HSA purified from human serum was run, and the electric behavior thereof was compared. In native (excluding SDS) gel electrophoresis, HSA produced by yeast transformants and HSA derived from human serum exhibited the same electrophoretic behavior, as shown in FIG. 13.

Isoelectricfocusing

Figure 14:
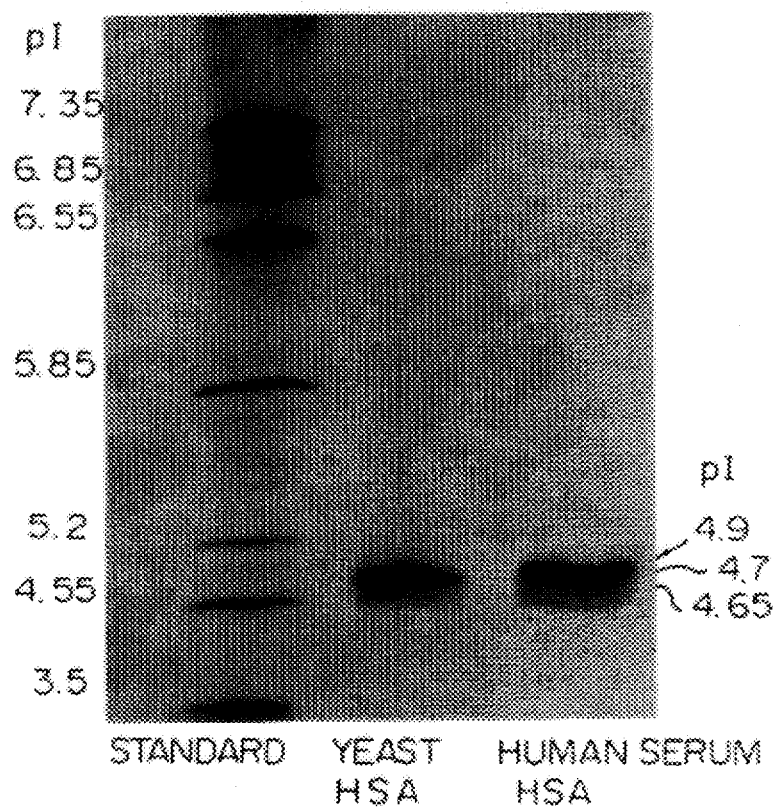
FIG. 14 shows a result of a comparison of HSA produced by yeast transformants and HSA prepared from human serum in isoelectroic focusing.

Isoelectricfocusing was carried out using an Ampholine PAG plate, pH range 3.5–9.5 (LKB) according to the maker's manual. As isoelectric point markers, LKB's PI markers, i.e., C-phycocyanin (pI 4.75, 4.85), azurin (pI 5.65), trifluoroacetylated myoglobin (porcine pI 5.9), myoglobin (porcine pI6.45), myoglobin (horse pI 7.3), myoglobin (whale pI 8.3), and cytocrome C (pI 10.6) were used. HSA produced by yeast transformants exhibited a main band at pI 4.9 and two minor bands at pI 4.7 and 4.65, which were the same as HSA purified from human serum. This result is set forth in FIG. 14.

(3) Immunological properties

Figure 15:
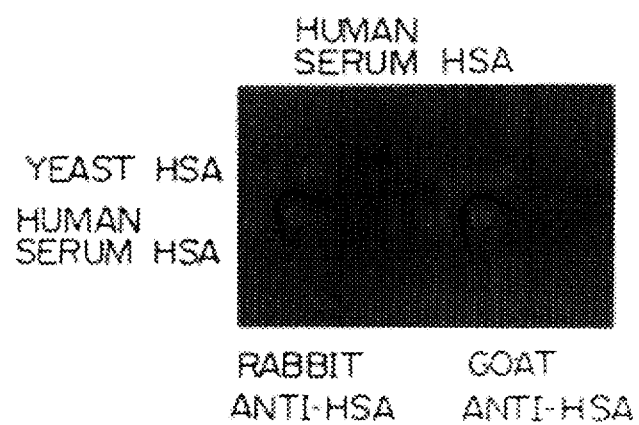
FIG. 15 shows a result of a comparison of HSA produced by yeast transformants and HSA prepared from human serum by the Ouchterlony method.

Immunodifusion was carried out according to a method of Ouchterlony, Ö, Progr. Allergy, 6, 30, 1962. After formation of precipitin lines and deprotenazation with physiological saline, the precipitin lines were stained with Coomassie Brilliant Blue. The antisera used for the immunodiffusion test were rabbit anti-HSA antiserum (Cappel) and goat anti-HSA antiserum (PEL FREEG). Using each serum, a precipitin line by HSA produced by yeast transformats was completely fused with a precipitin line by HSA purified from human serum, revealing the absence of antigenic difference between the HSAs. The result is set forth in FIG. 15.

(4) Determination of N-terminal amino acid sequence

The N-terminal amino acid sequence of HSA produced by yeast transformants was determined using a gas phase protein sequencer 477 A (Applied Biosystems) according to the maker's manual. As a result, an amino acid sequence from the N-terminal Asp to 32nd Gln, which was completely identical with the reported amino acid sequence from the N-terminus to 32nd amino acid of HSA from human serum. Calculating from the recovery of N-terminal amino acids, it was estimated that the HSA preparation tested had an N-terminal homogeneity of at least 93%. In the N-terminal sequence determination, the absence of a prepro or pro HSA due to an incomplete processing was confirmed.

The N-terminal amino acid sequence of HSA produced by yeast transformants was as follows:

|  | 10 |
| --- | --- |
| Asp—Ala—His—Lys—Ser—Glu—Val—Ala—His—Arg— | |
|  | 20 |
| Phe—Lys—Asp—Leu—Gly—Glu—Glu—Asn—Phe—Lys— | |
|  | 30 |
| Ala—Leu—Val—Leu—Ile—Ala—Phe—Ala—Gln—Tyr— Leu—Gln | |

(5) Behavior on HPLC Reverse phase column chromatography

As a high performance liquid chromatography (HLPC) apparatus, an Applied Biosystems 130A separation system equipped with an Aquapore RP-300 column (2.1 mm I.D×30 mm) was used. The column was equilibrated with 0.1% trifluoroacetic acid, and the elution of proteins was carried out with an acetonitrile concentration gradient from 0% to 100% in 0.1% trifluoroacetic acid for 45 minutes at a flow rate of 200 μl/minute.

Under there conditions, HSA produced by yeast transformants provided a single sharp peak having a retention time and shape indistinguishable from those of HSA purified from human serum. Moreover, when these two HSAs were mixed and the mixture was chromatographed on the column, the mixture provided a single sharp peak, indicating that the behavior of these two HSAs on the reverse phase column was completely identical.

Figure 16A:
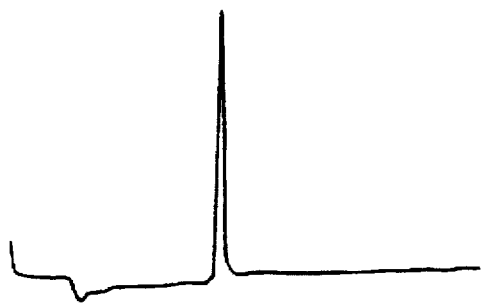
FIGS. 16A-C shows a result of a comparison of HSA produced by yeast transformants and HSA prepared from human serum by reverse phase high performance liquid chromatography (HPLC) wherein A represents HSA from human serum, B represents HSA produced by yeast transformants, C represents the mixture of A and B.
Figure 16B:
Figure 16C:

The result is set forth in FIG. 16. In this figure, A, B, and C represent a result of a reverse phase column chromatography for HSA produced by yeast transformants, HSA derived from human serum, and a mixture thereof, respectively.

Hydroxyapatite chromatography

For HPLC, an SCL-6A, LC-6A series system (Shimazu Seisakusho) equipped with a high separation analytical hydroxyapatite column TAPS-020810 (7.2 mm I.D×10 cm) (Tonen) was used. Elution was carried out with a linear gradient from 10 mM phosphate buffer/0.05% sodium azide to 0.3M phosphate buffer/0.05% sodium azide for 30 minutes at a flow rate of 1 ml/minute. To prepare a sample for the analysis, the supernatant from the culture of yeast transformants was concentrated using DEAE-Sepharose CL-6B, the concentrate was subjected to ammonium sulfate precipitation at 40% saturation to obtain the supernatant, which was then subjected to ammonium sulfate precipitation at 60% saturation to obtain a precipitate. The retention time of HSA produced by yeast transformants was 11.5 minutes, which was identical with that of HSA purified from human serum. Accordingly, again in the behavior on a hydroxyapatite column, the HSAs were in distinguishable.

Figure 17A:
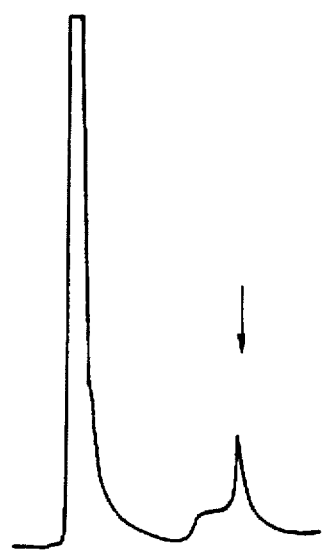
FIGS. 17A-B shows a result of a comparison of HSA (A) produced by yeast transformants and HSA (B) prepared from human serum by hydroxyapatite chromatography.
Figure 17B:
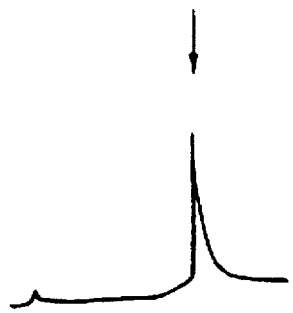

This result is set forth in FIG. 17, wherein A and B represent a result of hydroxyapatite chromatography for a concentrate fraction from yeast culture and HSA purified from human serum, respectively.

Example 12

Figure 18:
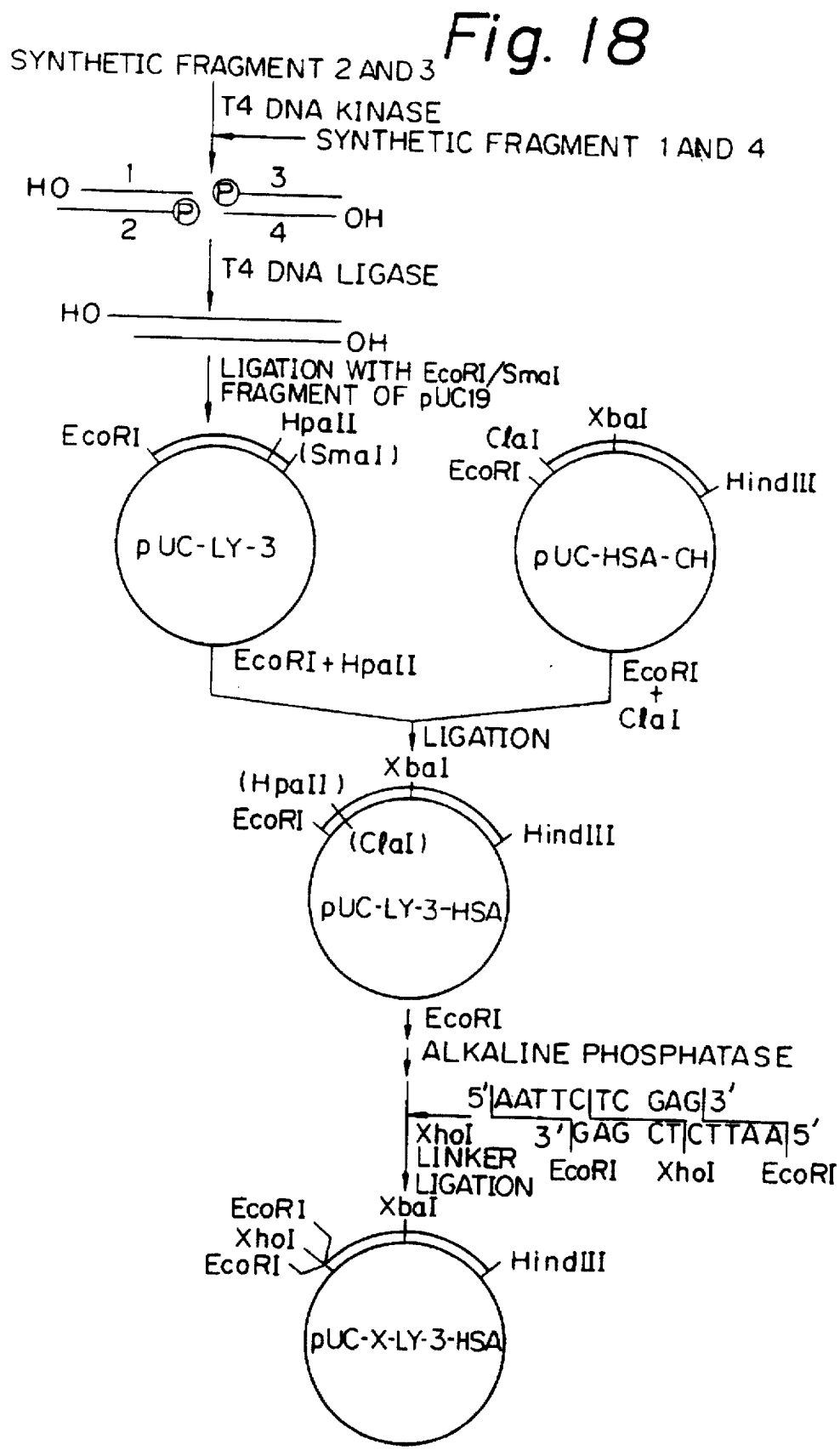
FIG. 18 shows a process for the construction of plasmid pUC-X-LY3-HSA.

Synthesis of DNA coding for chimeric signal peptide (FIG. 18)

A DNA sequence coding for chimeric signal peptide comprising at the N-terminus thereof an amino acid sequence which readily forms an α-helix, and at the C-terminus thereof, an amino acid sequence of a corresponding portion of yeast invertase signal peptide, was designed as follows. For a convenient insertion of the synthetic DNA to a vector, the 5'-terminus of the DNA was an EcoR I cohesive end. Moreover, to allow direct ligation of the synthetic DNA at the 3'-terminus thereof with the 5-terminus of a DNA coding for a desired mature protein, the 3'-terminal nucleotide sequence of the synthetic DNA was selected so that a codon for the C-terminal amino acid alanine of the DNA and an adjacent adapter nucleotide sequence form the Nae I recognition sequence. Note, since the Nae I recognition sequence GCCGGC contains an Hpa II recognition sequence, the synthetic DNA sequence can be ligated with a mature protein gene having a 5'-terminal Hpa II cohesive end.

To construct the DNA coding for the chimeric signal peptide, the following four oligodeoxyribonucleotides were synthesized:

1. 5'-AATTCATGAAGTTGTTGCTCCTCCTTC-TTTTGCTCTT 2. 5'-AGAACAAGAAGAGCAAAAGAAGGAGG-AGCAACAACTTCATG 3. 5'-CTTGTTCTCTGCTAAGATTTCTGCCGGC 4. 5'-GCCGGCAGAAATCTTAGCAG.

The synthetic oligonucleotides 2 and 3 were phosphorylated at their 5-termini using T4 polynucleotide kinase, and mixed with the synthetic oligonucleotides 1 and 4 to be annealed. Next, the annealed mixture was treated with T4 DNA ligase to construct a DNA coding for a full length chimeric signal peptide. The double-stranded DNA thus constructed had the following sequence.

|   | Met | Lys | Leu |   | Leu | Leu |   | Leu | Leu |   | Leu | Leu |
|---|---|---|---|---|---|---|---|---|---|---|---|---|
| 5' AATTC | ATG | AAG | TTG |   | TTG | CTC |   | CTC | CTT |   | CTT | TTG |
| G | TAC | TTC | AAC |   | AAC | GAg |   | GAG | GAA |   | GAA | AAC |
| EcoR I |   |   |   |   |   |   |   |   |   |   |   |   |
| Leu | Phe | Leu | Phe | Ser | Ala | Lys | Ile | Ser | Ala |   |   |   |
| CTC | TTC | TTG | TTC | TCT | GCT | AAG | ATT | TCT | GCC | GGC |   |   |
| GAG | AAG | AAC | AAG | AGA | CGA | TTC | TAA | AGA | CGG | CCG |   |   |
|   |   |   |   |   |   |   |   |   | NaeI |   |   |   |
|   |   |   |   |   |   |   |   |   | HpaII |   |   |   |

Example 13

Construction of DNA coding for fused protein comprising chimeric signal peptide and mature HSA (FIG. 18)

The double-stranded DNA coding for the chimeric signal peptide had a 5'-terminal EcoR I cohesive end and a 3'-terminal blunt end. To amplify the DNA, plasmid pUC19 was double-digested with EcoR I and Sma I to obtain a larger fragment. The vector fragment was ligated with the synthetic DNA to construct plasmid pUC-LY3. In plasmid pUC-HSA-CH (Reference Example 2), a GAT coding for Asp, which was an N-terminal amino acid of mature HSA, was preceded by C to form a sequence CGAT providing a Cla I cohesive end, and HSA cDNA extends to the Hind III site in the 3'-terminal non-translation region. Therefore, by double-digesting with Cla I and Hind III the plasmid pUC-HSA-CH, a cDNA coding for a complete mature HSA can be obtained. Plasmid pUC-LY3 was double-digested with EcoR I and Hpa II to obtain a 63 bp double stranded fragment, and plasmid pUC-HSA-CH was double-digested with EcoR I and Cla I to obtain a larger fragment. These fragments were ligated using T4 DNA ligase to construct a recombinant plasmid pUC-LY3-HSA.

Example 14

Figure 19:
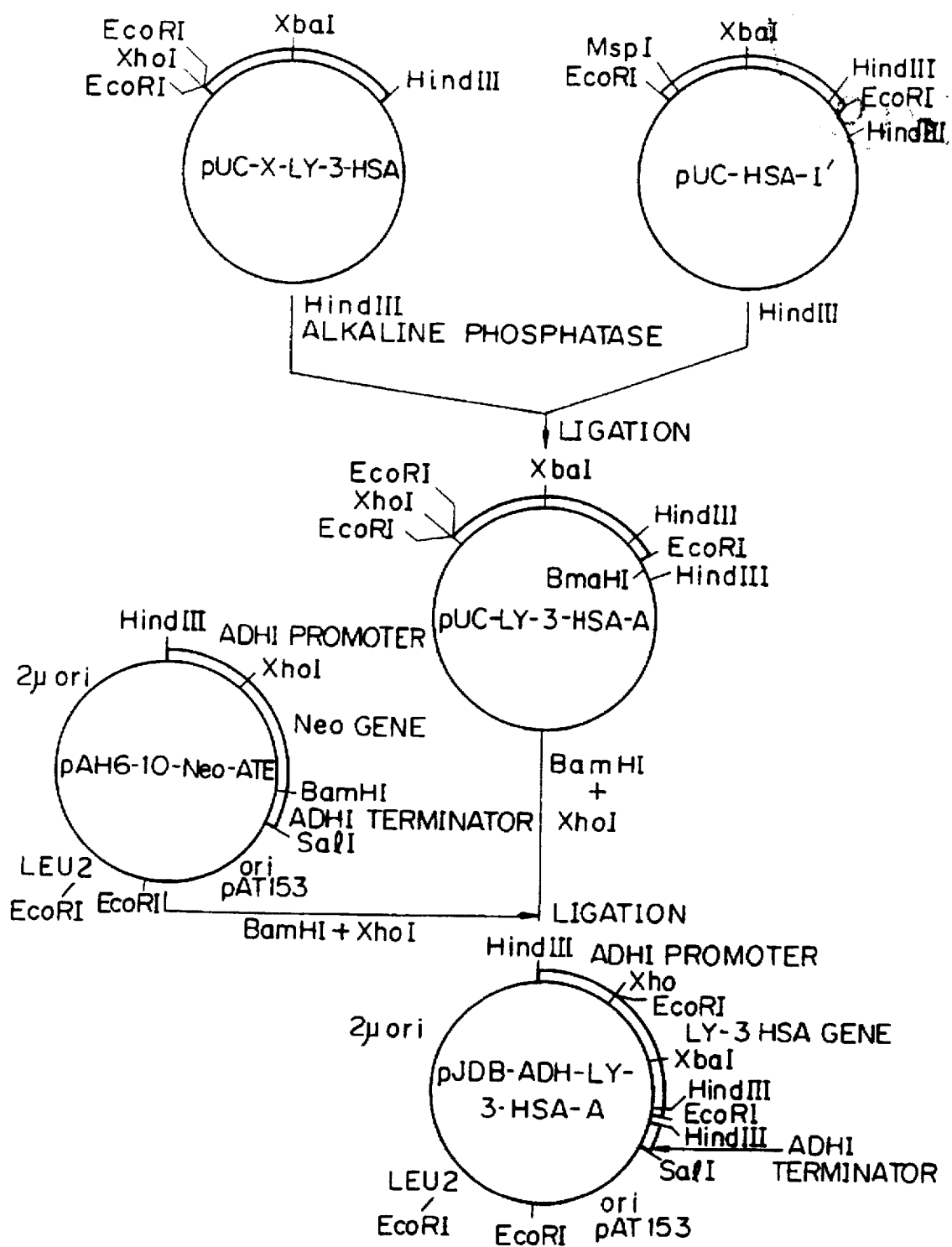
FIG. 19 shows a process for the construction of expression plasmid pJDB-ADH-LY3-HSA-A.

Construction of expression plasmid pJDB-ADH-LY3-HSA-A (FIGS. 18 and 19)

The above-mentioned plasmid was cleaved with EcoR I, and the phosphate group at the 5'-terminus of the linear plasmid was removed by alkaline phosphatase. This linear plasmid was re-circularized with a synthetic linker having an EcoR I cohesive end at both ends and having an internal Xho I site (Eco-Xho-Eco linker):

5'-AATTCTCGAG-3' 3'-GAGCTCTTAA-5' to construct plasmid pUC-X-LY3-HSA. The plasmid pUC-X-LY3-HSA was cleaved at the Hind III site present downstream of a structural gene coding for HSA, and the linear plasmid dephosphorylated by alkaline phosphatase. A recombinant plasmid pUC-HSA-I' (Example 3) was digested with Hind III to obtain a Hind III fragment of about 200 bp containing a 3'-non-coding region (a poly A addition signal and a poly A sequence) of HSA cDNA. These DNA were ligated to construct a recombinant plasmid pUC-LY3-HSA-A. This plasmid was double-digested with Xho I and BamH I to obtain a 2.0 kb fragment, which was then ligated with an Xho I-BamH I fragment of 8.1 kb of a yeast expression vector pAH6-10-Neo-ATE (Example 7) containing a promoter and terminator of the yeast alcohol dehydrogenase (ADHI) gene (ADCI) to construct a recombinant expression plasmid pJDB-ADH-LY3-HSA-A for the production of a fused protein comprising the artificial signal peptide and mature HSA.

*Escherichia coli* HB101/pJDB-ADH-LY3-HSA-A containing the above-mentioned plasmid was deposited with the FRI as FERM BP-2455 under the Budapest Treaty on Jun. 8, 1989.

Example 15

Transformation of yeast host with expression plasmid pJDB-ADH-LY3-HSA-A

Transformation of yeast host cells with an expression plasmid pJDB-ADH-LY3-HSA-A was carried out by a slight modification of the KUR method described by H. Hashimoto and H, Kimura Hakko to Kogyo, 43, 630–637, 1985). First, 0.1 ml of an overnight preculture of *Saccharomyces cerevisiae* AH 22 (MATa, leu 2-3, leu 2-112, his 4-519, Can I) in YPD medium [2% polypeptone (Difco), 1% yeast extract (Difco) and 2% glucose] was inoculated to 5 ml of YPD medium, and cultured at 30° C. for about 4 hours with shaking until the turbidity at $OD_{600}$ reached 0.5. The culture was centrifuged at 4° C. for 5 minutes at 2,000 rpm to collect cells, which were then resuspended in 5.0 ml of 0.1M LiSCN, and 1.5 ml of the suspension were centrifuged at 2,000 rpm for 5 minutes, or at 10,000 rpm for one minute. The cells thus obtained were resuspended in 10 μl of 2M LiSCN and 46 μl of 50% PEG 4000. To this suspension were added 10 μl of DNA solution (containing 5 to 10 μg of DNA), and the mixture was incubated at 30° C. overnight. To the suspension 1 ml of sterile distilled water was added and the whole was gently mixed by a vortex mixer. Next, the suspension was centrifuged at 2,000 rpm for 5 minutes, or at 10,000 rpm for one minute, and the collected cells were resuspended in 100 μl of sterile distilled water. The suspension was then spread on a selective agar plate (SD medium 20 μg/ml adenine sulfate, 20 μg/ml arginine hydrochloride 20 μg/ml methionine, 20 μg/ml histidine hydrochloride 20 μg/ml tryptophan, 20 μg/ml uracil, 30 μg/ml isoleucine, 30 μg/ml lysine hydrochloride, 30 μg/ml tyrosine, 50 μg/m phenylalanine, 150 μg/ml valine, 0.15% amino acid-free Yeast Nitrogen Base (Difco 0.5% ammonium chloride, 2% dextrose and 1.5% agar). The resulting colonies (Leu+) were suspended in 5 ml of SD medium, and cultured at 30° C. for 2 days. The culture was centrifuged at 2,000 rpm for 5 minutes at 4° C. to collect cells, which were then resuspended in 0.5 ml of 1M sorbitol. The suspension was centrifuged to collect cells, which were then resuspended in 0.5 ml of 1M sorbitol, 0.1% 2-mercaptoethanol and 400 μg/ml Zymolyase-100T (Seikagaku Kogyo). The suspension was incubated at 30° C. for 30 minutes to form spheroplasts, which were then centrifuged at 3,000 rpm for 5 minutes. The collected spheroplasts were resuspended in 100 μl of solution I (50 mM glucose, 10 mM EDTA and 25 mM Tris-HCl, pH 8.0), and after the addition of 200 μl of solution II (0.2N NaOH, 1% SDS), the suspension was thoroughly mixed and put on ice for 5 minutes. To the suspension were added 150 μl of 5M potassium acetate, and the suspension was thoroughly mixed, and after putting on ice for 10 minutes, centrifuged at 15,000 rpm for 5 minutes at 4° C. to obtain the supernatant, which was then transferred to a fresh tube. To the supernatant an equal volume of phenol/chloroform (1:1) was added, and the whole was violently mixed and centrifuged at 12,000 rpm for 5 minutes to obtain an aqueous layer, which was then transferred to a fresh tube. To the aqueous layer were added 750 μl of ethanol, and the mixture was thoroughly mixed by a vortex mixer. The mixture was centrifuged at 15,000 rpm for 5 minutes to obtain a precipitate, to which 0.5 ml of 70% ethanol were added. The mixture was mixed by a vortex mixer, and centrifuged at 15,000 rpm for 5 minutes to obtain a precipitate. The DNA precipitate thus obtained was dried under a reduced pressure, and dissolved in 30 μl of TE buffer. The DNA preparation obtained from the AH22 transformants containing plasmid pJDB-ADH-LY3-HSA-A was digested with various restriction enzymes such as Hind III, Xho I, EcoR I, BamH I and Sal I alone or in combination, and the resulting fragments were analyzed by agarose gel electrophoresis and polyacrylamide gel electrophoresis to confirm the structure of the plasmid.

Example 16

Production of HSA by transformants

A single colony formed on an SD (-Leu) plate was suspended in 5.0 ml of fresh SD(-Leu) liquid medium and cultured at 30° C. for 2 days with shaking until an $OD_{600}$ reached about 2.0. One hundred microliters of the culture were added to 5.0 ml YPD medium, and cultured at 30° C. for 24 hours until an $OD_{600}$ reached about 3.0. The culture was centrifuged at 5,000 rpm for 10 minutes at 4° C. to obtain a supernatant fraction. To the supernatant fraction was added an equal volume of 99% ethanol, and the whole was mixed and allowed to stand for 30 minutes at 4° C. Next, the mixture was centrifuged at 12,000 rpm for 10 minutes at 4° C. to obtain a precipitate. The precipitate was dissolved in 100 μl of 1× loading buffer (5% 2-mercaptoethanol, 0.0025% bromophenol blue, 2% SDS, 0.025M Tris-HCl and 8% glycerol), and 10 μl of the solution were applied to an electrophoretic gel [SDS-polyacrylamide gel; 4 to 20% concentration gradient; 84 mm (width)×90 mm (height)×1.0 mm (thickness)]. Electrophoresis was carried out in an electrophoresis buffer (0.025M Tris-HCl, pH 8.4, 0.192M glycine and 0.1% SDS) at a constant current of 60 mA for 60 minutes. As the molecular weight (MW) markers, egg white lysozyme (MW 14,400), soybean trypsin inhibitor (MW 21,500, carbonic anhydrase (MW 31,000), ovalbumin (MW 45,000), bovine serum albumin (MW 66,200), and phosphorylase B (MW 92,500), all obtained from BIO-RAD, were used. After the electrophoresis, proteins in the gel were stained with Coomassie Brilliant Blue, or as described hereinafter, immunologically detected after Western blotting. After the electrophoresis, the separated proteins were transferred to a nitrocellulose filter (BIO-RAD) using a semi-dry blotter (Sartorius). Namely, the filter was soaked in methanol for one hour and then in 25 mM Tris-HCl (pH 10.4)/20% methanol, and attached to an electrophoretic gel. This was sandwiched with filter papers which had been soaked in the above-mentioned buffer, and 0.3M Tris-HCl (pH 10.0) containing 20% methanol and 25 mM Tris-HCl (pH 9.4)/40 mM 6-amino-n-capronic acid, and was applied to the blotter. After applying a constant voltage of 6 V for about 1.5 hours, the filter was washed by shaking it in a solution of 20 mM Tris-HCl (pH 7.5)/500 mM NaCl(TBS) containing 3% gelatin at 37° C. for one hour, and then in TBS/0.05% Tween-20 for 5 minutes. Next, the filter was shaken in 40 ml of a solution containing anti-human serum albumin rabbit antibody (Cappel) which had been diluted 2,000-fold with TBS containing 1% gelatin, at room temperature overnight. The filter was washed with TBS (pH 7.5) containing 0.05% Tween-20 (T-TBS) while shaking. This procedure was once repeated. The filter was then shaken in 40 ml of a solution containing secondary antibody (goat anti-rabbit IgG antibody labeled with horseradish peroxidase; BIO-RAD) which had been diluted 3,000-fold with TBS containing 1% gelatin, for one hour at room temperature. Next, the filter was washed twice with T-TBS for 5 minutes and once with TBS for 5 minutes as described above. The filter was soaked in a mixture of 10 ml of methanol containing 30 mg of 4-chloronaphtol, 50 ml TBS and 30 μl of 30% hydrogen peroxide to detect a band corresponding to HSA, and the developing reaction was terminated by diluting with distilled water.

Example 17

Figure 20:
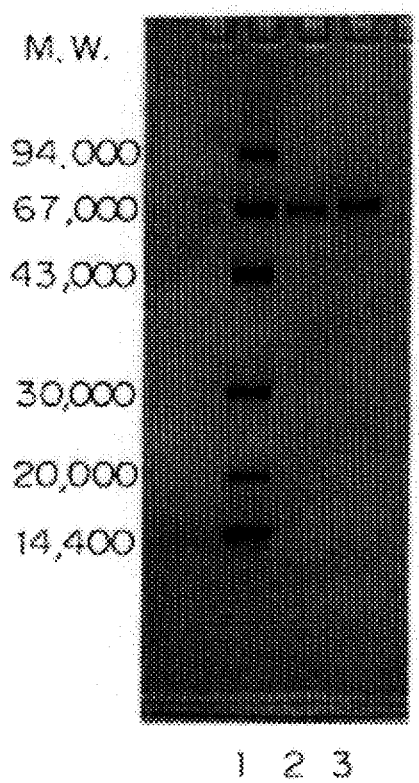
FIG. 20 shows a result of electrophoresis wherein HSA produced by culturing a transformant AH22 (pJDB-ADH-LY3-HSA-A) containing HSA CDNA was subjected to SDS-polyacrylamide gel electrophoresis and detected by Coomassie Brilliant Blue staining.

Biochemical homology between HSA produced by yeast transformants and HSA prepared from human serum (1) Molecular weight A sample of HSA isolated from a yeast culture was reduced with 2-mercaptoethanol, treated with SDS, and applied to a 12%–30% polyacrylamide gradient gel in SDS, and electrophoresis was carried out under the conditions described by Laemmli, U.K., Nature, 227 680–685, 1970. As molecular weight markers, phosphorylase B(MW 92,500), bovine serum albumin (MW 66,200), ovalbumin (MW 45,000), carbonic anhydrase (MW 31,000), soybean trypsin inhibitor (MW 21,500), and egg white lysozyme (MW 14,400) were used. Proteins were detected by Coomassie Brilliant Blue staining. Simultaneously, as a control, the mobility of commercially available HSA purified from human serum was run, and both the HSAs were compared, and as a result, HSA produced by yeast transformants and HSA derived from human serum exhibited the same mobility, and their molecular weight was 67,000, as shown in FIG. 20.

(2) Electrophoretic properties Native gel electrophoresis

Figure 21:
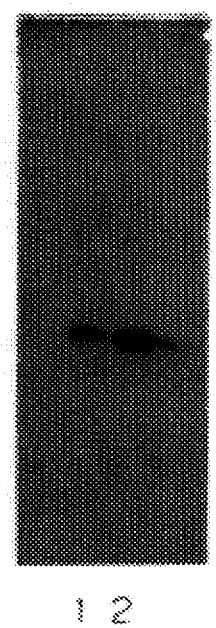
FIG. 21 shows a result of a comparison of HSA produced by yeast transformants and HSA prepared from human serum, by native polyacrylamide gradient gel electrophoresis.

A sample of HSA isolated from yeast culture was applied to a 12%–30% polyacrylamide gradient gel free from SDS, and electrophoresis was carried out under the conditions as described above but excluding SDS. Protein bands were detected by Coomassie Brilliant Blue staining. Simultaneously, as a control, a commercially available HSA purified from human serum was run, and the electric behavior thereof was compared. In native (excluding SDS) gel electrophoresis, HSA produced by yeast transformants and HSA derived from human serum exhibited the same electrophoretic property, as shown in FIG. 21.

Isoelectric focusing

Figure 22:
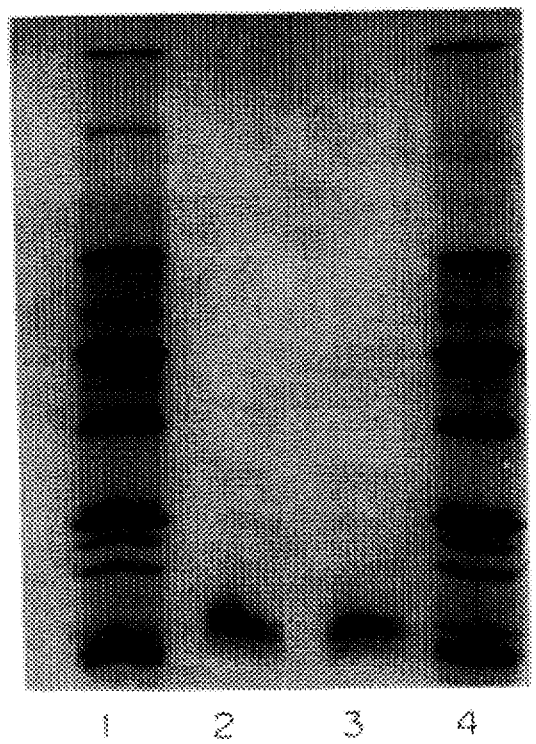
FIG. 22 shows a result of a comparison of HSA produced by yeast transformant and HSA prepared from human serum, by isoelectroic focusing.

Isoelectric focusing was carried out using an Ampholine PAG plate, pH range 3.5–9.5 (LKB) according to the maker's manual. As isoelectric point markers, LKB's pI markers, i.e., C-phycocyanin (pI 4.75, 4.85), azurin (pI 5.65), trifluoroacetylated myoglobin (porcine pI 5.9), myoglobin (porcine pI 6.45), myoglobin (horse pI 7.3) mygolobin (whale pI 8.3), and cytochrome C (pI 10.6) were used. HSA produced by yeast transformants exhibited several bands between pI 4,8 and pI 5.2, which were the same as HSA purified from human serum. This result is set forth in FIG. 22.

(3) Determination of N-terminal amino acid sequence

The N-terminal amino acid sequence of HSA (20 μg) produced by yeast transformants was determined using a gas phase protein sequencer 477A (Applied Biosystems) according to the maker's manual, and as a result, an amino acid sequence from the amino-terminus was Asp-Ala-His-Lys-Ser-Glu-Val-Ala-His-Arg, which was completely identical with the reported amino acid sequence from the amino-terminal amino acid sequence of HSA. Calculating from the recovery of N-terminal amino acids, it was estimated that the HSA preparation tested had an N-terminal homogeneity of at least 95%. From this result the absence of a pre HSA sequence due to an incomplete processing was confirmed.

(4) Reverse Phase column chromatography

As an HPLC apparatus, Shimazu LC-6A Type Gradient-LC system equipped with a TSK-gel phenyl 5PW RP column was used. The column was equilibrated with 0.1% trifmoroacetic Acid/mater, and HSA produced by yeast transformants, a commercial HSA purified from human serum, and the mixtures thereof were separately applied. Elution of the protein was carried out with an acetonitrile concentration gradient from 0% to 70% in 0.1% trifluoroacetic acid for 60 minutes at a flow rate of 1 ml/minutes.

Figure 23:
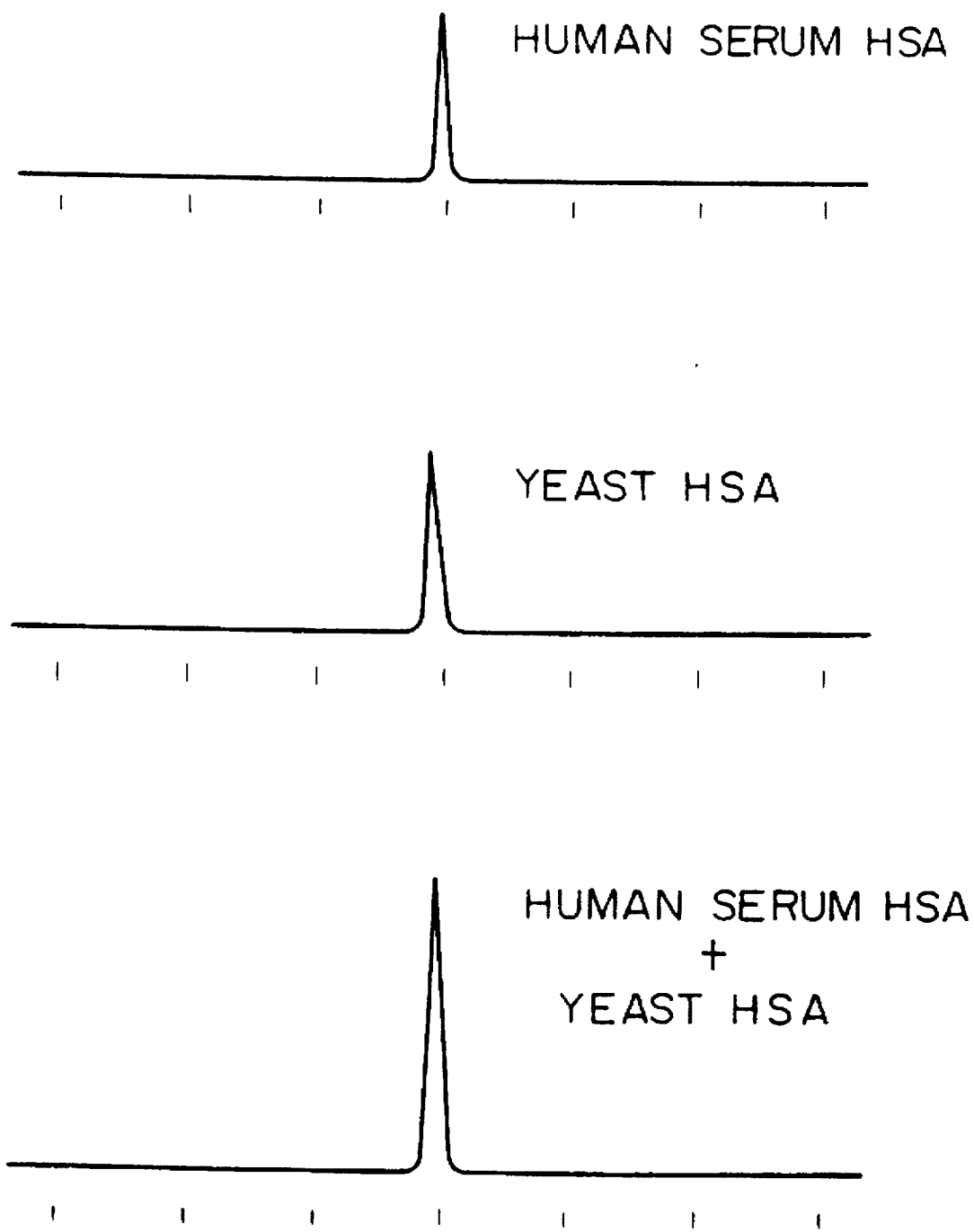
FIG. 23 shows a result of a comparison of HSA produced by yeast transformants and HSA prepared by human serum, by reverse phase HPLC.

Under these conditions HSA produced by yeast transformants provided a single sharp peak whose retentiontime and shape were in distinguishable from those of HSA purified from human serum. Moreover, when these two HSAs were mixed and the mixture was chromatographed on the column, the mixture provided a single sharp peak, indicating that the behavior of these two HSAs on the reverse phase column was absolutely identical. The results are set forth in FIG. 23.

(5) Immunological properties

Figure 24:
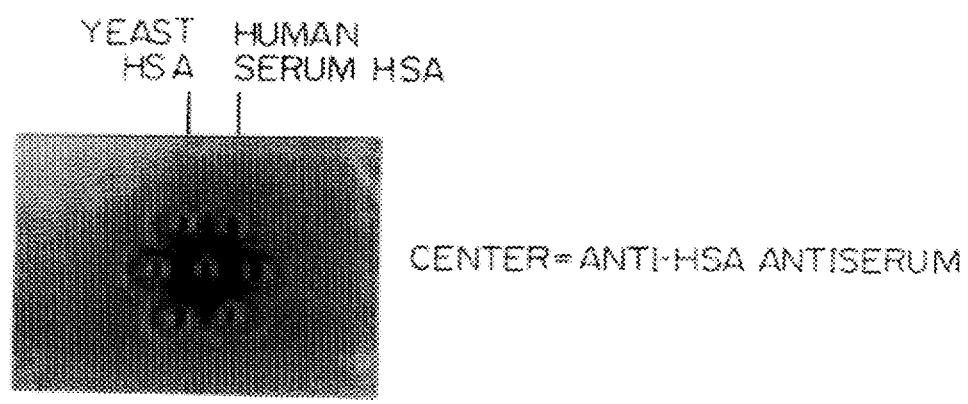
FIG. 24 shows a result of a comparison of HSA produced by yeast transformants and HSA prepared from human serum, by the Ouchterlony method.

Immunodifusion was carried out according to a method of Ouchterlony, O, Progr. Allergy, 6, 30, 1962. After formation of precipitin lines and deproteinization with physiological saline, the precipitin lines were stained with Coomassie Brilliant Blue. The antisera used for the immunodiffusion test was rabbit anti-HSA antiserum (Cappel). A precipitain line by HSA produced by the yeast transformants was completely fused with a precipitin line by HSA purified from human serum, revealing the absence of antigenic difference between both HSAs. The results are set forth in FIG. 24.

Example 18

Synthesis of DNA coding for MFα1 prepropeptide

When DNA coding for MFα1 prepro peptide was constructed by ligating synthetic oligodeoxyribonucleotides, enzyme recognition sites were conveniently provided in the DNA sequence. For this purpose, Nhe I and Hind III recognition sites were used. Moreover, for a convenient insertion of the DNA to a vector, the DNA was provided with EcoR I and Xho I sites at the 5'-terminus, and a Cla site at the 3'-terminus. Since it is reported that tetrapeptide Glu-Ala-Glu-Ala present at the C-terminus of MFα1 pre-propeptide is not essential ffor correct processing (occurring at the c-terminal side of Lys-Arg dipeptide just preceding the Glu-Ala-Glu-Ala) and secretion of a foreign protein fused to the MFα1-prepropeptide (Brake et al., Natl. Acad. Sci. U.S.A. 81, 4642–4646, 1984), a shortened MFα1 prepropeptide lacking the Glu-Ala-Glu-Ala tetrapeptide was used as a leader sequence. Accordingly, the leader sequence consists of 85 amino acids.

To construct a DNA coding for the leader sequence, the following oligonucleotides were synthesized;

| | |
|---|---|
| 1 | AATTCTCGAGATGAGATTTCCTTCAATTTTTACTGCA |
| 2 | GTAAAAATTGAAGGAAATCTCATCTCGAG |
| 3 | CTAGCATTGCTGCTAAAGAAGAAGGGGTAAGCTTGGATAAACG |
| 4 | CGCGTTTATCCAAGCTTACCCCTTCTTCTTTAGCAGCAATG |
| 5 | GTTTTATTCGCAGCATCCTCCGCATTAGCTGCTCCAGTCAAC ACTACAACAGAAGATGAAACG |
| 6 | ATCTTCTGTTGTAGTGTTGACTGGAGCAGCTAATGCGGAGGA TGCTGCGAATAAAACTGCA |
| 7 | GCACAAATTCCGGCTGAAGCTGTCATCGGTTACTCAGATTTA GAAGGGGATTTCGATGTTGCT |
| 8 | ATCGAAATCCCCTTCTAAATCTGAGTAACCGATGACAGCTTC AGCCGGAATTTGTGCCGTTTC |
| 9 | GTTTTGCCATTTTCCAACAGCACAAATAACGGGTTATT-GTTTATAAATACTACTATTGCTAGCG |
| 10 | AATTCGCTAGCAATAGTAGTATTTATAAACAATAACCCGTTA TTTGTGCTGTTGGAAAATGGCAAAACAGCAAC |

Example 19

Figure 25:
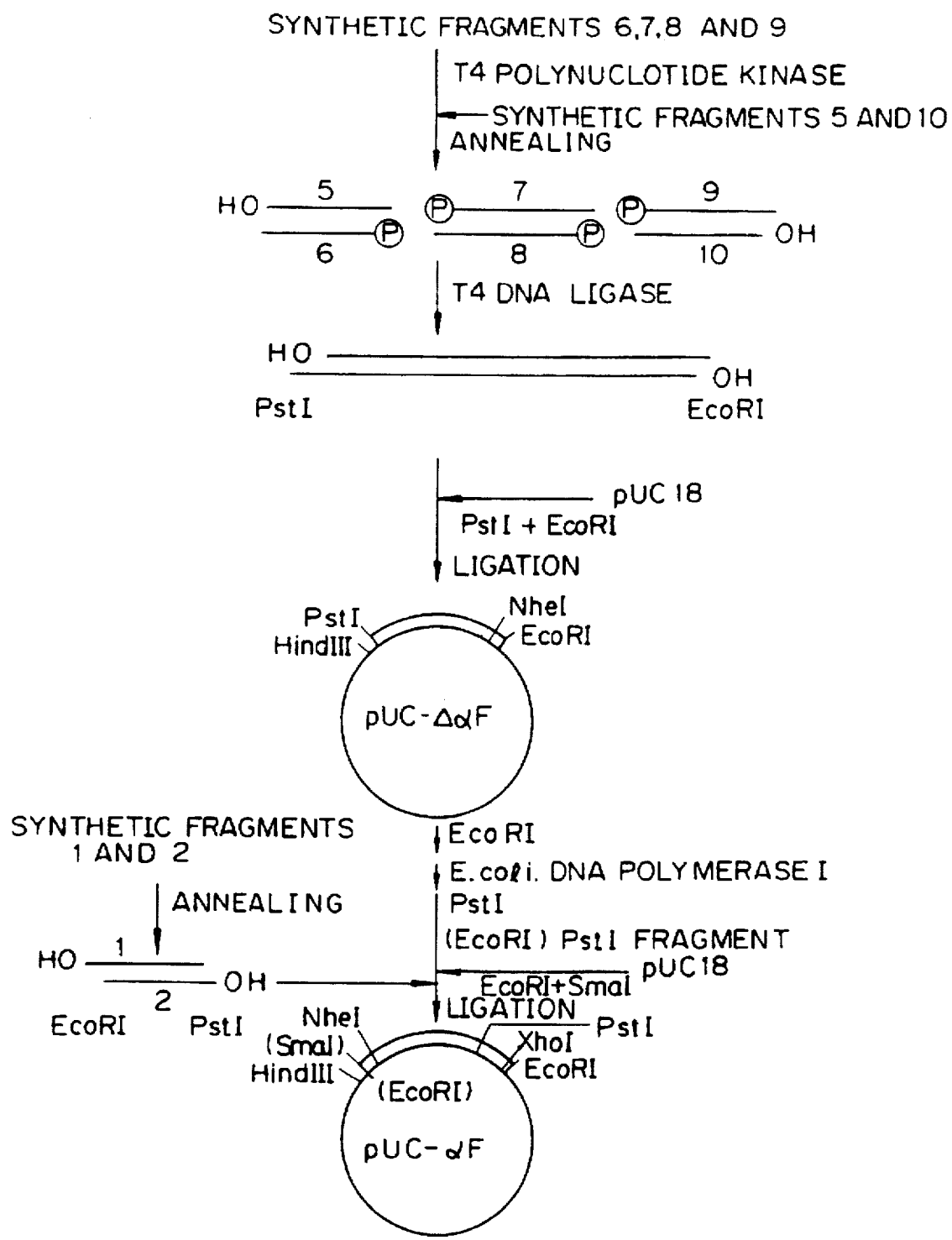
FIG. 25 shows a process for the construction of plasmid pUC-αF.

Ligation of synthetic DNA coding for prepropeptide and CDNA coding for mature HSA (FIG. 25)

Synthetic oligonucleotides 6, 7, 8 and 9 were phosphorylated at their 5'-termini by T4 polynucleotide kinase. Next, oligonucleotides 5 and 6, 7 and 8, and 9 and 10 were annealed, and ligated using T4 DNA ligase.

The resulting DNA had Pst I and EcoR I cohesive ends at the termini thereof. The DNA was ligated with pUC 18 which had been double-digested with Pst I and EcoR I to construct recombinant plasmid pUC-ΔαF. The plasmid pUC-ΔαF was cleaved with EcoR I to prepare a linear DNA, which was then treated with E. coli DNA polymerase I to make the ends blunt. The linear DNA was cut with Pst I to obtain a DNA fragment coding for a portion of MFα1 leader sequence, which was then ligated with a double-stranded DNA fragment obtained by annealing synthetic oligonucleotides 1 and 2, using T4 DNA ligase. The resulting DNA fragment was ligated with a DNA fragment prepared by cleaving pUC18 with EcoR I and Sma I to construct recombinant plasmid pUC-αF. The plasmid pUC-αF was double-digested with EcoR I and Nhe I to obtain a DNA fragment coding for an MFα1 prepropeptide lacking a part of the c-terminal side thereof, which was then ligated with a double-stranded DNA fragment obtained by annealing synthetic oligonucleotides 3 and 4, using T4 DNA ligase. The double-stranded DNA fragment thus constructed had the following sequence.

| | Met | Arg | Phe | Pro | Ser | Ile | Phe | Thr | Ala |
|---|---|---|---|---|---|---|---|---|---|
| AATTCTCGAG | ATG | AGA | TTT | CCT | TCA | ATT | TTT | ACT | GCA |
| GAGCTC | TAC | TCT | AAA | GGA | AGT | TAA | AAA | TGA | CGT |
| EcoRI XhoI | | | | | | | | | PstI |
| | Val | Leu | Phe | Ala | Ala | Ser | Ser | Ala | Leu | Ala |
| | GTT | TTA | TTC | GCA | GCA | TCC | TCC | GCA | TTA | GCT |
| | CAA | AAT | AAG | CGT | CGT | AGG | AGG | CGT | AAT | CGA |
| | Ala | Pro | Val | Asn | Thr | Thr | Thr | Glu | Asp | Glu |
| | GCT | CCA | GTC | AAC | ACT | ACA | ACA | GAA | GAT | GAA |
| | CGA | GGT | CAG | TTG | TGA | TGT | TGT | CTT | CTA | CTT |
| | Thr | Ala | Gln | Ile | Pro | Ala | Glu | Ala | Val | Ile |
| | ACG | GCA | CAA | ATT | CCG | GCT | GAA | GCT | GTC | ATC |
| | TGC | CGT | CTT | TAA | GGC | CGA | CTT | CGA | CAG | TAG |
| | Gly | Tyr | Ser | Asp | Leu | Glu | Gly | Asp | Phe | Asp |
| | GGT | TAC | TCA | GAT | TTA | GAA | GGG | GAT | TTC | GAT |
| | CCA | ATG | AGT | CTA | AAT | CTT | CCC | CTA | AAG | CTA |
| | Val | Ala | Val | Leu | Pro | Phe | Ser | Asn | Ser | Thr |
| | GTT | GCT | GTT | TTG | CCA | TTT | TCC | AAC | AGC | ACA |
| | CAA | CGA | CAA | AAC | GGT | AAA | AGG | TTG | TCG | TGT |
| | Asn | Asn | Gly | Leu | Leu | Phe | Ile | Asn | Thr | Thr |
| | AAT | AAC | GGG | TTA | TTG | TTT | ATA | AAT | ACT | ACT |
| | TTA | TTG | CCC | AAT | AAC | AAA | TAT | TTA | TGA | TGA |
| | Ile | Ala | Ser | Ile | Ala | Ala | Lys | Glu | Glu | Gly |
| | ATT | GCT | AGC | ATT | GCT | GCT | AAA | GAA | GAA | GGG |
| | TAA | CGA | TCG | TAA | CGA | CGA | TTT | CTT | CTT | CCC |
| | NheI | | | | | | | | | |
| | Val | Ser | Leu | Asp | Lys | Arg | | | | |
| | GTA | AGC | TTG | GAT | AAA | CG | | | | |
| | CAT | TCG | AAC | CTA | TTT | GCG | C | | | |
| | Hind III | | | | | Cla | I | | | |

Using T4 DNA ligase, the double-stranded DNA fragment was ligated with a larger fragment which was obtained by double digestion of PUC-HSA-CH containing a DNA sequence coding for mature HSA with EcoR I and Cla I, resulting in the construction of the recombinant plasmid pUC-αF-HSA.

Example 20

Figure 26:
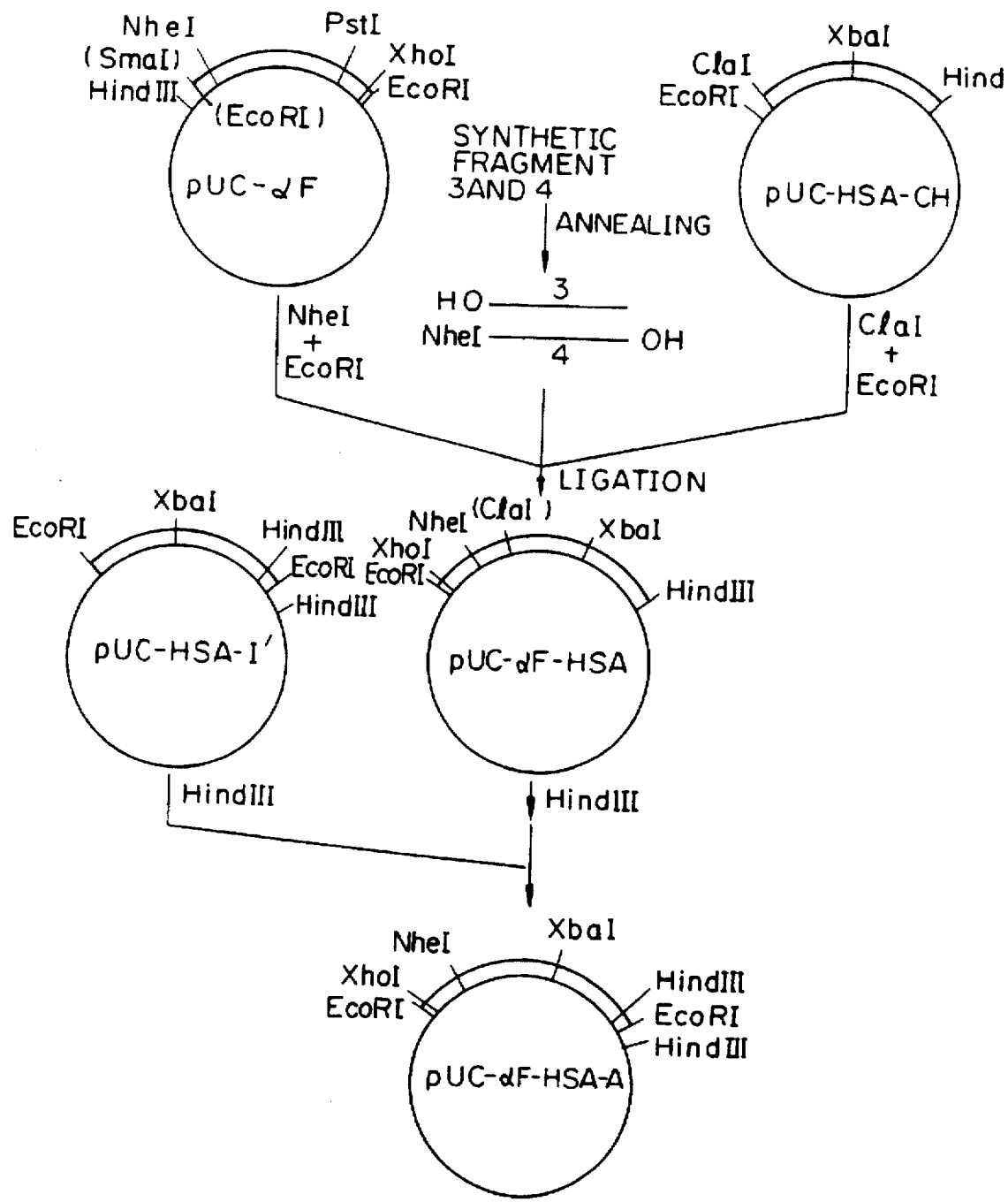
FIG. 26 shows a process for the construction of plasmid pUC-αF-HSA-A.
Figure 27:
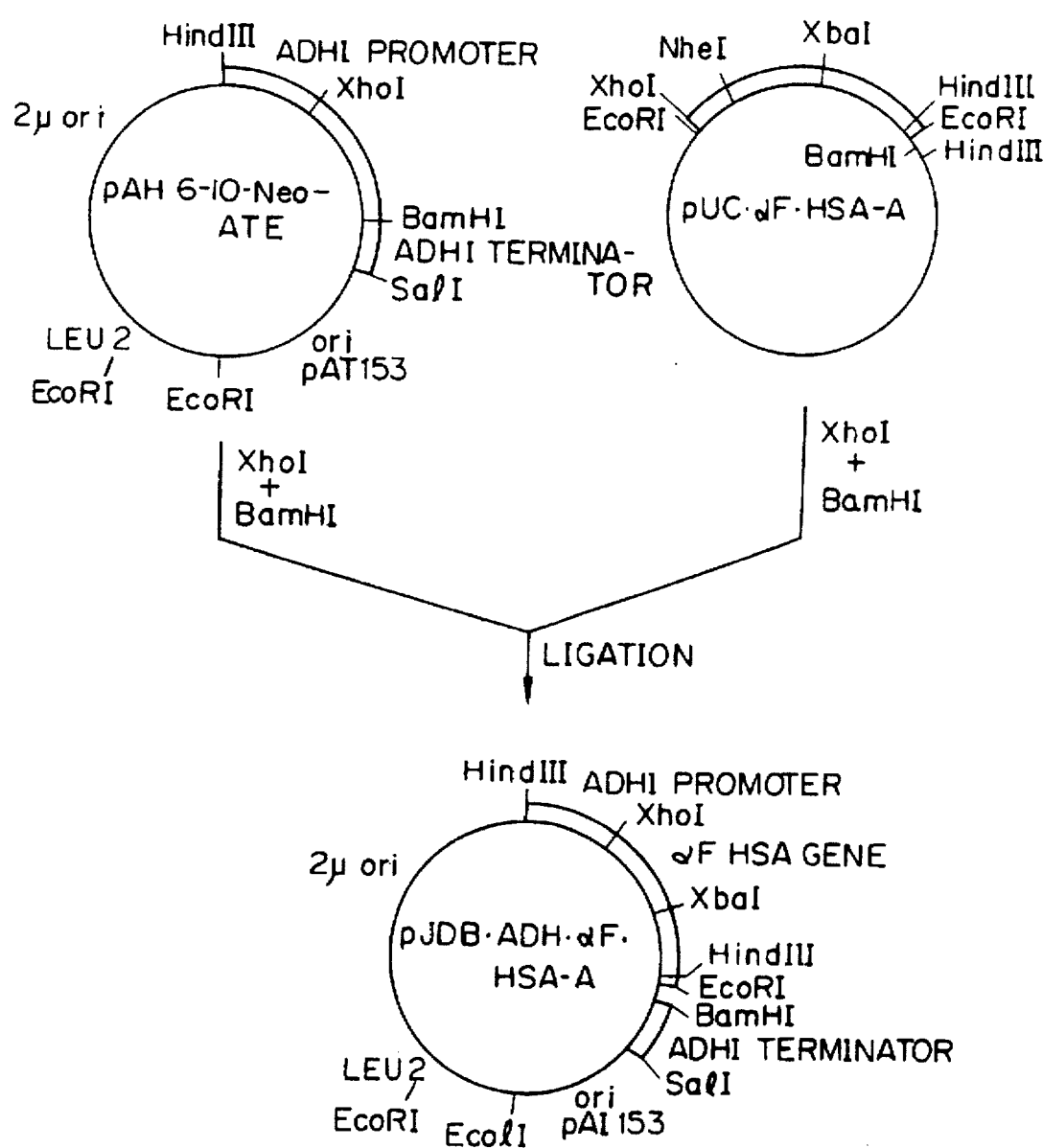
FIG. 27 shows a process for the construction of expression plasmid pJDB-ADH-αF-HSA-A.

Insertion of a poly A sequence and an AATAAA signal sequence (FIG. 26)

Plasmid pUC-HSA-I' (Example 4) containing a 3'-terminal half of an HSA coding sequence and a 3'-non-coding region which contains a poly A addition signal and a poly A sequence was digested with Hind III to obtain a Hind III fragment of about 200 bp containing a poly A addition signal, a poly A sequence, and a sequence derived from the pUC vector. Next, the Hind III fragment was inserted into a Hind III site present at the 3'-end of HSA cDNA in plasmid pUC-αF-HSA, to construct plasmid pUC-αF-HSA-A.

Example 21

Construction of expression plasmid pJDB-ADH-αF-HSA-A

Plasmid pUC-αF-HSA-A was double-digested with Xho I and BamH I to obtain a DNA fragment containing an MFα1 leader sequence and an HSA cDNA comprising a mature HSA coding sequence, poly A addition signal, and a poly A sequence. On the other hand, plasmid pAH6-10-NEO-ATE (Example 7) was double-digested with Xho I and BamH I to obtain a larger fragment excluding the NEO gene (coding for aminoglucoside phosphotransferase 3'(II)). These DNA fragments were ligated to construct recombinant plasmid pJDB-ADH-αF-HSA-A.

*Escherichia coli* HB101/pJDB-ADH-αF-HSA-A was deposited with the FRI as FERM BP-2453 under the Budapest Treaty on Jun. 8, 1989.

Example 22

Transformation of yeast host with expression plasmid pJDB-ADH-αF-HSA-A

Transformation of yeast host cells with an expression plasmid pJDB-ADH-αF-HSA-A was carried out by a slight modification of the KUR method described by H. Hashimoto and H. Kimura (Hakko To Kogyo, 43, 630–637, 1985). First, 0.1 ml of an overnight preculture of *Saccharomyces cerevisiae* AH22 (MATa, leu 2-3, leu 2-112, his 4-519, CanI) in YPD medium [2% polypeptone (Difco), 1% yeast extract (Difco) and 2% glucose] was inoculated to 5 ml of YPD medium, and cultured at 30° C. for about 4 hours with shaking until the turbidity at $OD_{600}$ reaches 0.5. The culture was centrifuged at 4° C. for 5 minutes at 2,000 rpm to collect cells, which were then resuspended in 5.0 ml of 0.1M LiSCN, and 1.5 ml of the suspension were centrifuged at 2,000 rpm for 5 minutes, or at 10,000 rpm for one minute. The cells thus obtained were resuspended in 10 μl of 2M LiSCN and 46 μl of 50% PEG 4000. To this suspension were added 10 μl of DNA solution (containing 5 to 10 μg of DNA), and the mixture was incubated at 30° C. overnight. To the suspension 1 ml of sterile distilled water was added, and the whole was gently mixed by a vortex mixer. Next, the suspension was centrifuged at 2,000 rpm for 5 minutes, or at 10,000 rpm for one minute, the collected cells were resuspended in 100 μl of sterile distilled water. The suspension was then spread on a selective agar plate [SD medium: 20 μg/ml adenine sulfate, 20 μg/ml arginine hydrochloride, 20 μg/ml methionine, 20 μg/ml histidine hydrochloride, 20 μg/ml tryptophan, 20 μg/ml uracil, 30 μg/ml isoleucine, 30 μg/ml lysine hydrochloride, 30 μg/ml tyrosine, 50 μg/ml phenylalanine, 150 μg/ml valine, 0.15% amino acid-free Yeast nitrogen Base (Difco), 0.5% ammonium chloride, 2% dextrose and 1.5% agar). The resulting colonies ($Leu^+$) were suspended in 5 ml of SD medium, and cultured at 30° C. for 2 days. The culture was centrifuged at 2,000 rpm for 5 minutes at 4° C. to collect cells, which were then resuspended in 0.5 ml of 1M sorbitol. The suspension was centrifuged to collect cells, which were then resuspended in 0.5 ml of 1M sorbitol, 0.1% 2-mercaptoethanol and 400 μg/ml Zymolyase-100T (Seikagaku Kogyo). The suspension was incubated at 30° C. for 30 minutes to form spheroplasts which were then centrifuged at 2,000 rpm for 5 minutes. The collected spheroplasts were resuspended in 100 μl of solution I (50 mM glucose, 10 mM EDTA and 25 mM Tris-HCl, pH 8.0), and after the addition of 200 μl of solution II (0.2N NaOH, 1% SDS), the suspension was thoroughly mixed and put on ice for 5 minutes. To the suspension were added 150 μl of 5M potassium acetate, and the suspension was thoroughly mixed, and after putting on ice for 10 minutes, centrifuged at 15,000 rpm for 5 minutes at 4° C. to obtain the supernatant, which was then transferred to a fresh tube. To the supernatant an equal volume of phenol/chloroform (1:1) was added, and the whole was violently mixed and centrifuged at 12,000 rpm for 5 minutes to obtain an aqueous layer, which was then transferred to a fresh tube. To the aqueous layer were added 750 μl of ethanol, and the mixture was thoroughly mixed by a vortex mixer. The mixture was centrifuged at 15,000 rpm for 5 minutes to obtain a precipitate, to which 0.5 ml of 70% ethanol were added. The mixture was mixed by a vortex mixer, and centrifuged at 15,000 rpm for 5 minutes to obtain a precipitate. The DNA precipitate thus obtained was dried under a reduced pressure, and dissolved in 30 μl of TE buffer. The DNA preparation obtained from the AH22 transformants containing plasmid pJDB-ADH-αF-HSA-A was digested with various restriction enzymes, such as Hind III, Xho I, EcoR I, BamH I and Sal I alone or in combination, and the resulting fragments were analyzed by agarose gel electrophoresis and polyacrylamide gel electrophoresis to confirm the structure of the plasmid.

Example 23

Figure 28:
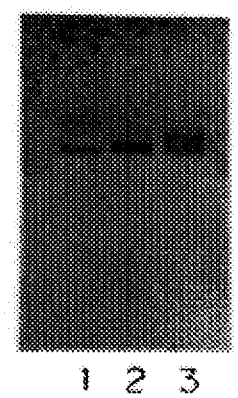
FIG. 28 shows a Western blot of the cell extracts from yeast cells transformed with the present expression plasmid pJDB-ADH-αF-HSA-A (lane 1), the supernatant therefrom (lane 2), and HSA prepared from human serum as a control (lane 3)

Production of HSA by transformants (FIG. 28)

A single colony formed on an SD (-Leu) plate was suspended in 5.0 ml of fresh SD (-Leu) liquid medium and cultured at 30° C. for 2 days with shaking until an $OD_{600}$ reached about 2.0. One hundred microliters of the culture were added to 5.0 ml of YPD medium, and cultured at 30° C. for 24 hours until an $OD_{600}$ reached about 3.0. The culture was centrifuged at 5,000 rpm for 10 minutes at 4° C. to obtain the supernatant fraction. To the supernatant fraction was added an equal volume of 99% ethanol, and the whole was mixed and allowed to stand for 30 minutes at 4° C. Next, the mixture was centrifuged at 12,000 rpm for 10 minutes at 4° C. to obtain the precipitate. The precipitate was dissolved in 100 μl of 1×loading buffer (5% 2-mercaptoethanol, 0.0025% bromophenol blue, 2% SDS, 0.025M Tris-HCl and 8% glycerol), and 10 μl of the solution were applied to an electrophoretic gel [SDS-polyacrylamide gel; 4 to 20% concentration gradient; 84 mm (width)×90 mm (height)×1.0 mm (thickness)]. Electrophoresis was carried out in an electrophoresis buffer (0.025M Tris-HCl, pH 8.4, 0.192M glycine and 0.1% SDS) at a constant current of 60 mA for 60 minutes. As the molecular weight (MW) marker, egg white lysozyme (MW 14,400), soybean trypsin inhibitor (MW 21,500) carbonic anhydrase (MW 31,000), ovalbumin (MW 45,000), bovine serum albumin (MW 66,200), and phosphorylase B (MW 92,500), all obtained from BIO-RAD, were used. After the electrophoresis, proteins in the gel were stained with Coomassie Brilliant Blue, or as described hereinafter, immunologically detected after Western blotting. After the electrophoresis, the separated proteins were transferred to a nitrocellulose filter (BIO-RAD) using a semi-dry blotter (Sartorius). Namely, the filter was soaked in methanol for one hour and then in 25 mM Tris-HCl (pH 10.4)/20% methanol, and attached to an electrophoretic gel. This was sandwiched with filter papers which had been soaked in the above-mentioned buffer, and 0.3M Tris-HCl (pH 10.0) containing 20% methanol and 25 mM Tris-HCl (pH 9.4)/40 mM 6-amino-n-capronic acid, and was applied to the blotter. After applying a constant voltage of 6 V for about 1.5 hours, the filter was washed by shaking it in a solution of 20 mM Tris-HCl (pH 7.5)/500 mM NaCl (TBS) containing 3% gelatin at 37° C. for one hour, and then in TBS/0.05% Tween-20 for 5 minutes. Next, the filter was shaken in 40 ml of a solution containing anti-human serum albumin rabbit antibody (Cappel) which had been diluted 2,000-fold with TBS containing 1% gelatin, at room temperature overnight. The filter was washed with TBS (pH 7.5) containing 0.05% Tween-20 (T-TBS) while shaking. This procedure was once repeated. The filter was then shaken in 40 ml of a solution containing secondary antibody (goat anti-rabbit IgG antibody labeled with horseradish peroxidase; BIO-RAD) which had been diluted 3,000-fold with TBS containing 1% gelatin, for one hour at room temperature. Next, the filter was washed twice with T-TBS for 5 minutes and once with TBS for 5 minutes as described above. The filter was soaked in a mixture of 10 ml of methanol containing 30 mg of 4-chloronaphtol, 50 ml TBS and 30 μl of 30% hydrogen peroxide to detect a band corresponding to HSA, and the developing reaction was terminated by diluting with distilled water. The results are set forth in FIG. 28.

Example 24

Figure 29:
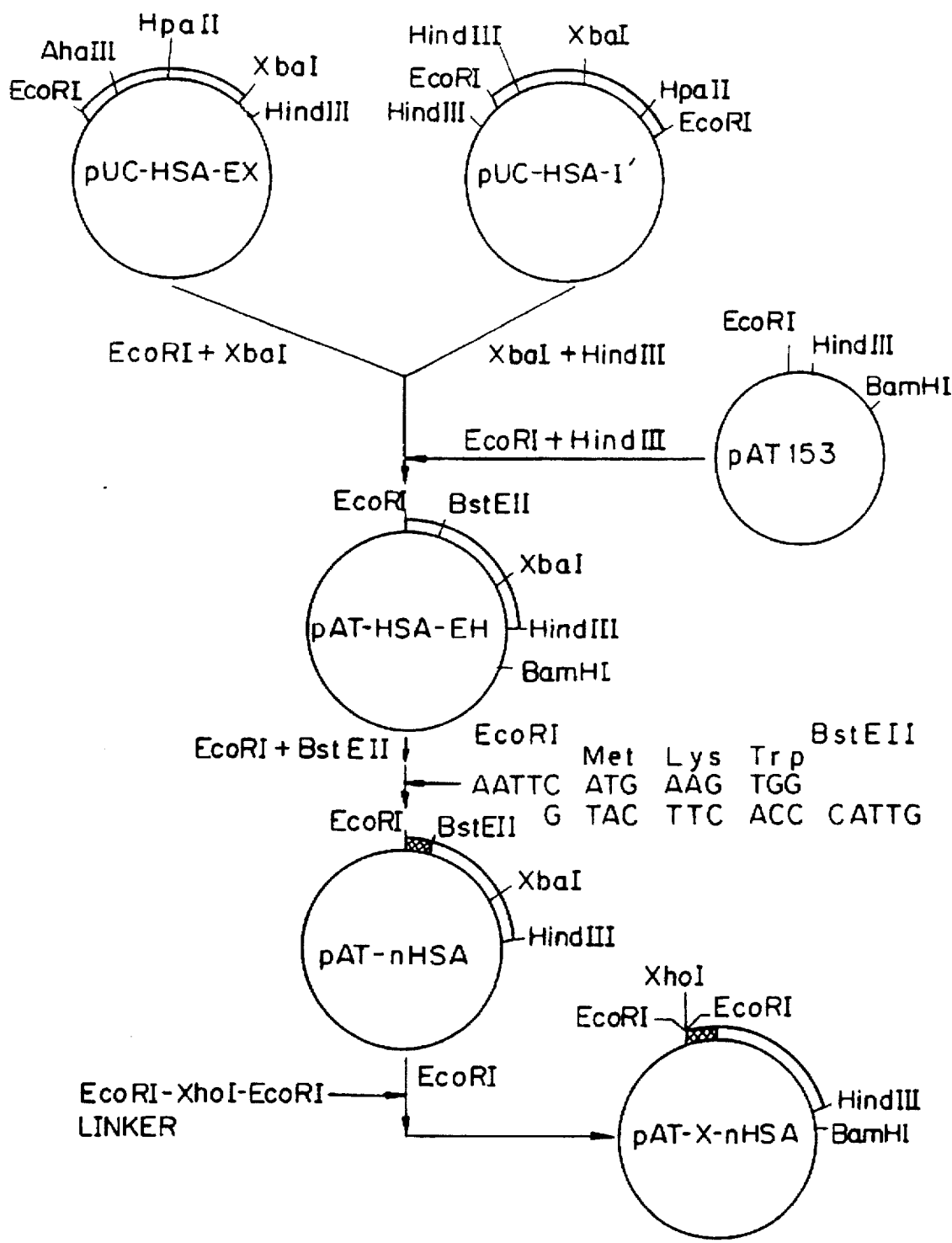
FIG. 29 shows a process for the construction of plasmid pAT-X-nHSA.

Construction of plasmid pAT-nHSA (FIG. 29)

Plasmid pUC-HSA-EX (Reference Example 2) containing a 5'-non-coding region and an upstream half of a coding region of prepro HSA cDNA was double-digested with EcoR I and Xba I to obtain a prepro HSA cDNA region. Plasmid pUC-HSA-I' (Example 3) containing a downstream half of a coding region and a 3'-non-coding region of HSA cDNA was double-digested with Xba I and Hind III to obtain a DNA fragment. Plasmid pAT153 (Amersham; Twig, A. J. and Sheratt, D., Nature 283, 216–218, 1980) was digested with EcoR I and Hind III to obtain a DNA fragment. These three DNA fragments were ligated to construct plasmid pAT-HSA-EH. To directly link the cDNA coding for a prepro HSA with a strong yeast promoter, an EcoR I site positioned at the 5'-terminus of the cDNA and the BstE II site positioned between the third condon for amino acid Trp and the fifth codon for amino acid Thr in the nucleotide sequence coding for the signal peptide of prepro HSA were used. the EcoR I-BstE II fragment containing the 5'-non-coding sequence and the sequence encoding from the N-terminus to the third amino acid of the signal peptide was eliminated from pAT-HSA-EH. The remaining large DNA fragment was ligated with a 5'-phosphorylated synthetic DNA fragment:

```
EcoR I          BstE II
5'-AATTCATGAAGTGG
      GTACTTCACCCATTG-5'
``` having an EcoR I cohesive end at the 5'-terminus thereat and a BstE II cohesive end at the 3'-terminus and coding for the N-terminal three amino acid of HSA signal peptide, using T4 DNA ligase to construct plasmid pAT-nHSA containing natural prepro HSA cDNA.

Example 25

Figure 30:
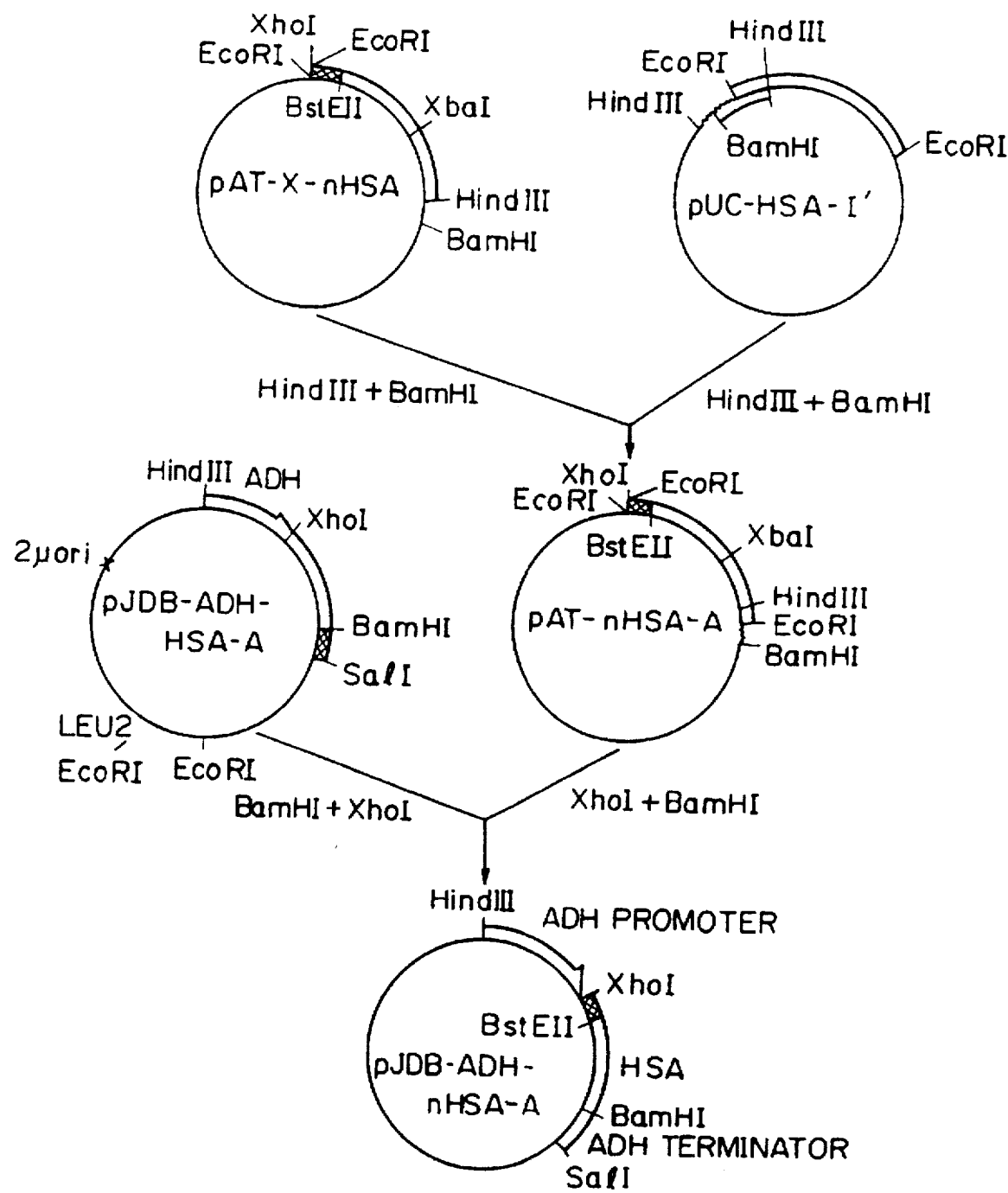
FIG. 30 shows a process for the construction of expression plasmid pJDB-ADH-nHSA-A.

Construction of expression plasmid pJDB-ADH-nHSA-A (FIGS. 29 and 30)

Plasmid pAT-nHSA was cleaved with EcoR I at the 5'-terminus of prepro HSA cDNA, and to this site a synthetic linker:

```
        EcoR   IXhoIEcoR I
    5'-AATTCTCGAG
           GAGCTCTTAA-5'
``` having EcoR I cohesive ends and an internal Xho I site was added to construct plasmid pAT-X-nHSA. The plasmid pAT-X-nHSA was digested with Hind III and Bam I to remove a Hind III-Bam I fragment which was derived from plasmid pAT153 and positioned adjacent to a 3'-terminus of prepro HSA cDNA. On the other hand, plasmid pUC-HSA-T was digested with Hind III and Bam I to obtain a Hind III-Bam I fragment containing a poly A addition signal, a poly A sequence of prepro HSA cDNA and a region derived from pUC18 vector. Next, the large DNA fragment from plasmid pAT-X-nHSA and the fragment from pUC-HSA-T were ligated to construct plasmid pAT-nHSA-A. Plasmid pAT-nHSA-A, which was constructed to express an entire prepro HSA cDNA containing a poly A addition signal and a poly A sequence under the control of a yeast promoter, was digested with Xho I and BamH I to obtain a Xho I-BamH I fragment containing an HSA cDNA region. On the other hand, plasmid pJDB-ADH-HSA-A (Example 8), which contains a DNA coding for prepro HSA wherein the prepro sequence is encoded by codons preferentially used in yeast, was digested with Xho I and BamH I to obtain a larger Xho I-BamH I fragment. Next, these DNA fragments were ligated to construct expression plasmid pJDB-ADH-nHSA-A, wherein a DNA coding for HSA preprosequence by artificially selected codons was replaced by a natural cDNA coding for HSA preprosequence.

*Escherichia coli* HB101/pJDB-ADH-nHSA-A containing the above-mentioned plasmid was deposited with the FRI as FERM BP-2454 under the Budapest Treaty on Jun. 8, 1989.

Example 26

Transformation of yeast host with expression plasmid pJDB-ADH-nHSA-A

Transformation of yeast host cells with an expression plasmid pTDB-ADH-nHSA-A was carried out by a slight modification of the KUR method described by H. Hashimoto and H. Kimura (Hakko To Kogyo, 43, 630–637, 1985). First, 0.1 ml of an overnight preculture of *Sacharomyces cerevisiae* AH22 (MATa, leu 2-3, leu 2-112, his 4-519, Can 1) in YPD medium [2% polypeptone (Difco), 1% yeast extract (Difco) and 2% glucose] was inoculated to 5 ml of YPD medium, and cultured at 30° C. for about 4 hours with shaking until the turbidity at $OD_{600}$ reaches 0.5. The culture was centrifuged at 4° C. for 5 minutes at 2,000 rpm to collect cells, which were then resuspended in 5.0 ml of 0.1M LiSCN, and 1.5 ml of the suspension were centrifuged at 2,000 rpm for 5 minutes, or at 10,000 rpm for one minute. The cells thus obtained were resuspended in 10 µl of 2M LiSCN and 46 µl of 50% PEG 4000. To this suspension were added 10 µl of DNA solution (containing 5 to 10 µg of DNA), and the mixture was incubated at 30° C. overnight. To the suspension 1 ml of sterile distilled water was added, and the whole was gently mixed by a vortex mixer. Next, the suspension was centrifuged at 2,000 rpm for 5 minutes, or at 10,000 rpm for one minute, the collected cells were resuspended in 100 µl of sterile distilled water. The suspension was then spread on a selective a gar plate. [SD medium: 20 µg/ml adenine sulfate, 20 µg/ml arginine hydrochloride, 20 µg/ml methionine, 20 µg/ml histidine hydrochloride, 20 µg/ml tryptophan, 20 µg/ml uracil, 30 µg/ml isoleucine, 30 µg/ml lysine hydrochloride, 30 µg/ml tyrosine, 50 µg/ml phenylalanine, 150 µg/ml valine, 0.15% amino acid-free Yeast Nitrogen Base (Difco), 0.5% ammonium chloride, 2% dextrose and 1.5% agar). The resulting colonies ($Leu^+$) were suspended in 5 ml of SD medium, and cultured at 30° C. for 2 days. The culture was centrifuged at 2,000 rpm for 5 minutes at 4° C. to collect cells, which were then resuspended in 0.5 ml of 1M sorbitol. The suspension was centrifuged to collect cells, which were then resuspended in 0.5 ml of 1M sorbitol, 0.1% 2-mercaptoethanol and 400 µg/ml Zymolyase-100T (Seikagaku Kogyo). The suspension was incubated at 30° C. for 30 minutes to form spheroplasts which were then centrifuged at 2,000 rpm for 5 minutes. The collected spheroplasts were resuspended in 100 µl of solution I (50 mM glucose, 10 mM EDTA and 25 mM Tris-HCl, pH 8.0), and after the addition of 200 µl of solution II (0.2N NaOH, 1% SDS), the suspension was thoroughly mixed and put on ice for 5 minutes. To the suspension were added 150 µl of 5M potassium acetate, and the suspension was thoroughly mixed, and after putting on ice for 10 minutes, centrifuged at 15,000 rpm for 5 minutes at 4° C. to obtain the supernatant, which was then transferred to a fresh tube. To the supernatant an equal volume of phenol/chloroform (1:1) was added, and the whole was violently mixed and centrifuged at 12,000 rpm for 5 minutes to obtain an aqueous layer, which was then transferred to a fresh tube. To the aqueous layer were added 750 µl of ethanol, and the mixture was thoroughly mixed by a vortex mixer. The mixture was centrifuged at 15,000 rpm for 5 minutes to obtain a precipitate, to which 0.5 ml of 70% ethanol were added. The mixture was mixed by a vortex mixer, and centrifuged at 15,000 rpm for 5 minutes to obtain a precipitate. The DNA precipitate thus obtained was dried under a reduced pressure, and dissolved in 30 µl of TE buffer. The DNA preparation obtained from the AH22 transformants containing plasmid pJDB-ADH-nHSA-A was digested with various restriction enzymes, such as Hind III, Xho I, EcoR I, BamH I and Sal I alone or in combination, and the resulting fragments were analyzed by agarose gel electrophoresis and polyacrylamide gel electrophoresis to confirm the structure of the plasmid.

Example 27

Production of HSA by transformants

A single colony formed on an SD (-Leu) plate was suspended in 5.0 ml of fresh SD (-Leu) liquid medium and cultured at 30° C. for 2 days with shaking until an $OD_{600}$ reached about 2.0. One hundred microliters of the culture were added to 5.0 ml of YPD medium, and cultured at 30° C. for 24 hours until an $OD_{600}$ reached about 3.0. The culture was centrifuged at 5,000 rpm for 10 minutes at 4° C. to obtain the supernatant fraction. To the supernatant fraction was added an equal volume of 99% ethanol, and the whole was mixed and allowed to stand for 30 minutes at 4° C. Next, the mixture was centrifuged at 12,000 rpm for 10 minutes at 4° C. to obtain a precipitate. The precipitate was dissolved in 100 µl of 1×loading buffer (5% 2-mercaptoethanol, 0.0025% bromophenol blue, 2% SDS, 0.025M Tris-HCl and 8% glycerol), and 10 µl of the solution were applied to an electrophoretic gel [SDS-polyacrylamide gel; 4 to 20% concentration gradient; 84 mm (width)×90 mm (height)×1.0 mm (thickness)]. Electrophoresis was carried out in an electrophoresis buffer (0.025M Tris-HCl, pH 8.4, 0.192M glycine and 0.1% SDS) at a constant current of 60 mA for 60 minutes. As the molecular weight (MW) markers, egg white lysozyme (MW 14,400), soybean trypsin inhibitor (MW 21,500) carbonic anhydrase (MW 31,000), ovalbumin (MW 45,000), bovine serum albumin (MW 66,200), and phosphorylase B (MW 92,500), all obtained from BIO-RAD, were used. After the electrophoresis, proteins in the gel were stained with Coomassie Brilliant Blue, or as described hereinafter, immunologically detected after Western blotting. After the electrophoresis, the separated proteins were transferred to a nitrocellulose filter (BIO-RAD) using a semi-dry blotter (Sartorius). Namely, the filter was soaked in methanol for one hour and then in 25 mM Tris-HCl (pH 10.4)/20% methanol, and attached to an electrophoretic gel. This was sandwiched with filter papers which had been soaked in the above-mentioned buffer, and 0.3M Tris-HCl (pH 10.0) containing 20% methanol and 25 mM Tris-HCl (pH 9.4)/40 mM 6-amino-n-capronic acid, and was applied to the blotter. After applying a constant voltage of 6 V for about 1.5 hours, the filter was washed by shaking it in a solution of 20 mM Tris-HCl (pH 7.5)/500 mM NaCl (TBS) containing 3% gelatin at 37° C. for one hour, and then in TBS/0.05% Tween-20 for 5 minutes. Next, the filter was shaken in 40 ml containing solution containing anti-human serum albumin rabbit antibody (Cappel) which had been diluted 2,000-fold with TBS containing 1% gelatin, at room temperature overnight. The filter was washed with TBS (pH 7.5) containing 0.05% Tween-20 (T-TBS) while shaking. This procedure was once repeated. The filter was then shaken in 40 ml of a solution of a secondary antibody (goat anti-rabbit IgG antibody labeled with horseradish peroxidase; BIO-RAD) which had been diluted 3,000-fold with TBS containing 1% gelatin, for one hour at a room temperature. Next, the filter was washed twice with T-TBS for 5 minutes and once with TBS for 5 minutes as described above. The filter was soaked in a mixture of 10 ml of methanol containing 30 mg of 4-chloronaphtol 50 ml TBS and 30 µl of 30% hydrogen peroxide to detect a band corresponding to HSA, and the developing reaction was terminated by diluting with distilled water.

Example 28

Figure 31:
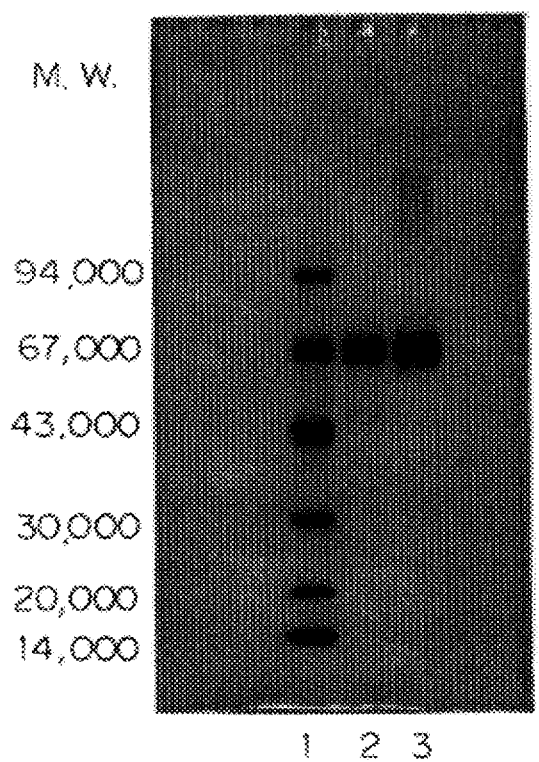
FIG. 31 shows a result of electrophoresis wherein HSA produced by culturing a transformant AH22 (pJDB-ADH-nHSA-A) containing HSA cDNA was subjected to SDS-polyacrylamide gel electrophoresis, and detected by Coomassie Brilliant Blue staining.

Biochemical homology between HSA produced by yeast transformants and HSA prepared from human serum (1) Molecular weight A sample of HSA isolated from a yeast culture was reduced with 2-mercaptoethanol, treated with SDS, and applied to a 12%–30% polyacrylamide gradient gel in SDS, and electrophoresis was carried out under the conditions described by Laemmli, U.K., Nature, 227, 680–685, 1970. As molecular weight markers, phosphorylase B (MW 94,000), bovine serum albumin (MW 67,000), ovalbumin (MW 43,000), carbonic anhydrase (MW 30,000), soybean trypsin inhibitor (MW 20,000), and lactoalbumin (MW 14,000) were used. Proteins were detected by Coomassie Brilliant Blue staining. Simultaneously, as a control, a commercially available HSA purified from human serum was run, and the mobility of both HSAs were compared. As a result, HSA produced by yeast transformants and HSA derived from human serum exhibited the same mobility, and their molecular weight was 67,000, as shown in FIG. 31.

Figure 32:
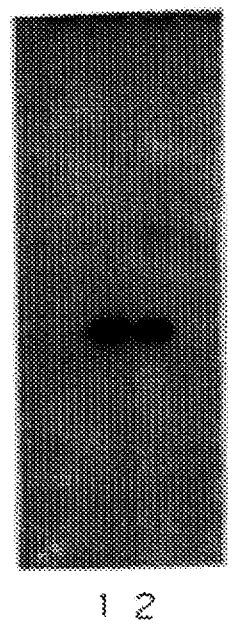
FIG. 32 shows a result of a comparison of HSA produced by yeast transformant and HSA prepared from human serum, by native poly acrylamide gradient gel electrophoresis.

(2) Electrophoketic properties Native gel electrophoresis (FIG. 32)

An HSA preparation isolated from yeast culture was suspended in 62.5 mM Tris-HCl (pH 6.8), 15% glycerol, 0.001% bromophenol blue, and electrophoresis was carried out using a 4–15% polyacrylamide concentration gradient gel (pH 8.4) according to a method of Davis, R. J., Amm. N.Y. Acad. Sci. 121, 401, 1964. The result was compared with that of a commercially available HSA purified from human serum. HSA isolated from yeast culture exhibited the same electrophoretic profile as that of HSA purified from human serum.

(3) Isoelectric focusing

Figure 33:
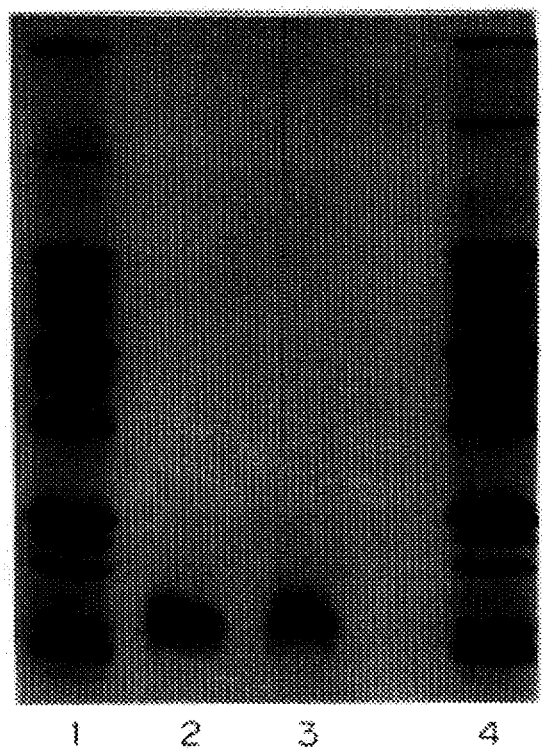
FIG. 33 shows a result of a comparison of HSA produced by yeast transformants and HSA prepared from human serum, by isoelectroic focusing.
Figure 34:
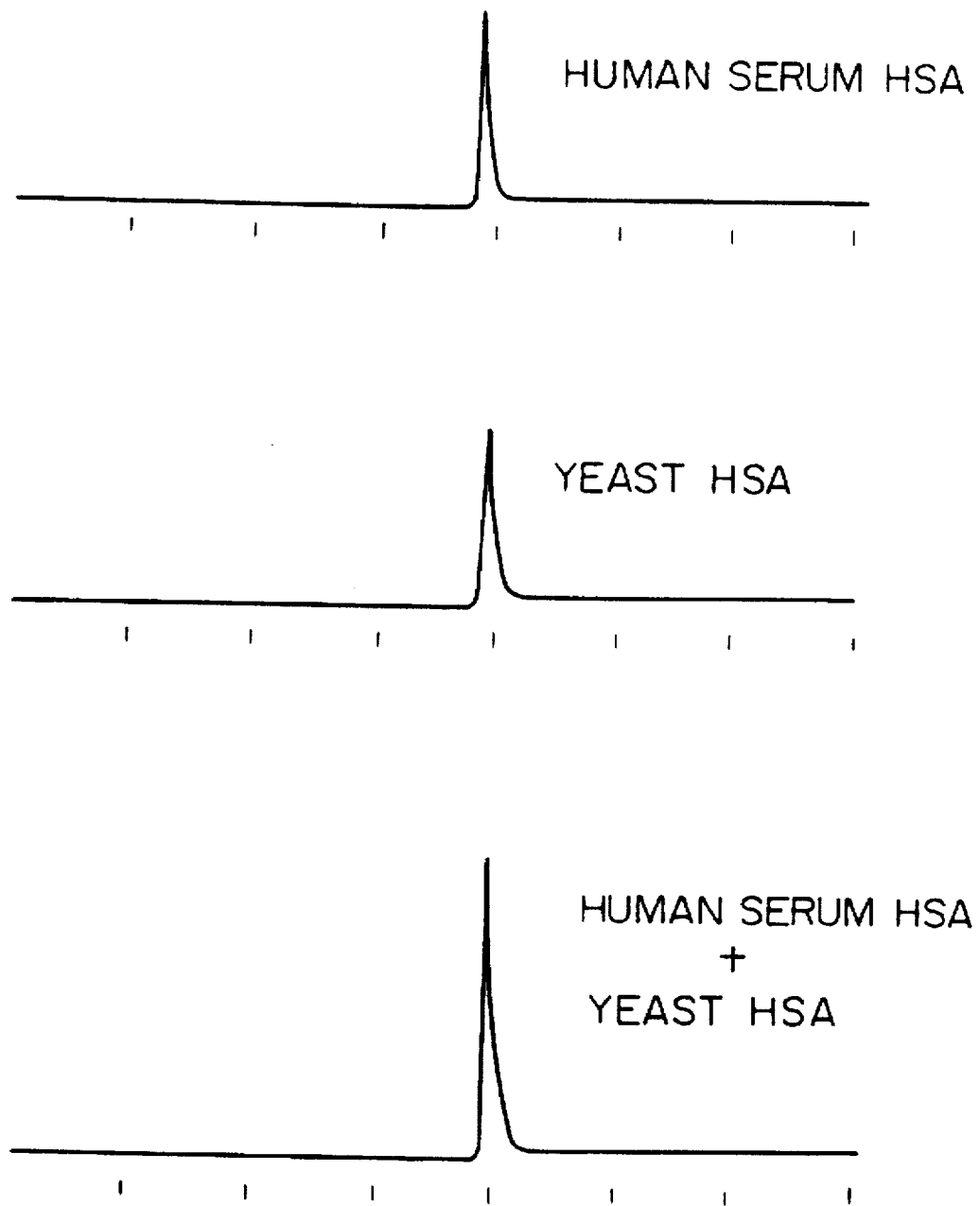
FIG. 34 shows a result of a comparison of HSA produced by yeast transformants and HSA prepared from human serum, by reverse phase HPLC.

Isoelectric focusing was carried out using an Ampholine PAG plate, pH range 3.5–9.5 (LKB) according to the maker's manual. As isoelectric point markers, LKB's PI markers, i.e., C-phycocyanin (pI 4.75, 4.85), azurin (pI 5.65), trifluoroacetylated myoglobin (porcine pI 5.9), myoglobin (porcine pI 6.45), myoglobin (horse pI 7.3); myoglobin (whale pI 8.3), and cytocrome C (pI 10.6) were used. HSA produced by yeast transformants exhibited several bands between pI 4.8 and pI 5.2, which were the same as HSA purified from human serum. This result is set forth in FIG. 33.

(4) Determination of N-terminal amino acid sequence

The N-terminal amino acid sequence of HSA (20 µg) produced by yeast transformants was determined using gas phase protein sequencer 477 A (Applied Biosystems) according to the maker's manual. As a result, an amino acid sequence from the amino-terminus was Asp-Ala-His-Lys-Ser-Glu-Val-Ala-His-Arg, which was completely identical with the reported amino acid sequence from the amino-terminal amino acid sequence of HSA. Calculating from the recovery of N-terminal amino acids, it was estimated that the HSA preparation tested had an N-terminal homogeneity of at least 95%. From this result, the absence of prepro HSA sequence due to incomplete processing was confirmed.

(4) Determination of C-terminal amino acid sequence

The C-terminal amino acid sequence was determined as follows.

Preparation of C-terminal fragment

First, 8 mg (about 120 nmol) of HSA produced by yeast transformants was cleaved with cyanogen bromide according to the method of E. Steers et al., J. Biol. Chem., 240, 2478, and SH groups in the fragments were reductively carboxymethylated to form S—S bond-free cyanogen bromide-cleavage products according to the method of Hirs, C. H. W. in Methods in Engymology Academic Press, New York, Vol. 11 199 (1967). Next, the reaction mixture was subjected to reverse phase column chromatography using a Cosmosil Packed Column 5C8-300 (4.6 I.D.×250 mm) (Nakarai Tesk) to obtain a peptide fragment containing the C-terminus of HSA. The fragment was identified by determining the N-terminal amino acid sequence thereof. Then 7.4 nmol of the fragment thus obtained were dissolved in 10 µl of 50 mM Tris-HCl (pH 8.0) containing 20 mH $CaCl_2$, and to the solution were added 0.5 µg of DPCC-trypsin (Sigma). The mixture was incubated at room temperature for 5 hours to digest the fragment, and from the digest, 5.0 nmol of peptide fragment were obtained by reverse phase column chromatography using TSK-gel ODS-120T (4.6 I.D.×120 mm; Toso). On the basis of the data obtained by sequencing of the fragment, which was started from the N-terminus and analysis of amino acid composition, the amino acid sequence of this fragment was assumed to be Leu-Val-Ala-Ala-Ser-Gln-Ala-Ala-Leu-Gly-Leu, which corresponds to 11 amino acid residues of C-terminus of HSA.

Identification of C-terminus using carboxypeptidase P

First, 2 nmol of the fragment thus obtained were divided into 4 portions of 0.5 nmol, which were put into 4 test tubes.

Each portion was dissolved in 10 μl of sodium acetate buffer (pH 6.5), and digested with 12 ng of carboxypeptidase P (Takara Shuzo). Four mixtures were boiled at 0, 30, 60 and 120 minutes after the start of the reaction, respectively, to terminate the reaction. The released amino acids were PTC-derivatized, and identified by HPLC using a 130 A separation system (Applied Biosystems). As a result, at 0 minute, 517 pmol Leu, 65 pmol Gly and 13 pmol Ala; at 30 minutes, 658 pmol Leu, 100 pmol Gly, and 18 pmol Ala; at 120 minutes, 682 pmol Leu, 77 pmol Gly, and 16 pmol Ala; and at 120 minutes, 840 pmol Leu, 121 pmol Gly, and 31 pmol Ala, were detected. From this result it was confirmed that the fragment has an amino acid sequence Leu-Gly- from its C-terminus. Taking into account of the results described above and of the determination of the amino acid sequence of the fragment as well as the amino acid composition analysis, it was confirmed that the C-terminal amino acid sequence of yeast-produced HSA was identical with that of natural HSA.

(5) Behavior on HPLC

Reverse phase column chromatography As an HPLC apparatus, Shimazu LC-6A Type Gradient LC system equipped with TSK-gel Phenyl 5PW RP column was used. The column was equilibrated with 0.1% trifluoroacetic acid, and HSA produced by yeast transformants, a commercial HSA purified from human serum, and a mixture thereof were separately applied. Elution of the proteins were carried out using an acetonitrile concentration gradient from 0% to 70% in 0.1% trifluoroacetic acid for 60 minutes at a flow rate of 1 ml/minute.

Figure 35:
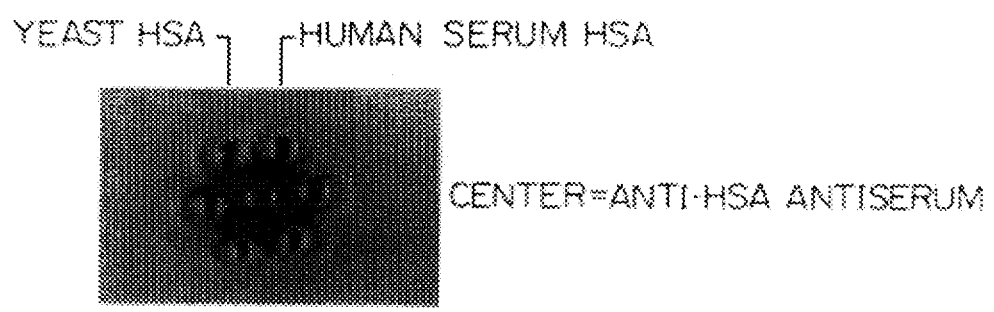
FIG. 35 shows a result of a comparison of HSA produced by yeast transformants and HSA prepared from human serum, by the Ouchterlony method.
Figure 36:
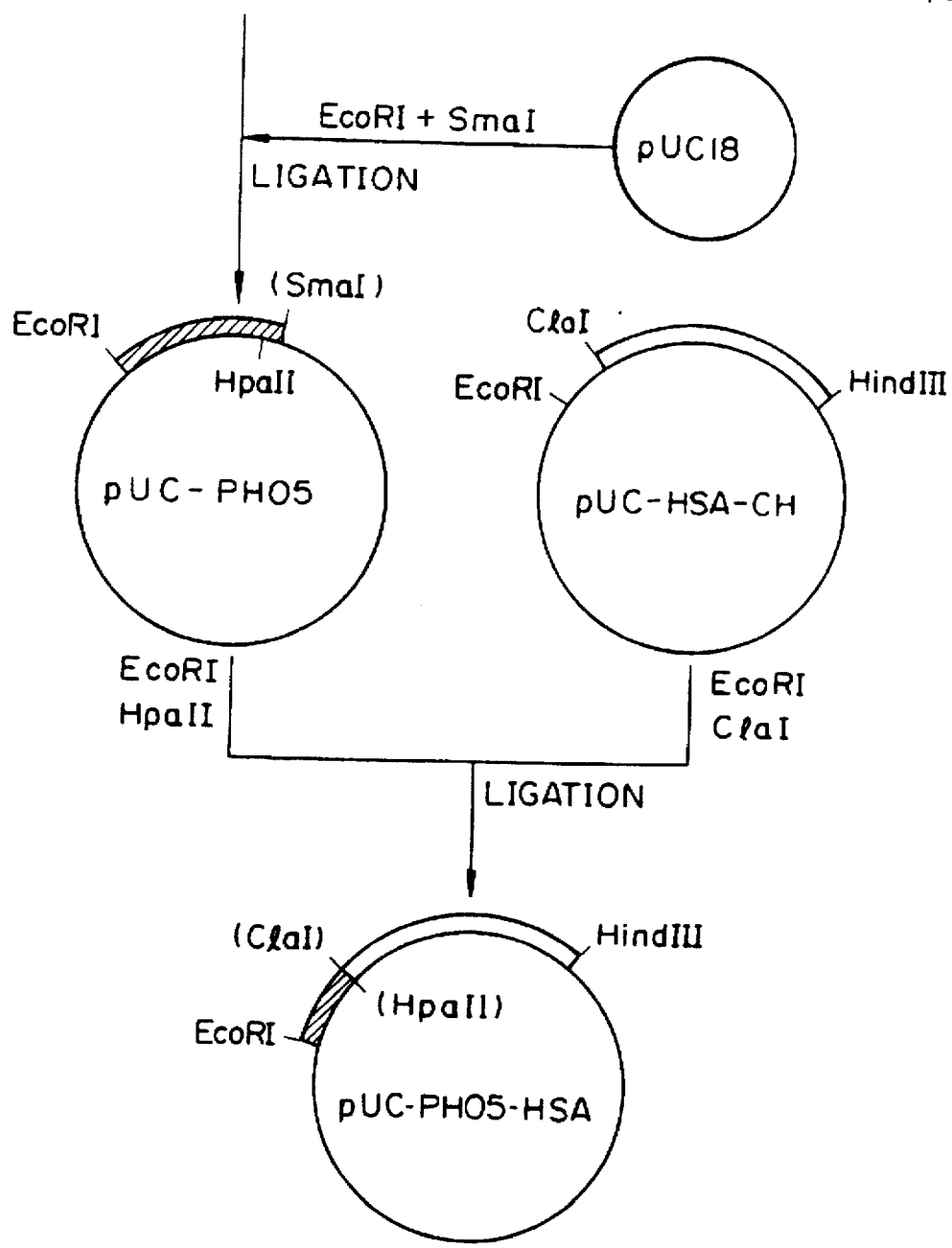
FIG. 36 shows a process for the construction of plasmid pUC-PH05-HSA.

Under these conditions, HSA produced by the yeast transformants provided a single sharp peak whose retention time and shape were indistinguishable from those of HSA purified from human serum. Moreover, where these two HSAs were mixed and the mixture was chromatographed, on the column, the mixture provided a single sharp peak, indicating that the behavior of these two HSAs on the reverse phase column was absolutely identical. The result is set forth in FIG. 35.

Example 29

Synthesis of DNA coding for acid phosphatase (PH05) signal peptide

Two oligonucleotides having the following sequences:

5'-AATTCATGTTTAAATCTGTTGTTTATTCAATTTTAGCCGCTTC-TTTGGCCAATGCCGGC
5'-GCCGGCATTGGCCAAAGAAGCGGCTAAAATTGAATAAACAACA-GATTTAAACATG were synthesized using an automatic DNA synthesizer (Applied Biosystems Model 380B) by the phosphoamidite method (Matteucci, M. D. & Caruthers, M. H. Tetrahedron Letters 21,719 (1980)). These two oligonucleotides were annealed to obtain a double-stranded DNA coding for the acid phosphatase signal peptide. This double-stranded DNA had the following sequence.

| | Met | Phe | Lys | Ser | Val | Val | Tyr | Ser |
|---|---|---|---|---|---|---|---|---|
| AA | TTC ATG | TTT | AAA | TCT | GTT | GTT | TAT | TCA |
| | G TAC | AAA | TTT | AGA | CAA | CAA | ATA | AGT |
| EcoR I | | | | | | | | |

| Ile | Leu | Ala | Ala | Ser | Leu | Ala | Asn | Ala | Gly |
|---|---|---|---|---|---|---|---|---|---|
| ATT | TTA | GCC | GCT | TCT | TTG | GCC | AAT | GCC | GGC |
| TAA | AAT | CGG | CGA | AGA | AAC | CGG | TTA | CGG | CCG |
| | | | | | | | | | HpaII |

The DNA had an EcoR I cohesive end at the 5'-terminus, and Nae I or Hpa II blunt end at the 3'-terminus. To provide Nae I and Hpa II sites at the 3'-terminus, codons for Ala-Gly were changed (GCA→GCC; GGT→GGC). The signal peptide of acid phosphatase extended to the 17th Ala.

Example 30

Figure 37:
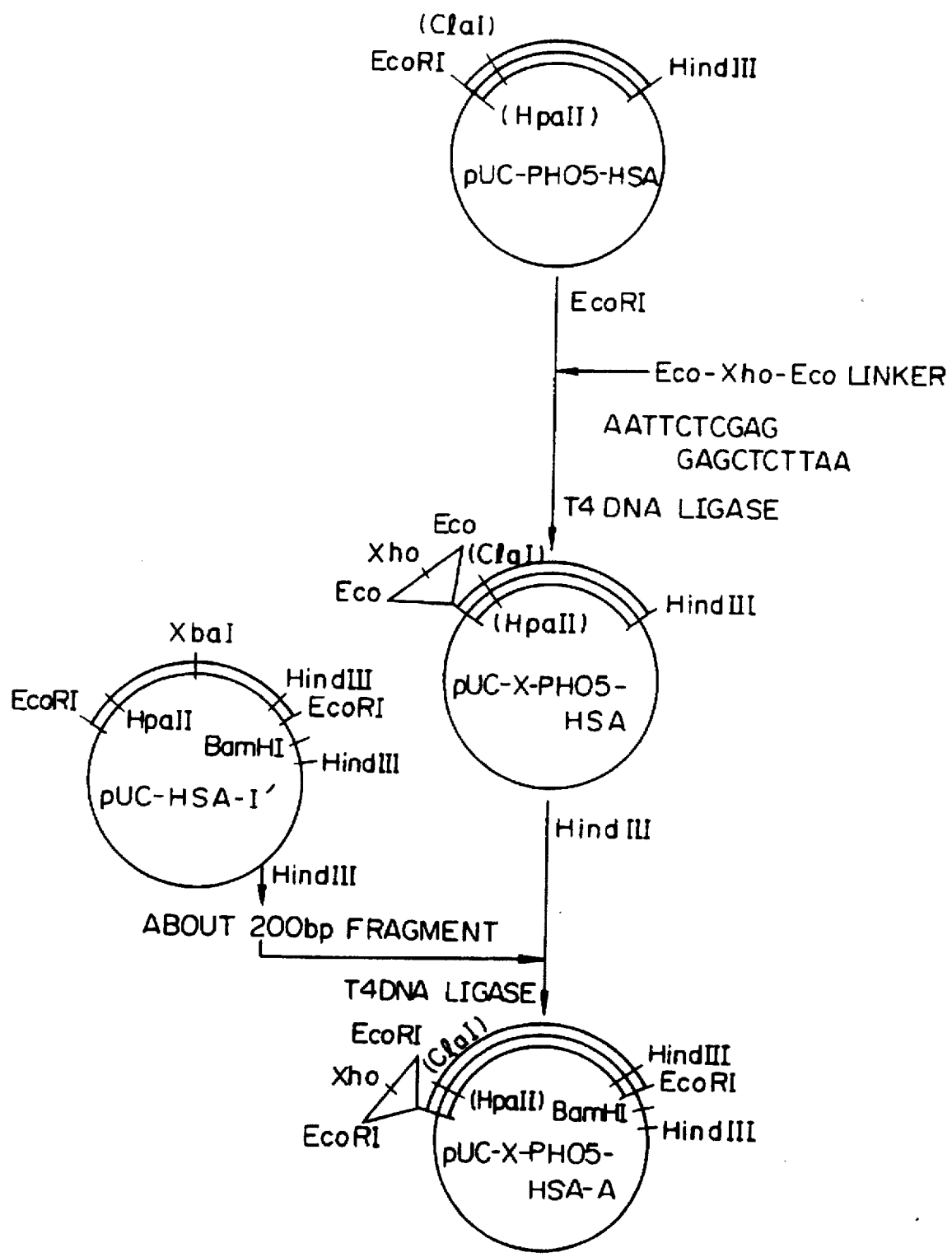
FIG. 37 shows a process for the construction of plasmid pUC-X-PH05-HSA-A.

Ligation of synthetic DNA coding for acid phosphatage signal peptide and cDNA coding for mature HSA (FIG. 37)

The synthetic DNA coding for the acid phosphatase signal peptide was phosphorylated at its 5'-terminus using T4 polynucleotide kinase, and plasmid pUC18 was cleaved at its multi-cloning site by EcoR I and Sma I to obtain a 2.6 kb fragment. These DNA fragments were ligated to construct plasmid pUC-PH05. This plasmid was doubled-digested with EcoR I and Hpa II to obtain a 55 bp DNA fragment coding for the acid phosphatase signal peptide. Recombinant plasmid pUC-HSA-CH (Reference Example 2), containing the entire structural gene for mature HSA and the 3'-nonecoding region in pUC18, was double-digested with EcoR I and Cla I to obtain a 4.4 kb DNA fragment. These DNA fragments were ligated to construct recombinant plasmid pUC-PH05-HSA.

Example 31

Figure 38:
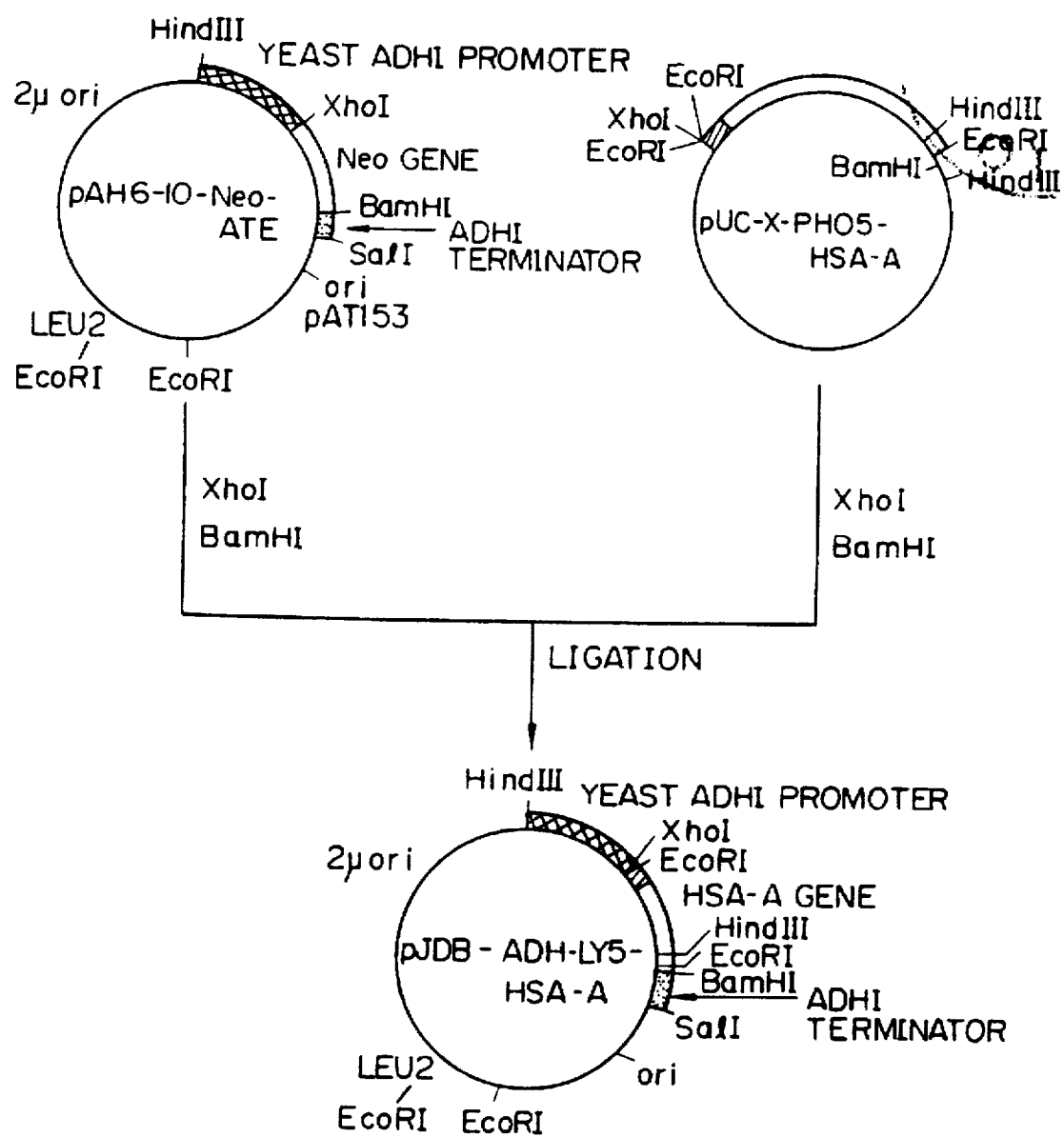
FIG. 38 shows a process for the construction of plasmid pJDB-ADH-LY5-HSA-A.
Figure 39:
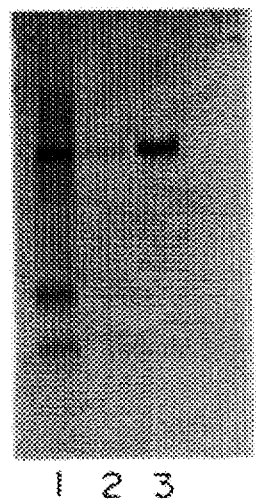
FIG. 39 shows a Western blot of the extracts from yeast cells transformed with the present expression plasmid pJDB-ADH-LY5-HSA-A (lane 1), the supernatant thereof (lane 2), and HSA prepared from human serum as a control.

Construction of expression plasmid (FIGS. 38 and 39)

A synthetic linker (Eco-Xho-Eco linker) of the following sequence:

5'-AATTCTCGAG-3' 3'-GAGCTCTTAA-5' having EcoR I ends and an internal Xho I site was inserted into plasmid pUC-PH05-HSA at its EcoR I site to construct plasmid pUC-X-pH05-HSA. Plasmid pUC-HSA-I' (Example 3) was digested with Hind III to obtain a Hind III fragment of about 200 bp containing the 3'-non-coding region of HSA cDNA containing a poly A addition signal and a poly A sequence. This DNA fragment was inserted to plasmid pUC-X-PH05-HSA at its Hind III site downstream of the structural gene to obtain pUC-X-PH05-HSA-A, and this plasmid pUC-X-PH05-HSA-A was double-digested with Xho I and BamH I to obtain a 2.0 kb DNA fragment. A yeast expression vector pAH6-10-Neo-ATE (Example 7), containing ADCI promoter and terminator, was double-digested with Xho I and BamH I to obtain an 8.1 kb DNA fragment. These fragments were ligated to construct expression plasmid pJDB-ADH-LY5-HSA-A.

*Escherichia coli* HB101/pJDB-ADH-LY5-HSA-A containing said expression plasmid was deposited with the FRI as FERM BP-2456 under the Budapest Treaty on Jun. 8, 1989.

Example 32

Transformation of yeast host with expression plasmid pJDB-ADH-LY5-HSA-A

Transformation of yeast host cells with an expression plasmid pJDB-ADH-LY5-HSA-A was carried out by a slight modification of the KUR method described by H. Hashimoto and H. Kimura (Hakko To Kogyo, 43, 630–637, 1985). First 0.1 ml of an overnight preculture of *Saccharomyces cerevisiae* AH22 (MATa, leu 2-3, leu 2-112, his 4-519, Can 1) medium [2% polypeptone (Difco), 1% yeast extract (Difco) and 2% glucose] was inoculated to 5 ml of YPD medium, and cultured at 30° C. for about 4 hours with shaking until the turbidity at $OD_{600}$ reaches 0.5. The culture was centrifuged at 4° C. for 5 minutes at 2,000 rpm to collect cells, which were then resuspended in 5.0 ml of 0.1M LiSCN, and 1.5 ml of the suspension was centrifuged at 2,000 rpm for 5 minutes, or at 10,000 rpm for one minute. The cells thus obtained were resuspended in 10 µl of 2M LiSCN and 46 µl of 50% PEG 4000. To this suspension were added 10 µl of DNA solution (containing 5 to 10 µg of DNA), and the mixture was incubated at 30° C. overnight. To the suspension 1 ml of sterile distilled water was added, and the whole was gently mixed by a vortex mixer. Next, the suspension was centrifuged at 2,000 rpm for 5 minutes, or at 10,000 rpm for one minute, and the collected cells were resuspended in 100 µl of sterile distilled water. The suspension was then spread on a selective a gar plate [SD medium: 20 µg/ml adenine sulfate, 20 µg/ml arginine hydrochloride, 20 µg/ml methionine, 20 µg/ml histidine hydrochloride, 20 µg/ml tryptophan, 20 µg/ml uracil, 30 µg/ml isoleucine, 30 µg/ml lysine hydrochloride, 30 µg/ml tyrosine, 50 µg/ml phenylalanine, 150 µg/ml valine, 0.15% amino acid-free Yeast Nitrogen Base (Difco), 0.5% ammonium chloride, 2% dextrose and 1.5% agar). The resulting colonies (Leu+) were suspended in 5 ml of SD medium, and cultured at 30° C. for 2 days. The culture was centrifuged at 2,000 rpm and for 5 minutes at 4° C. to collect cells, which were then resuspended in 0.5 ml of 1M sorbitol. The suspension was centrifuged to collect cells, which were then resuspended in 0.5 ml of 1M sorbitol, 0.1% 2-mercaptoethanol and 400 µg/ml Zymolyase-100T (Seikagaku Kogyo). The suspension was incubated at 30° C. for 30 minutes to form spheroplasts which were then centrifuged at 2,000 rpm for 5 minutes. The collected spheroplasts were resuspended in 100 µl of solution I (50 mM glucose, 10 mM EDTA and 25 mM Tris-HCl, pH 8.0), and after the addition of 200 µl of solution II (0.2N NaOH, 1% SDS), the suspension was thoroughly mixed and put on ice for 5 minutes. To the suspension were added 150 µl of 5M potassium acetate, and the suspension was thoroughly mixed, and after putting on ice for 10 minutes, centrifuged at 15,000 rpm for 5 minutes at 4° C. to obtain the supernatant, which was then transferred to a fresh tube. To the supernatant an equal volume of phenol/chloroform (1:1) was added, and the whole was violently mixed and centrifuged at 12,000 rpm for 5 minutes to obtain an aqueous layer, which was then transferred to a fresh tube. To the aqueous layer were added 750 µl of ethanol, and the mixture was thoroughly mixed by a vortex mixer. The mixture was centrifuged at 15,000 rpm for 5 minutes to obtain a precipitate, to which 0.5 ml of 70% ethanol were added. The mixture was mixed by a vortex mixer, and centrifuged at 15,000 rpm for 5 minutes to obtain a precipitate. The DNA precipitate thus obtained was dried under a reduced pressure and dissolved in 30 µl of TE buffer. The DNA preparation obtained from the AH22 transformants containing plasmid pJDB-ADH-LY5-HSA-A was digested by various restriction enzymes, such as Hind III, Xho I, EcoR I, BamH I and Sal I alone or in combination, and the resulting fragments were analyzed by agarose gel electrophoresis and polyacrylamide gel electrophoresis to confirm the structure of the plasmid.

Example 33

Production of HSA by transformants (FIG. 40)

A single colony formed on an SD (-Leu) plate was suspended in 5.0 ml of fresh SD (-Leu) liquid medium and cultured at 30° C. for 2 days with shaking until an $OD_{600}$ value reached about 2.0. One hundred microliters of the culture were added to 5.0 ml of YPD medium, and cultured at 30° C. for 24 hours until an $OD_{600}$ reached about 3.0. The culture was centrifuged at 5,000 rpm for 10 minutes at 4° C. to obtain the supernatant fraction. To the supernatant fraction was added an equal volume of 99% ethanol, and the whole was mixed and allowed to stand for 30 minutes at 4° C. Next, the mixture was centrifuged at 12,000 rpm for 10 minutes at 4° C. to obtain a precipitate. The precipitate was dissolved in 100 µl of 1×loading buffer (5% 2-mercaptoethanol, 0.0025% bromophenol blue, 2% SDS, 0.025M Tris-HCl and 8% glycerol), and 10 µl of the solution were applied to an electrophoretic gel [SDS-polyacrylamide gel; 4 to 20% concentration gradient; 84 mm (width)×90 mm (height)×1.0 mm (thickness)]. Electrophoresis was carried out in an electrophoresis buffer (0.025M Tris-HCl, pH 8.4, 0.192M glycine and 0.1% SDS) at a constant current of 60 mA for 60 minutes. As the molecular weight (MW) markers, egg white lysozyme (MW 14,400), soybean trypsin inhibitor (MW 21,500) carbonic anhydrase (MW 31,000), ovalbumin (MW 45,000), bovine serum albumin (MW 66,200), and phosphorylase B (MW 92,500), all obtained from BIO-RAD, were used. After the electrophoresis, proteins in the gel were stained with Coomassie Brilliant Blue, or as described hereinafter, immunologically detected after Western blotting. After the electrophoresis, the separated proteins were transferred to a nitrocellulose filter (BIO-RAD) using a semi-dry blotter (Sartorius). Namely, the filter was soaked in methanol for one hour and then in 25 mM Tris-HCl (pH 10.4)/20% methanol, and attached to an electrophoretic gel. This was sandwiched with filter papers which had been soaked in the above-mentioned buffer, and 0.3M Tris-HCl (pH 10.0) containing 20% methanol and 25 mM Tris-HCl (pH 9.4)/40 mM 6-amino-n-capronic acid, and was applied to the blotter. After applying a constant voltage of 6 V for about 1.5 hours, the filter was washed by shaking it in a solution of 20 mM Tris-HCl (pH 7.5)/500 mM NaCl (TBS) containing 3% gelatin at 37° C. for one hour, and then in TBS/0.05% Tween-20 for 5 minutes. Next, the filter was shaken in 40 ml of a solution containing anti-human serum albumin rabbit antibody (Cappel) which had been diluted 2,000-fold with TBS containing 1% gelatin, at room temperature overnight. The filter was washed with TBS (pH 7.5) containing 0.05% Tween-20 (T-TBS) while shaking. This procedure was once repeated. The filter was then shaken in 40 ml of a solution containing a secondary antibody (goat anti-rabbit IgG antibody labeled with horseradish peroxidase; BIO-RAD) which had been diluted 3,000-fold with TBS containing 1% gelatin, for one hour at room temperature. Next, the filter was washed twice with T-TBS for 5 minutes and once with TBS for 5 minutes as described above. The filter was soaked in a mixture of 10 ml methanol containing 30 mg of 4-chloronaphtol, 50 ml TBS and 30 μl of 30% hydrogen peroxide to detect a band corresponding to HSA, and the developing reaction was terminated by diluting with distilled water. The result is set forth in FIG. 40.

Reference Example 1

Screening of clones containing CDNA coding for normal human serum albumin A

A human liver CDNA library constructed using a vector phage λgt11 commercially available from Clontech, U.S.A. was used to select the clones containing a cDNA fragment coding for human normal serum albumin A by plaque hybridization. The λgt11 recombinant phages in the library were used for infection to *E. coli* Y1090, which was then plated on LB agar solid medium to form $5.5 \times 10^5$ transformant plaques. Recombinant DNAs in the plaques were transferred onto membrane filters (Hybond-N; Amersham), and screened using three synthetic oligonucleotide probes labeled with 32P (specific radioactivity $\geq 10^7$ cpm/μg) by the method of Benton and Davis, Science, 196, 180–182 (1977). These three probes are probe HSA-1 corresponding to the 5'-non-coding region and the 5'-coding region starting 12 base-pairs upstream from ATG start codon and ending at in the codon for 9th amino acid leucine; probe HSA-2 coding for 248th glycine to 260th leucine; and probe HSA-3 comprising the 3'-terminal coding region and 3'-terminal non-coding region starting with the codon for 576th valine and ending 9 nucleotides downstream from the C-terminal leucine codon, all sequences described by Lawn et al., Nucleic Acids Res. 9, 6103–6114 (1981). The nucleotide sequences used as probes were on the complementary or negative strand. The nucleotide sequences of these three probes are shown in FIG. 5. These oligonucleotide probes were synthesized by an automatic DNA synthesizer, and labeled using [γ-$^{32}$p] ATP and polynucleotide kinase. Among 200 λgt11 clones which gave a positive signal with the probe HSA-2, from 4 clones, DNA was prepared by the method of Blattner et al., Science, 202, 1279–1284 (1978), and digested with EcoR I, and a Southern blot of the digested product was allowed to hybridize with the probe HSA-2 by the method of Southern, J. Mol. Biol. 98, 503–517 (1975). DNA fragments having a size of 1.8 Kb, 1.4 kb, and 1.3 Kb, respectively, were hybridized with the probe HSA-2. Among these, DNA fragments of 1.8 Kb and 1.3 Kb were subcloned in vector pUC19, and these subclones were subjected to colony hybridization using probes HSA-1 and HSA-3, by the method of Grunstein and Hogness Proc. Natl. Acad. Sci. U.S.A., 72, 3961–3965 (1975). As a result, a clone λgt11 (HSAI-A) which was hybridized with only HSA-3 was obtained. DNA in this clone was digested with various restriction enzymes, and the resulting DNA fragments were inserted into phage vectors M13mp18 and M13mp19 RF DNA, and the nucleotide sequence of the DNA was determined by the dideoxy chain termination method of Sanger, F., Nicklen, S. and Coulson, A. R. Proc. Natl. Acad. Sci, U.S.A., 74, 5463–5467 (1977).

On the other hand, among the clones which gave a positive signal in plaque hybridization of λgt11 clones using the HSA-2 probe, 20 clones were subjected to plaque hybridization using the HSA-1 probe, and a positive clone λgt11 (HSA-II) was obtained. From this clone, phage DNA was prepared and digested with EcoR I. The digestion products was subjected to Southern hybridization using the HSA-I probe, and a DNA fragment of 1.25 Kb designated HSA-II was found to hybridize with the HSA-I probe. The nucleotide sequence of this DNA fragment was determined by dideoxy chain termination method. The HSA-II did not hybridize with the HSA-3 probe.

As a result, it was found that the HSA-II lacks a DNA portion coding for the C-terminal region of human serum albumin, and the HSA-I-A lacks a DNA portion coding for the N-terminal region of human serum albumin and containing an opal codon TGA as a stop codon in place of the codon TCA coding for 304th serine. Restriction enzyme cleavage maps of these DNA fragments are shown in FIG. 1. In these maps, exact positions of restriction enzyme recognitions sites were obtained from the finally determined nucleotide sequence.

Figure 8:
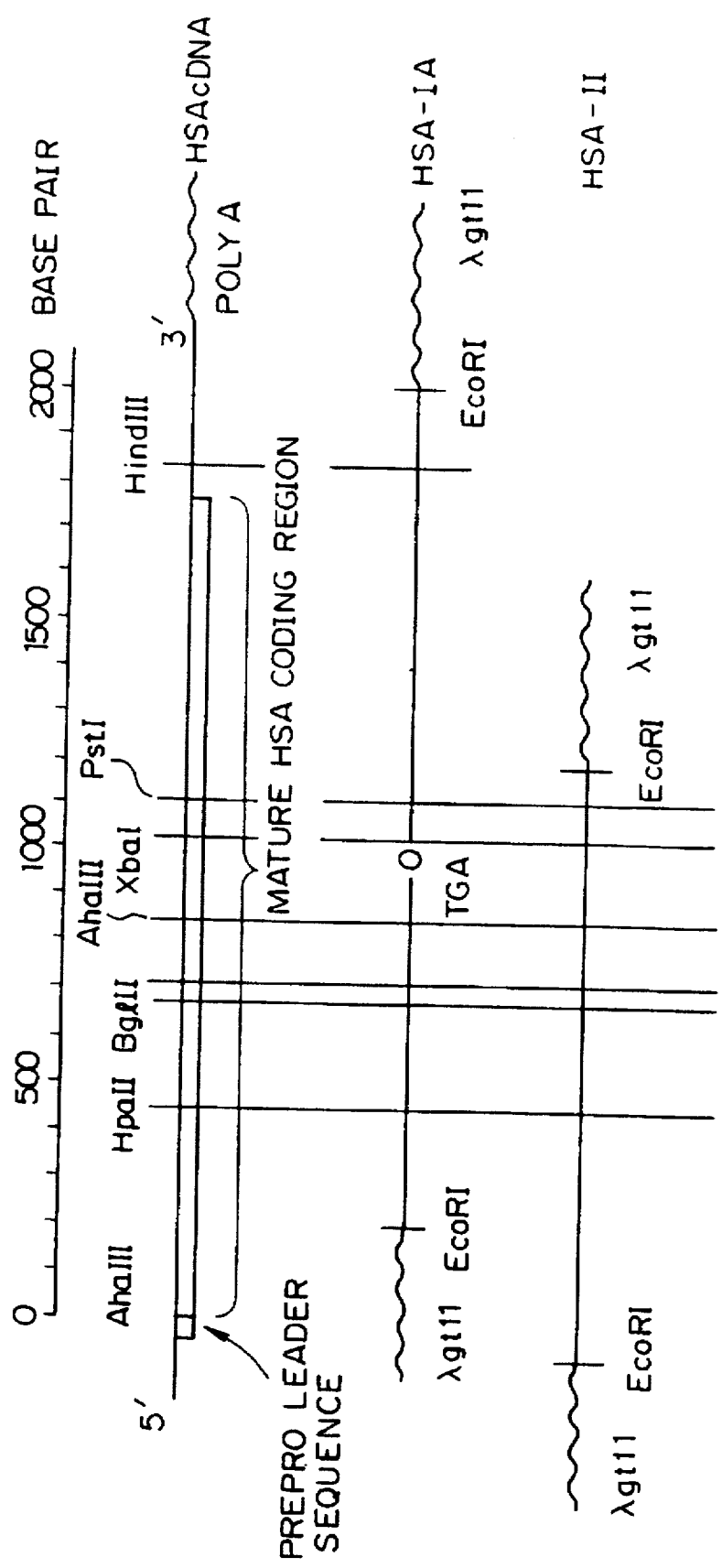
FIG. 8 shows a cDNA (HSAcDNA) coding for the entire normal human serum albumin A, as well as a cDNA (HSA-IA) coding for the C-terminal portion of HSA and cDNA (HSA II) coding for the N-terminal portion of HSA, used for the construction of the entire cDNA.
Figure 10:
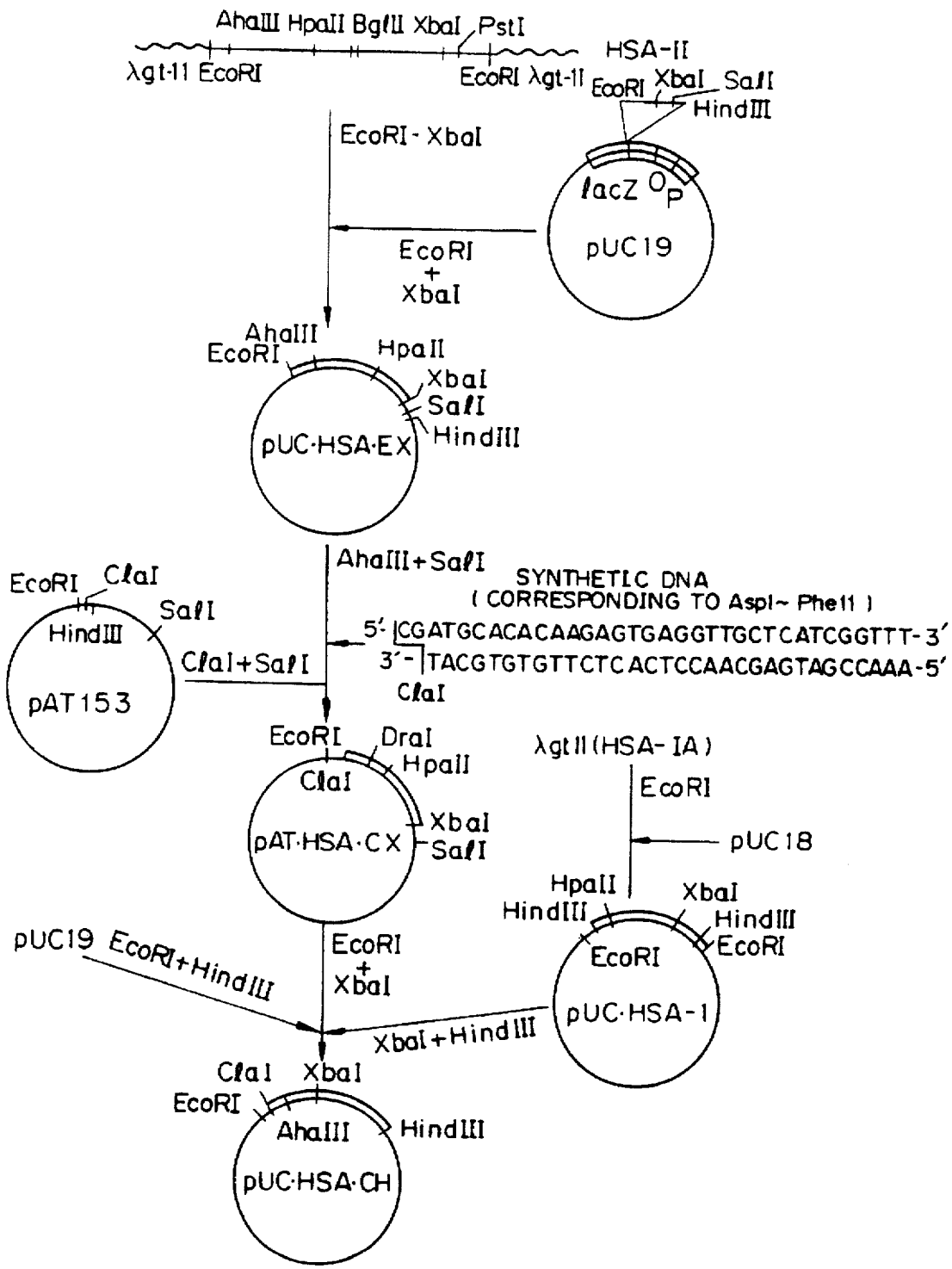
FIG. 10 shows a process of the construction of plasmid PUC.HSA-CH.

As seen in FIG. 8, the HSA-I-A and HSA-II can be cleaved at an appropriate site and rejoined at the corresponding site to construct cDNA correctly coding for a full length of the precursor protein of normal human serum albumin joined with the signal peptide and prosequence.

Reference Example 2

Construction of plasmid PUC-HSA-CH

A clone λgt11 (HSA-II) containing HSA cDNA derived from a human liver cDNA library was cleaved with EcoR I and Xba I to obtain a DNA fragment containing the cDNA. Plasmid pUC19 was cleaved with EcoR I and Xba I to obtain a larger DNA fragment. These DNA fragments were ligated together using T4 DNA ligase to construct a recombinant plasmid pUC-HSA-EX.

The plasmid PUC-HSA-EX was digested with Aha III the Sal I to obtain a smaller DNA fragment which encodes the amino acid sequence from 12th Lys to 356th Thr of normal mature human serum albumin A. To construct a gene coding for normal mature human serum albumin A, a DNA fragment corresponding to the 5'-portion of the mature albumin gene was prepared by annealing two chemically synthesized oligonucleotides. This DNA fragment has, at the 5'-terminal side thereof, an HpaII cleavage site and a Cla I cleavage site to provide cohesive ends which can fuse with the DNA coding for the signal peptide of alkaline phosphatase, and comprises codons coding for the amino acid sequence from the first Asp to 11th Phe of mature human serum albumin A. The annealed DNA fragment was phosphorylated at the 5'-end thereof using T4 puncleotide kinase. On the other hand, a typical *E. coli* multicloning vector pAT 153 (Amersham; Twigg, A. J. and Sherratt, D., Nature, 283 216–218, 1980) was cleaved with Cla I and Sal I, to obtain a larger DNA fragments. The above-prepared three DNA fragment were ligated using T4 DNA ligase to construct a recombinant plasmid pAT-HSA-CX. In this plasmid, DNA coding for the first Asp to 11th Phe is fused with DNA coding for the 12th Lys to 356th Phe. The plasmid pAT-HSA-CX was digested with EcoR I and Xba I to obtain a smaller DNA fragment coding for the first Asp to 356th Phe of the normal human serum albumin.

On the other hand, the phage λgt11 (HSA I-A) selected from the human liver cDNA library, as described above, was digested with EcoR I to obtain a DNA fragment containing a cDNA coding for the C-terminal half of the normal human serum albumin A. The DNA fragment was inserted to the EcoR I site of plasmid pUC18 to construct a recombinant plasmid pUC-HSA-1. This plasmid was digested with Xba I and Hind III to obtain a cDNA fragment containing the region coding for 358th Leu to the 585th carboxy terminal Leu and 3'-terminal non-coding region consisting of 62 nucleotides. On the other hand, a plasmid pUC18 was digested with EcoR I and Hind III to obtain a larger fragment. The above-prepared three DNA fragments were ligated using T4 DNA ligase to construct a recombinant plasmid pUC-HSA-CH containing an entire cDNA coding for normal mature human serum albumin.

A nucleotide sequence of cDNA coding for the entire amino acid sequence of normal mature human serum albumin A and the corresponding amino acid sequence are shown in FIGS. 11-1 to 11-5.

We claim:

1. A DNA comprising a leader DNA coding for a chimeric leader peptide and cDNA coding for mature HSA adjacent to the leader DNA wherein the chimeric leader peptide comprises at its N-terminal side an amino acid sequence readily forming an α-helix having the sequence Met-Lys-Leu-Leu-Leu-Leu-Leu-Leu-Leu-Leu-Phe-Leu-Phe-Ser and at its C-terminal side an amino acid sequence corresponding to the C-terminal sequence of a leader sequence selected from the group consisting of a SUC2 signal peptide, MFα1 signal peptide, PH05 signal peptide and killer toxin signal peptide.

2. A DNA according to claim 1, wherein the chimeric leader peptide is encoded by the following nucleotide sequence:

| | | | | | | | | |
|---|---|---|---|---|---|---|---|---|
| ATG | AAG | TTG | TTG | CTC | CTC | CTT | CTT | TTG | CTC |
| TTC | TTG | TTC | TCT | GCT | AAG | ATT | TCT | GCC. | |

3. A recombinant DNA comprising a DNA coding for a chimeric leader peptide, a cDNA coding for mature HSA, a poly A addition signal and a poly A sequence, in this order, wherein the chimeric leader peptide comprises at its N-terminal side an amino acid sequence readily forming an α-helix having the sequence Met-Lys-Leu-Leu-Leu-Leu-Leu-Leu-Leu-Leu-Phe-Leu-Phe-Ser and at its C-terminal side an amino acid sequence corresponding to the C-terminal sequence of a leader sequence selected from the group consisting of a SUC2 signal peptide, MFα1 signal peptide, PH05 signal peptide and killer toxin signal peptide.

4. A plasmid comprising a promoter and terminator functional in Saccharomyces cerevisiae host cells wherein the recombinant DNA according to claim 3 has been inserted between the promoter and terminator in an orientation which allows expression of the cDNA.

5. A Saccharomyces cerevisiae host transformed with the plasmid according to claim 4.

6. A process for production of a mature HSA comprising culturing the transformed Saccharomyces cerevisiae host according to claim 5 to produce and secrete mature HSA and recovering the mature HSA.

7. A DNA coding for a chimeric leader peptide comprising at its N-terminal side an amino acid sequence readily forming an α-helix having the sequence Met-Lys-Leu-Leu-Leu-Leu-Leu-Leu-Leu-Phe-Leu-Phe-Ser and at its C-terminal side an amino acid sequence corresponding to the C-terminal sequence of a leader sequence selected from the group consisting of a SUC2 signal peptide, MFα1 signal peptide, PH05 signal peptide and killer toxin signal peptide.

* * * * *